United States Patent
Magyar et al.

(10) Patent No.: US 12,227,775 B2
(45) Date of Patent: Feb. 18, 2025

(54) MODIFIED TEMPLATE-INDEPENDENT DNA POLYMERASE

(71) Applicant: The Charles Stark Draper Laboratory, Inc., Cambridge, MA (US)

(72) Inventors: Andrew P. Magyar, Arlington, MA (US); Peter Cavanagh, Stanford, CA (US); Miles Rogers, Cambridge, MA (US); Kirsty A. McFarland, Melrose, MA (US); Melissa M. Sprachman, Somerville, MA (US); Amanda Nicole Billings-Siuti, Framingham, MA (US); Nicole E. Raustad, Charlestown, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 496 days.

(21) Appl. No.: 16/614,819

(22) PCT Filed: May 22, 2018

(86) PCT No.: PCT/US2018/033798
§ 371 (c)(1),
(2) Date: Nov. 19, 2019

(87) PCT Pub. No.: WO2018/217689
PCT Pub. Date: Nov. 29, 2018

(65) Prior Publication Data
US 2020/0263152 A1 Aug. 20, 2020

Related U.S. Application Data

(60) Provisional application No. 62/542,410, filed on Aug. 8, 2017, provisional application No. 62/509,549, filed on May 22, 2017.

(51) Int. Cl.
| | |
|---|---|
| *C12N 9/12* | (2006.01) |
| *C07C 245/08* | (2006.01) |
| *C07C 247/04* | (2006.01) |
| *C12P 19/34* | (2006.01) |
| *C12Q 1/68* | (2018.01) |

(52) U.S. Cl.
CPC .......... *C12N 9/1264* (2013.01); *C07C 245/08* (2013.01); *C07C 247/04* (2013.01); *C12P 19/34* (2013.01); *C12Q 1/68* (2013.01); *C12Y 207/07031* (2013.01)

(58) Field of Classification Search
CPC ..... C07C 245/08; C12N 9/1264; C12P 19/34; C12Y 207/07031; C12Q 2521/01; C12Q 2521/31; C12Q 2523/319
See application file for complete search history.

(56) References Cited

U.S. PATENT DOCUMENTS

| | | |
|---|---|---|
| 5,243,540 A | 9/1993 | Van Albert et al. |
| 5,840,841 A | 11/1998 | Zuckermann et al. |
| 6,232,066 B1 | 5/2001 | Felder et al. |
| 6,238,869 B1 | 5/2001 | Kris et al. |
| 6,664,079 B2 | 12/2003 | Ju et al. |
| 6,819,469 B1 | 11/2004 | Koba |
| 7,883,869 B2 | 2/2011 | Ju et al. |
| 9,384,320 B2 | 7/2016 | Church |
| 9,708,358 B2 | 7/2017 | Ju et al. |
| 9,833,761 B2 | 12/2017 | Banyai et al. |
| 9,897,791 B2 | 2/2018 | Feng |
| 9,928,869 B2 | 3/2018 | Church |
| 9,996,778 B2 | 6/2018 | Church |
| 10,605,734 B2 | 3/2020 | Lafferty et al. |
| 2002/0001075 A1 | 1/2002 | Tsien et al. |
| 2002/0081582 A1 | 6/2002 | Gao et al. |
| 2003/0143132 A1 | 7/2003 | Cerrina et al. |
| 2004/0071394 A1 | 4/2004 | Gfrorer et al. |
| 2004/0197793 A1 | 10/2004 | Hassibi et al. |
| 2006/0154264 A1 | 7/2006 | Cerrina |
| 2007/0116607 A1 | 5/2007 | Wang et al. |
| 2007/0224616 A1 | 9/2007 | Gulari et al. |
| 2008/0085564 A1 | 1/2008 | Hartzell et al. |
| 2009/0023609 A1 | 1/2009 | Jung et al. |
| 2011/0092380 A1 | 4/2011 | Stahler et al. |
| 2015/0269313 A1 | 9/2015 | Church |
| 2016/0108382 A1 | 4/2016 | Efcavitch et al. |
| 2016/0358055 A1 | 12/2016 | Church |
| 2019/0009240 A1 | 1/2019 | Magyar et al. |

(Continued)

FOREIGN PATENT DOCUMENTS

| | | |
|---|---|---|
| EP | 0 969 083 | 1/2000 |
| EP | 1 215 623 | 6/2002 |

(Continued)

OTHER PUBLICATIONS

Motea et al. Terminal deoxynucleotidyl transferase: The story of a misguided DNA polymerase. Biochimica et Biophysica Acta 1804 (2010) 1151-1166. (Year: 2010).*
Modak et al. Biochemistry of Terminal Deoxynucleotidyl Transferase. The Journal of Biologicaclh Emistry vol. 257, No. 24. h u e of Dec. 25, p. 15105-15109, (1982). (Year: 1982).*
Poloni et al. A Fast, Visible-Light-Sensitive Azobenzene for Bioorthogonal Ligation. Chem. Eur. J. (2014), 20, 946-951. (Year: 2014).*
Magnus et al. Direct N-Alkyl Azidonation of N,JV-Dialkylarylamines with the Iodosylbenzene/Trimethylsilylazide Reagent Combination. J. Am. Chem. Soc (1993), 115, 9347-9348. (Year: 1993).*

(Continued)

*Primary Examiner* — Sean C. Barron
(74) *Attorney, Agent, or Firm* — Wolf, Greenfield & Sacks, P.C.

(57) ABSTRACT

Described herein are genetically engineered template-independent DNA polymerases, specifically terminal deoxynucleotidyl transferases, and methods of using these polymerases to control DNA synthesis by adding a single nucleotide (mononucleotide) at a time to the 3' end of a growing single-stranded DNA polynucleotide.

31 Claims, 38 Drawing Sheets

Specification includes a Sequence Listing.

(56) References Cited

U.S. PATENT DOCUMENTS

| | | |
|---|---|---|
| 2019/0112626 A1 | 4/2019 | Lee et al. |
| 2019/0112627 A1 | 4/2019 | Arlow et al. |
| 2019/0354871 A1 | 11/2019 | McFarland et al. |

FOREIGN PATENT DOCUMENTS

| | | |
|---|---|---|
| WO | WO 2008049795 | 5/2008 |
| WO | WO 20120154201 | 11/2012 |
| WO | WO 2014/014991 A2 | 8/2016 |
| WO | WO 2016/128731 A4 | 8/2016 |
| WO | WO 2016/139477 A1 | 9/2016 |
| WO | WO 2017/011492 A1 | 1/2017 |
| WO | WO 2017/156218 A1 | 9/2017 |
| WO | WO 2017176541 | 10/2017 |
| WO | WO 2017/189794 A1 | 11/2017 |
| WO | WO 2017222710 | 12/2017 |
| WO | WO 2017223517 | 12/2017 |
| WO | WO 2018/119253 A1 | 6/2018 |
| WO | WO 2018102554 | 6/2018 |
| WO | WO 2018217689 | 11/2018 |
| WO | WO 2019079802 | 4/2019 |

OTHER PUBLICATIONS

Maezawa et al. Ubiquitylation of Terminal Deoxynucleotidyltransferase Inhibits Its Activity. PLoS One (2012), 7(7), e39511, 15 pages. (Year: 2012).*

Blackman et al. Tetrazine Ligation: Fast Bioconjugation Based on Inverse-Electron-Demand Diels-Alder Reactivity. JACS (2008), 130(41), 13518-13519. (Year: 2008).*

International Preliminary Report on Patentability, mailed on Nov. 26, 2020, from International Application No. PCT/US2019/032903, filed on May 17, 2019. 10 pages.

International Search Report and Written Opinion of the International Searching Authority, mailed on Sep. 21, 2018, from International Application No. PCT/US2018/033798, filed on May 22, 2018. 18 pages.

Hoppmann, C. et al., "Photoswitchable Click Amino Acids: Light Control of Conformation and Bioactivity," ChemBioChem, 12(17):2555-2559 (2011).

Marcandalli, B. et al., "Thermodynamic Study of Solvent and Substituent Effects on 4-Substituted Aminoazobenzenes," Dyes and Pigments, 8(4):239-251 (1987).

Tuuttila, T. et al., "Chiral donor-pi-acceptor azobenzene dyes," Dyes and Pigments, 80(1):34-40 (2009).

XP-002784474, Mouse terminal deoxynucleotidyl transferase (TdT), SEQ ID 9. Retrieved from EBI accession No. GSP:BCP96833 (2016).

Zhang, J. et al., "Synthesis and confirmational study of novel, stable, helical poly(N-propargylamides) containing dipole azobenzene chromophores in the side chains," Polym. Bull., 71(11):2803-2818 (2014).

International Preliminary Report on Patentability mailed on Jan. 23, 2020, from International Application No. PCT/US2018/041397, filed on Jul. 10, 2018. 12 pages.

Boukhet, M., et al., "Translocation of Precision Polymers through Biological Nanopores," Macromol. Rapid Commun. 38 (24), 1700680: 1-6 (2017).

International Search Report and Written Opinion of the International Searching Authority, mailed on Oct. 25, 2019, from International Application No. PCT/US2019/032903, filed on May 17, 2019. 18 pages.

International Search Report and Written Opinion, mailed on Oct. 26, 2018, from International Application No. PCT/US2018/041397, filed on Jul. 10, 2018. 19 pages.

Ju, J., et al., "Four-color DNA sequencing by synthesis using cleavable fluorescent nucleotide reversible terminators," Proceedings of the National Academy of Sciences, 103(52): 19635-19640 (2006).

Klein, J.C., et al., "Multiplex pairwise assembly of array-derived DNA oligonucleotides," Nucleic Acids Research, 44(5): 1-10, e43 (2016).

König, N.F., et al., "Photocontrolled Synthesis of Abiotic Sequence-Defined Oligo (Phosphodiester)s," Macromolecular rapid communications, 38(24): 1700651 (2017).

Orski, S.V., et al., "High density orthogonal surface immobilization via photoactivated copper-free click chemistry," J.Am. Chem. Soc., 132 (32), 11024-11026 (2010).

Palluk, S., et al., "De novo DNA Synthesis Using Polymerase Nucleotide Conjugates," Nature Biotechnology, 36(7): 645-650 (2017).

Partial Search Report of the International Searching Authority, mailed on Sep. 2, 2019, from International Application No. PCT/US2019/032903, filed on May 17, 2019. 10 pages.

Partial Search Report of the International Searching Authority, mailed on Sep. 3, 2018, from International Application No. PCT/US2018/041397, filed on Jul. 10, 2018. 12 pages.

Samanta, S., et al., "Bidirectional Photocontrol of Peptide Conformation with a Bridged Azobenzene Derivative," Angew. Chem. Int. Ed., 51: 6452-6455 (2012).

International Preliminary Report on Patentability, mailed on Dec. 5, 2019, from International Application No. PCT/US2018/033798, filed on May 22, 2018. 9 pages.

Amiram, M., et al., "Evolution of Translation Machinery in Recoded Bacteria Enables Multi-Site in Incorporation of Nonstandard Amino Acids," Nature Biotechnology, 33(12): 1272-1282 (2015).

Chi, L., et al., "A Blue-Green Absorbing Cross-Linker for Rapid Photoswitching of Peptide Helix Content," Bioconjugate Chem., 17: 670-676 (2006).

Clardy, S.M., et al., "Fluorescent Exendin-4 Derivatives for Pancreatic ß-Cell Analysis," Bioconjugate Chem., 25: 171-177 (2014).

Costi, R., et al., "New Nucleotide-Competitive Non-Nucleoside Inhibitors of Terminal Deoxynucleotidyl Transferase: Discovery, Characterization, and Crystal Structure in Complex with the Target," J. Med. Chem., 56: 7431-7441 (2013).

Delarue, M., et al., "Crystal Structure of a Template-Independent DNA Polymerase: Murine Terminal Deoxynucleotidyltransferase," EMBO Journal, 21(3): 427-439 (2002).

Gouge, J., et al., "Structure of Intermediates Along the Catalytic Cycle of Terminal Deoxynucleotidyltransferase: Dynamical Aspects of the Two-Metal Ion Mechanism," J. Mol. Biol., 425: 4334-4352 (2013).

Hamon, F., et al., "Azobenzenes—Synthesis and Carbohydrate Applications," Tetrahedron, 65: 10105-10123 (2009).

Jewett, J.C., et al., "Rapid Cu-Free Click Chemistry with Readily Synthesized Biarylazacyclooctynones," J. Am. Chem. Soc., 132: 3688-3690 (2010).

Karver, M.R., et al., "Bioorthogonal Reaction Pairs Enable Simultaneous, Selective, Multi-Target Imaging," Angew. Chem. Int. Ed., 51: 920-922 (2012).

Kienzler, M.A., et al., "A Red-Shifting, Fast-Relaxing Azobenzene Photoswitch for Visible Light Control of an Ionotropic Glutamate Receptor," J. Am., Chem. Soc., 135: 17683-17686 (2013).

Kolb, H.C., et al., "Click Chemistry: Diverse Chemical Function from a Few Good Reactions," Angew. Chem. Int. Ed., 40: 2004-2021 (2001).

Konig, N.F., et al., "Photocontrolled Synthesis of Abiotic Sequence-Defined Oligo(Phosphodiester)s," Macromol. Rapid Commun., 38: 1700651 (2017).

Li, L., et al., "A Switchable Two-Photon Membrane Tracer Capable of Imaging Membrane-Associated Protein Tyrosine Phosphatase Activities," Angew. Chem. Int. Ed., 52: 424-428 (2013).

Loh, Y., et al., "Click" Synthesis of Small Molecule-Peptide Conjugates for Organelle-Specific Delivery and Inhibition of Lysosomal Cysteine Protease," Chem. Commun., 46: 8407-8409 (2010).

Moon, A.F., et al., "Structural Insight into the Substrate Specificity of DNA Polymerase µ," Nature Structural & Molecular Biology, 14(1): 45-54 (2007).

Patterson, D.M., et al., "Finding the Right (Bioorthogonal) Chemistry," ACS Chem. Biol., 9: 592-605 (2014).

(56) References Cited

OTHER PUBLICATIONS

Pickens, C.J., et al., "Practical Considerations, Challenges, and Limitations of Bioconjugation via Azide-Alkyne Cycloaddition," Bioconjugate Chem., 29: 686-701 (2018).
Rashidian, M., et al., "Use of 18F-2-Fluorodeoxyglucose to Label Antibody Fragments for Immuno-Positron Emission Tomography of Pancreatic Cancer," ACS Cent. Sci., 1: 142-147 (2015).
Reis, S.A., et al.,"Light-Controlled Modulation of Gene Expression by Chemical Optoepigentic Probes," Nature Chemical Biology, 12: 317-326 (2016).
White, E.R., et al., "Replacing Amino Acids in Translation: Expanding Chemical Diversity with Non-Natural Variants," Methods, 60: 70-74 (2013).
Zeglis, B.M., et al., "Building Blocks for the Construction of Bioorthogonally Reactive Peptides via Solid-Phase Peptide Synthesis," ChemistryOpen, 3: 48-53 (2014).
Kumar, K.R.S., et al., "Complete ON/OFF Photoswitching of the Motility of a Nanobiomolecular Machine," ACS Nano, 8(5): 4157-4165 (2014).
Mousavi, S.A., et al., "Glutamate Receptor-Like Genes Mediate Leaf-to-Leaf Signaling," Nature, 500(7463): 422-426 (2013).
Blair, S., et al. "A scalable method for multiplex LED-controlled synthesis of DNA in capillaries," Nucleic Acids Research, 34(16): e110 (2006).
Zhirnov, V., et al. "Nucleic acid memory," Nature materials, 15(4): 366-370 (2016).
Yuen, P.K., "A reconfigurable stick-n-play modular microfluidic system using magnetic interconnects," Lab on a Chip, 16.: 3700-3707 (2016).

\* cited by examiner

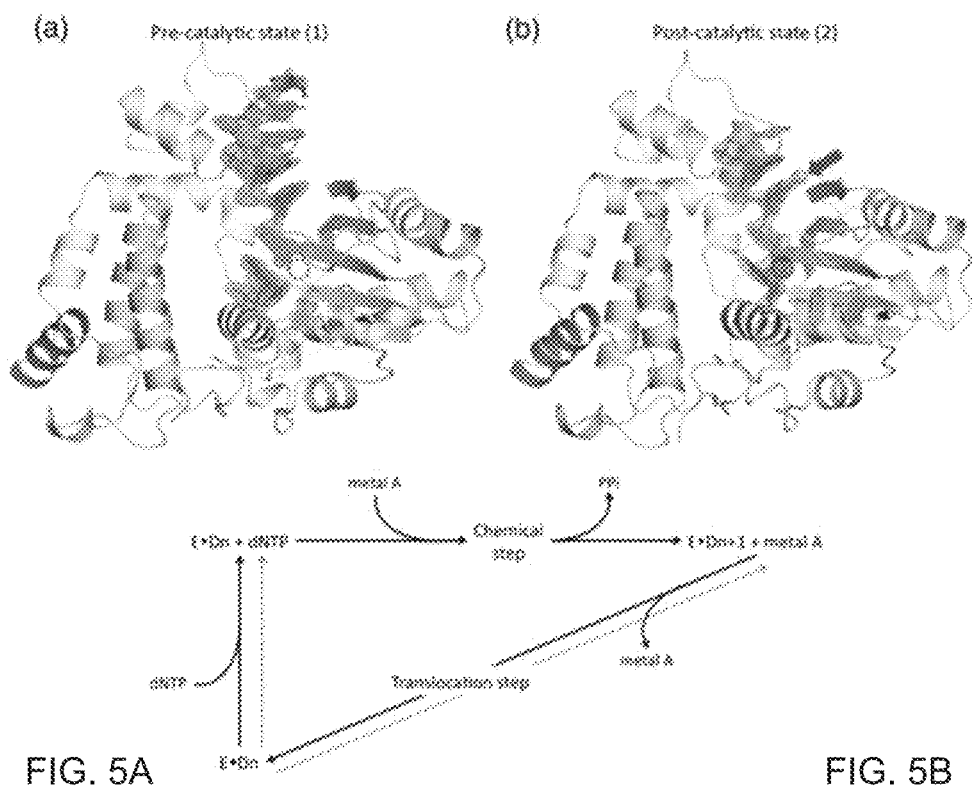
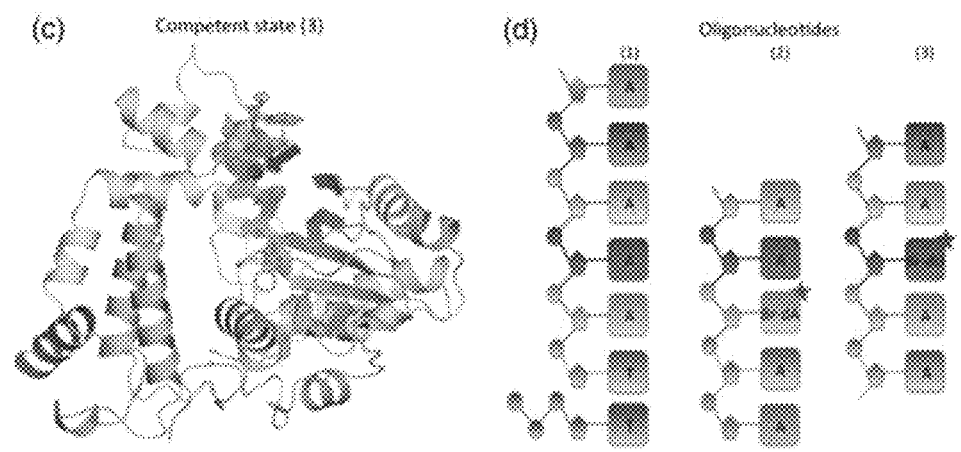
FIG. 5A  FIG. 5B  FIG. 5C  FIG. 5D
From [1] catalytic cycle of TDT Murine TdT MDPLQAVHLGPRKKRPRQLGTPVASMPYDIRFRDLVLFILEKKMGTTRRAFLMELARRKGFRVENELSDSVTHIVAENN
SGSDVLEWLQLQNIKASSEFELLDISWLIECMGAGKPVEMMGRHQLVVNRNSSPSPVPGSQNVPAPAVKKISQYACQ
RRTTLNNYNQLFTDALDILAENDELRENEGSCLAFMRASSVLKSLPFPITSMKDTEGIPCLGDKVKSIIEGIIEDGESSEAKA
VLNDERYKSFKLFTSVFGVGLKTAEKWFRMGFRTLSKIQSDKSLRFTQMQKAGFLYYEDLVSCVNRPEAEAVSMLVKEA
VVTFLPDALVTMTGGFRRGKMTGHDVDFLITSPEATEDEEQQLLHKVTDFWKQQGLLLYCDILESTFEKFKQPSRKVDA
LDHFQKCFLILKLDHGRVHSEKSGQQEGKGWKAIRVDLVMCPYDRRAFALLGWTGSRQFERDLRRYATHERKMMLD
NHALYDRTKRVFLEAESEEEIFAHLGLDYIEPWERNA

FIG. 10A

Bovine TdT

MDPLCTASSGPRKKRPRQVGASMASPPHDIKFQNLVLFILEKKMGTTRRNFLMELARRKGFRVENELSDSVTHIVAEN
NSGSEVLEWLQVQNIRASSQLELLDVSWLIESMGAGKPVEITGKHQLVVRTDYSATPNPGFQKTPPLAVKKISQYACQR
KTTLNNYNHIFTDAFEILAENSEFKENEVSYVTFMRAASVLKSLPFTIISMKDTEGIPCLGDKVKCIIEEIIEDGESSEVKAVL
NDERYQSFKLFTSVFGVGLKTSEKWFRMGFRSLSKIMSDKTLKFTKMQKAGFLYYEDLVSCVTRAEAEAVGVLVKEAV
WAFLPDAFVTMTGGFRRGKKIGHDVDFLITSPGSAEDEEQLLPKVINLWEKKGLLLYYDLVESTFEKFKLPSRQVDTLDH
FQKCFLILKLHHQRVDSSKSNQQEGKTWKAIRVDLVMCPYENRAFALLGWTGSRQFERDIRRYATHERKMMLDNHAL
YDKTKRVFLKAESEEEIFAHLGLDYIEPWERNA

FIG. 10B

Human Tdt

MDPPRASHLSPRKKRPRQTGALMASSPQDIKFQDLVVFILEKKMGTTRRAFLMELARRKGFRVENELSDSVTHIVAEN
NSGSDVLEWLQAQKVQVSSQPELLDVSWLIECIRAGKPVEMTGKHQLVVRRDYSDSTNPGPPKTPPIAVQKISQYACQ
RRTTLNNCNQIFTDAFDILAENCEFRENEDSCVTFMRAASVLKSLPFTIISMKDTEGIPCLGSKVKGIIEEIIEDGESSEVKA
VLNDERYQSFKLFTSVFGVGLKTSEKWFRMGFRTLSKVRSDKSLKFTRMQKAGFLYYEDLVSCVTRAEAEAVSVLVKEA
VWAFLPDAFVTMTGGFRRGKKMGHDVDFLITSPGSTEDEEQLLQKVMNLWEKKGLLLYYDLVESTFEKLRLPSRKVDA
LDHFQKCFLIFKLPRQRVDSDQSSWQEGKTWKAIRVDLVLCPYERRAFALLGWTGSRQFERDLRRYATHERKMILDNH
ALYDKTKRIFLKAESEEEIFAHLGLDYIEPWERNA

FIG. 10C

Shark TdT

MSLAGSLGGMGIIPKRKRQKVTEVCSSQSKHQVRFQDLTIFIVERKMGSSRRSFLMDLARKKGFRVEDVMSDSVTHIVT
ENNSWDEIWDWIQNLKLLNADKLKMLNISWFTDSMAAGKPVEIEERHKLQVQKMLQSNSPLPPPVVTISQYACQRRS
TLNNRNKIFTDALEILAENFEFNENESAYVAFARATSLLKSLPYTISKMAALDGLPCFGDQTRAIIEEILEDGVSSKVDDLLC
DEKYKARKLFTSVFGVGLKTADKWYGQGFRTLEAVKASKDLKFTKMQKAGFLYYEDINNAVTRPEAEAVAQIIETIVHNY
APDAIVTLTGGFRRGKETGHDVDFLISCPETMDENFLRKIVNKLDFRGLLLYYDMVEATFEKRKLSSQKYDAMDHFQKC
FLILKLNKALVKNRVLSMSSVSAARPTDEGAEPEVKTQIKDWKAIRVDLVIVPTQQFAYALLGWTGSRQFERDLRRYTN
HEKSMILDNHGLYDRKKKIFLNAKTEEEIFAHLDLEYIEPWERNA

FIG. 10D

Murine Tdt Catalytic core

NSSPSPVPGSQNVPAPAVKKISQYACQRRTTLNNYNQLFTDALDILAENDELRENEGSCLAFMRASSVLKSLPFPITSMK
DTEGIPCLGDKVKSIIEGIIEDGESSEAKAVLNDERYKSFKLFTSVFGVGLKTAEKWFRMGFRTLSKIQSDKSLRFTQMQK
AGFLYYEDLVSCVNRPEAEAVSMLVKEAVVTFLPDALVTMTGGFRRGKMTGHDVDFLITSPEATEDEEQQLLHKVTDF
WKQQGLLLYCDILESTFEKFKQPSRKVDALDHFQKCFLILKLDHGRVHSEKSGQQEGKGWKAIRVDLVMCPYDRRAFAL
LGWTGSRQFERDLRRYATHERKMMLDNHALYDRTKRVFLEAESEEEIFAHLGLDYIEPWERNA

FIG. 10E

```
MURINE    1   MDPLQAVHLGPRKKRPRQLGTPVASTPYDIRFRDLVLFILEKKMGTTRRA    50
              ||| :: ||:||||||||| ||| |:|||:|||||:||| ||||||||||
HUMAN     1   MDPPRASHLSPRKKRPRQTGALMASSPQDIKFQDLVVFILEKKMGTTRRA    50

MURINE    51  FLMELARRKGFRVENELSDSVTHIVAENNSGSDVLEWLQLQNIKASSELE    100
              |||||||||||||||||||||||||||||||||||||| : :::|:|  
HUMAN     51  FLMELARRKGFRVENELSDSVTHIVAENNSGSDVLEWLQAQKVQVSSQPE    100

MURINE    101 LLDISWLIECMGAGKPVEMMGRHQLVVNRNSSPSPVPGSQNVPAPAVKKI    150
              |||:|||||| || |||||: |||||   :  |:  ::| : ||| |::
HUMAN     101 LLDVSWLIECIRAGKPVEMTGKHQLVRRDYSDSTNPGPPKTPIAVQKI    150

MURINE    151 SQYACQRRTTLNNYNQLFTDALDILAENDELRENEGSCLAFMRASSVLKS    200
              |||||||||||| ||||||||||||||| ||||||| | |||||:||||
HUMAN     151 SQYACQRRTTLNNCNQIFTDAFDILAENCEFRENEDSCVTFMRAASVLKS    200

MURINE    201 LPFPITSMKDTEGIPCLGDKVKSIIEGIIEDGESSEAKAVLNDERYKSFK    250
              ||| ||||||||||||| ||| ||||:|| |||||: ||||||||:||| 
HUMAN     201 LPFTITSMKDTEGIPCLGSKVKGIIEHIIEDGESSEVKAVLNDERYQSFK    250

MURINE    251 LFTSVFGVGLKTAEKWFRMGFRTLSKIQSDKSLRFTQMQKAGFLYYEDLV    300
              |||||||||||| || ||||||||| ||:|:|:|: |::|||||||||:
HUMAN     251 LFTSVFGVGLKTSEKWFRMGFRTLSKVRSDKSLKFTRMQKAGFLYYEDLV    300

MURINE    301 SCVNRPEAEAVSMLVKEAVVTELPDALVTMTGGFRRGKMTGHDVDFLITS    350
              ||| : |||||| ||||||:|:|||| |||||||||| |||||||||||
HUMAN     301 SCVTRAEAEAVSVLVKEAVWAFLPDAFVTMTGGFRRGKKMGHDVDFLITS    350
```

FIG. 11

| | | | |
|---|---|---|---|
| MURINE | 351 | PEATEDEQQLLHKVTDFWKQQGLLLYCDILESTFEKFKQPSRKVDALDH | 400 |
| HUMAN | 351 | PGSTEDEE-QLLQKVMNLWEKKGLLLYDLVESTFEKLRLPSRKVDALDH | 399 |
| MURINE | 401 | FQKCFLILKLDHGRVHSEKSGQQEGKGWKAIRVDLVMCPYDRRAFALLGW | 450 |
| HUMAN | 400 | FQKCFLIFKLPRQRVDSDQSSWQEGKTWKAIRVDLVLCPYERRAFALLGW | 449 |
| MURINE | 451 | TGSRQFERDLRRYATHERKMMLDNHALYDRTKGKTVTISPLDGKVSKLQK | 500 |
| HUMAN | 450 | TGSRQFERDLRRYATHERKMILDNHALYDKTK--------------- | 481 |
| MURINE | 501 | ALRVFLEAESEEEIFAHLGLDYIEPWERNA | 530 |
| HUMAN | 482 | ---RIFLKAESEEEIFAHLGLDYIEPWERNA | 509 |
| MURINE | 1 | MDPLQAVHLGPRKKRPRQLGTPVASTPYDIRFRDLVLFILEKKMGTTRRA | 50 |
| BOVINE | 1 | MDPLCTASSGPRKKRPRQVGASMASPPHDIKFQNLVLFILEKKMGTTRRN | 50 |
| MURINE | 51 | FLMELARRKGFRVENELSDSVTHIVAENNSGSDVLEWLQLQNIKASSELE | 100 |
| BOVINE | 51 | FLMELARRKGFRVENELSDSVTHIVAENNSGSEVLEWLQVQNIRASSQLE | 100 |
| MURINE | 101 | LLIDISWLIECMGAGKPVEMMGRHQLIVNRNSSPSPVPGSQNVPAPAVKKI | 150 |
| BOVINE | 101 | LLDVSWLIESMGAGKPVEITGKHQLIVVRTDYSATPNPGFQKTPPLAVKKI | 150 |

FIG. 11 cont.

| | | | |
|---|---|---|---|
| MURINE | 151 | SQYACQRRTTLNNYNQLFTDALDILAENDELRENEGSCLAFMRASSVLKS | 200 |
| BOVINE | 151 | SQYACQRKTTLNNYNHIFTDAFEILAENSEFKENEVSYVTFMRAASVLKS | 200 |
| MURINE | 201 | LPFPITSMKDTEGIPCLGDKVKSIIEGIIEDGESSEAKAVLNDERYKSFK | 250 |
| BOVINE | 201 | LPFTIISMKDTEGIPCLGDKVKCIIEEIIEDGESSEVKAVLNDERYQSFK | 250 |
| MURINE | 251 | LFTSVFGVGLKTAEKWFRMGFRTLSKIQSDKSLRFTQMQKAGFLYYEDLV | 300 |
| BOVINE | 251 | LFTSVFGVGLKTSEKWFRMGFRSLSKIMSDKTLKFTKMQKAGFLYYEDLV | 300 |
| MURINE | 301 | SCVNRPEAEAVSMLVKEAVVTFLPDALVTMTGGFRRGKMTGHDVDFLITS | 350 |
| BOVINE | 301 | SCVTRAEAEAVGVLVKEAVWAFLPDAFVTMTGGFRRGKKIGHDVDFLITS | 350 |
| MURINE | 351 | PEATEDEEQQLLHKVTDFWKQQGLLLYCDILESTFEKFKQPSRKVDALDH | 400 |
| BOVINE | 351 | PGSAEDEE-QLLPKVINLWEKKGLLLYDLVESTFEKFKLPSRQVDTLDH | 399 |
| MURINE | 401 | FQKCFLILKLDHGRVHSEKSGQQEGKGWKAIRVDLVMCPYDRRAFALLGW | 450 |
| BOVINE | 400 | FQKCFLILKLHHQRVDSSKSNQQEGKTWKAIRVDLVMCPYENRAFALLGW | 449 |
| MURINE | 451 | TGSRQFERDLRRYATHERKMMLDNHALYDRTKGKTVTISPLDGKVSKLQK | 500 |
| BOVINE | 450 | TGSRQFERDIRRYATHERKMMLDNHALYDKTK--- | 481 |
| MURINE | 501 | ALRVFLEAESEEEIFAHLGLDYIEPWERNA | 530 |
| BOVINE | 482 | ---RVFLKAESEEEIFAHLGLDYIEPWERNA | 509 |

FIG. 11 cont.

```
MURINE    1   ----MDPLQAVHLGPRKKRPRQLGTPVASTPYDIRFRDLIVLFILEKKMGTT        47
              . |:.:|||:.||:||||||.||::|.|::|:|:|::|:|||||:|::
SHARK     1   MSLAGSLGGMGIIPKRKRQKVTEVCSSQSKHQVRFQDLTIFIVERKMGSS        50

MURINE   48   RRAFLMELARRKGFRVENELSDSVTHIVAENNSGSDVLEWLQLQNIKASS        97
              ||:|||:|||||||||:|:|||||||||:|.:|||||||||||||||||
SHARK    51   RRSFLMDLARKKGFRVEDVMSDSVTHIVTENNSWDEIWDWIQNLKLLNAD       100

MURINE   98   ELELLDISWLIECMGAGKPVEMMGRHQLVVNRN--SSPSPVFGSQNVPAPA      146
              :|::||||||||::|.|:|:|.::||:|:.:|    ..|.||:|:
SHARK   101   KLKMLNISWFTDSMAAGKPVEIEERHKLQVQKMLQSNSPLP---------PP       143

MURINE  147   VKKISQYACQRRTTLNNYNQLFTDALDIIAENDELRENEGSCLAFMRASS      196
              |..|||||||||:||||:.|:|||||:||:||||:|:|||||::|:|:|
SHARK   144   VVTISQYACQRRSTLNNRNKIFTDALEILAENEFENESAYVAFARATS        193

MURINE  197   VLKSLPFPITSMKDTEGIPCLGDKVKSIIEGIIEDGESSEAKAVLNDERY      246
              :|||||:|:|:|.:|:|||.||:||:||||:|:|||:|:|:|:::||:|
SHARK   194   LLKSLPYTISKMAALDGLPCFGDQTRAIIEEILEDGVSSKVDDLLCDEKY      243

MURINE  247   KSFKLFTSVFGVGLKTAEKWFRMGFRTLSKIQSDKSLRFTQMQKAGFLYY      296
              |:.|||||||||||||||||||||:|||||||:.|.:||||||||||||
SHARK   244   KARKLFTSVFGVGLKTADKWYGQGFRTLEAVKASKDLKFTKMQKAGFLYY      293

MURINE  297   EDLVSCVNRPEAEAVSMLVKEAVVTFLPDALVTMTGGFRRGKMTGHDVDF      346
              ||:.:|.:|||||||.|:||:|::.:|||::|:||||||||:||||||:|
SHARK   294   EDINNAVTRPEAEAVAQIETIVHNYAPDAIVTLTGGFRRGKETGHDVDF      343

MURINE  347   LITSPEATEDEEQQLLHKVTDFWKQQGLLLYCDILESTEEKFKQPSRKVD      396
              ||:.:|:||||::::|::|:.||:||||||.|::|:
SHARK   344   LISCPE-TMDE--NFLRKTVNKLDFRGLLLYDMVEATFEKRKLSSQKYD       390
```

FIG. 11 cont.

```
MURINE   397 ALDHFQKCFLIIKLDHGRVH------------------------SEKSGQQEGKGW    428
             |:||||||||||||||.....:.                      :|....:..|.|.
SHARK    391 AMDHFQKCFLILKLINKALVKNRVLSMSSVSAARPTDEGAEPEVKTQIKDW         440

MURINE   429 KAIRVDLVMCPYDRRAFALLGWTGSRQFERDLRRYATHERKMMLDNHALY          478
             ||||||||:|.|:|::||||||||||||||||||||:..|:||.|||:||
SHARK    441 KAIRVDLIVPTQQFAYALLGWTGSRQFERDLRRYTNHEKSMILDNHGLY           490

MURINE   479 DRTKGKTVTISPLDGKVSKLQKALRVFLEAESEEEIFAHLGLDYIEPWER          528
             ||.|                  ::|||:||||||||||||:||:|||||
SHARK    491 DRKK------------------KIFLNAKTEEEIFAHLDLEYIEPWER            520

MURINE   529 NA  530
             ||
SHARK    521 NA  522

SHARK    MSLAGSLGMGIIPKRKRQKVTEVCSSQSKHQVRFQDLTIFIVERKMGSSRRSFLMDLAR
MURINE   ---MDPLQAVHLGPRKKRPRQLGTPVASTPYDIRFRDLVLFILEKKMGTTRRAFLMELAR
BOVINE   ---MDPLCTASSGPRKKRPRQVGASMASPPHDIKFQNLVLFILEKKMGTTRRNFLMELAR
HUMAN    ---MDPPRASHLSPRKKRPRQTGALMASSPQDIKFQDLVVFILEKKMGTTRRAFLMELAR
                     *.**    .   ..    :   ..:*..*:.***.:**.***:***

SHARK    RKGFRVEDVMSDSVTHIVTENNSWDEIWDWIQNLKLLNADKLKMLNISWFTDSMAAGKPV
MURINE   RKGFRVENELSDSVTHIVAENNSGSDVLEWLQLQNIKASSELELLDISWLIECMGAGKPV
BOVINE   RKGFRVENELSDSVTHIVAENNSGSEVLEWLQVQNIRASSQLELLDVSWLIESMGAGKPV
HUMAN    RKGFRVENELSDSVTHIVAENNSGSDVLEWLQAQKVQVSSQPELLDVSWLIECIRAGKPV
         *******:  ***** :  **: : ::*  *.:    .: **:*:**:*.  :.****
```

FIG. 11 cont.

```
SHARK    EIEERHKLQVQKMLQSNS------PLPPPVVT-ISQYACQRRSTLNNRNKIFTDALEILAE
MURINE   EMMGRHQLVVNRNSSPSPVPGSQNVPAPAVKKISQYACQRRTTLNNYNQLFTDALDILAE
BOVINE   EITGKHQLVVRTDYSATPNPGFQKTPPLAVKKISQYACQRKTTLNNYNHIFTDAFEILAE
HUMAN    EMTGKHQLVVRRDYSDSTNPGPPKTPPIAVQKISQYACQRRTTLNNCNQIFTDAFDILAE
          *  :****  .  :       *   * : :***** **::**** ** : ***:: :**

SHARK    NFEFNENESAYVAFARATSLLKSLPYTTSKMAALDGLPCFGDQTRAIIEEILEDGVSSKV
MURINE   NDELRENEGSCLAFMRASSVLKSLPFPITSMKDTEGIPCLGDKVKSIIEGIIEDGESSEA
BOVINE   NSEFKENEVSYVTFMRAASVLKSLPFTIISMKDTEGIPCLGDKVKCIIEEIIEDGESSEV
HUMAN    NCEFRENEDSCVTFMRAASVLKSLPFTIISMKDTEGIPCLGSKVKGIIEEIIEDGESSEV
         *  : ***.*   * *::****** * *** *  * *  *.  .  ***.****.**.

SHARK    DDLLCDEKYKARKLFTSVFGVGLKTADKWYGQGFRTLEAVKASKDLKFTKMQKAGFLYYE
MURINE   KAVLNDERYIKSFKLFTSVFGVGLKTAEKWFRMGFRTLSKIQSDKSLRFTQMQKAGFLYYE
BOVINE   KAVLNDERYQSFKLFTSVFGVGLKTSEKWFRMGFRSLSKIMSDKTLKFTKMQKAGFLYYE
HUMAN    KAVLNDERYQSFKLFTSVFGVGLKTSEKWFRMGFRTLSKVRSDKSLKFTRMQKAGFLYYE
          .:: ::*  . ::**********::** . ***:*.::  .* *:**::********

SHARK    DINNAVTRPEAEAVAQIIETIVHNYAPDAIVTLTGGFRRGKETGHDVDFLISCPETMDE-
MURINE   DLVSCVNRPEAEAVSMLVKEAVVTFLPDALVTMTGGFRRGKMTGHDVDFLITSPEATEDE
BOVINE   DLVSCVTRAEAEAVGVLVKEAVWAFLPDAFVTMTGGFRRGKKIGHDVDFLITSPGSAEDE
HUMAN    DLVSCVTRAEAEAVSVLVKEAVWAFLPDAFVTMTGGFRRGKKMGHDVDFLITSPGSTEDE
         *:  .*.* :***.   ::::::  :*** **:*******    ********:  .  :
```

FIG. 11 cont.

```
SHARK   ---NFLRKIVNKLDFRGLLLYYDMVEATFEKRKLSSQKYDAMDHFQKCFLILKLNKALVKN
MURINE  EQQLLHKVTDFWKQQGLLLYCDILESTFEKFQPSRKVDALDHFQKCFLILKLDHGRVH-
BOVINE  E-QLLPKVINLWEKKGLLLYYDLVESTFEKFKLPSRQVDTLDHFQKCFLILKLHHQRVD-
HUMAN   E-QLLQKVMNLWEKKGLLLYYDLVESTFEKLRLPSRKVDALDHFQKCFLIFKLPRQRVD-
          .  :    *  ****  :  *::*:***   .  . *.:  ****** :* *  . *

SHARK   RVLSMSSVSAARPTDEGAEPEVKTQIKDWKAIRVDLIVPTQQFAYALLGWTGSRQFERD
MURINE  -------SEKSGQQEG------KGWKAIRVDLVMCPYDRRAFALLGWTGSRQFERD
BOVINE  -------SSKSNQQEG------KTWKAIRVDLVMCPYENRAFALLGWTGSRQFERD
HUMAN   -------SDQSSWQEG------KTWKAIRVDLVLCPYERRAFALLGWTGSRQFERD
               *  *          * ******::  *: :. *************

SHARK   LRRYTNHEKSMILDNHGLYDRKK-------KIFLNAKTEEEIFAHLD
MURINE  LRRYATHERKMMLDNHHALYDRTKGKTVTISPLDGKVSKLQKALRVFLEAESEEEIFAHLG
BOVINE  IRRYATHERKMMLDNHHALYDKTK-------RVFLKAESEEEIFAHLG
HUMAN   LRRYATHERKMILDNHHALYDKTK-------RIFLKAESEEEIFAHLG
        :***.:*****::****. ***:.              ::*  ::.:********.

SHARK   LEYIEPWERNA
MURINE  LDYIEPWERNA
BOVINE  LDYIEPWERNA
HUMAN   LDYIEPWERNA
        *:*********
```

FIG. 11 cont.

```
MURINE    MDPLQAVHLGPRKKRPRPRQLGTPVASTPYDIREDLVLFILEKKMGTTRRAFLMELARRKG
BOVINE    MDPLCTASSGPRKKKRPRQVGASMASPPHDIKFQNLVLFILEKKMGTTRRNFLMELARRKG
HUMAN     MDPPRASHLSPRKKRPRQTGALMASSPQDIKFQDLVVFILEKKMGTTRRAFLMELARRKG
              :  .   *****:** .:  *:: :.*:. *::*:******** :**********

MURINE    FRVENELSDSVTHIVAENNSGSDVLEWLQLQNIKASSELELLDISWLIECMGAGKPVEMM
BOVINE    FRVENELSDSVTHIVAENNSGSEVLEWLEWLQVQNIRASSQLELLDVSWLIESMGAGKPVEIT
HUMAN     FRVENELSDSVTHIVAENNSGSDVLEWLQAQKVQVSSQPELLDVSWLIECIRAGKPVEMT
          *********************:****  .::: *.: ****:*****   ****:

MURINE    GRHQLVNRNSSPSPVPGSQNVPAPAVKKISQYACQRRTTLNNYNQLFTDALDILAENDE
BOVINE    GKHQLVVRTDYSATPNPGFQKTPPLAVKKISQYACQRKTTLNNYNHIFTDAFEILAENSE
HUMAN     GKHQLVVRRDYSDSTNPGPPKTPPIAVQKISQYACQRRTTLNNCNQIFTDAFDILAENCE
          *:****  .  * :.*** ::**:**:*********:**** *::***: :****. :

MURINE    LRENEGSCLAFMRAASVLKSLPFPITSMKDTEGIPCLGDKVKSIIEGIIEDGESSEAKAV
BOVINE    FKENEVSYVTFMRAASVLKSLPFTIISMKDTEGIPCLGDKVKCIIEELIEDGESSEVKAV
HUMAN     FRENEDSCVTFMRAASVLKSLPFTIISMKDTEGIPCLGSKVKGIIEELIEEIEDGESSEVKAV
          ::***.*  .:***********  *:*************.***  ***:*********.***

MURINE    LNDERYKSFKLFTSVFGVGLKTAEKWFRMGFRTLSKIQSDKSLRFTQMQKAGFLYYEDLV
BOVINE    LNDERYQSFKLFTSVFGVGLKTSEKWFRMGFRSLSKIMSDKTLKFTKMQKAGFLYYEDLV
HUMAN     LNDERYQSFKLFTSVFGVGLKTSEKWFRMGFRTLSKVRSDKSLKFTRMQKAGFLYYEDLV
          ******:***************:*********:***: ***:*:**:************
```

FIG. 11 cont.

```
MURINE    SCVNRPEAEAVSMLVKEAVVTFLPDALVTMTGGFRRGKMTGHDVDFLITSPEATEDEEQQ
BOVINE    SCVTRAEAEAVGVLVKEAVWAFLPDAFVTMTGGFRRGKKIGHDVDFLITSPGSAEDEE-Q
HUMAN     SCVTRAEAEAVSVLVKEAVWAFLPDAFVTMTGGFRRGKKMGHDVDFLITSPGSTEDEE-Q
          ***.*.:*****.:******** ****:*******.*********** * ****  ;**:*

MURINE    LLHKVTDFWKQQGLLLYCDILESTFEKFKQPSRKVDALDHFQKCFLILKLDHGRVHSEKS
BOVINE    LLPKVINLWEKKGLLLYYDLVESTFEKFKLPSRQVDTLDHFQKCFLILKLHHQRVDSSKS
HUMAN     LLQKVMNLWEKKGLLLYYDLVESTFEKLRLPSRKVDALDHFQKCFLIFKLPRQRVDSDQS
          ** **  :*:::****  *::******: :***:**:********:***  :**.*: *

MURINE    GQQEGKGWKAIRVDLVMCPYDRRAFALLGWTGSRQFERDLRRYATHERKMMLDNHALYDR
BOVINE    NQQEGKTWKAIRVDLVMCPYENRAFALLGWTGSRQFERDIRRYATHERKMMLDNHALYDK
HUMAN     SWQEGKTWKAIRVDLVLCPYERRAFALLGWTGSRQFERDLRRYATHERKMILDNHALYDK
           .****.********:***:.*********************:*********:******:

MURINE    TKGKTVTISPLDGKVSKLQKALRVFLEAESEEEIFAHLGLDYIEPWERNA
BOVINE    TK------------------RVFLKAESEEEIFAHLGLDYIEPWERNA
HUMAN     TK------------------RIFLKAESEEEIFAHLGLDYIEPWERNA
          **                  *:***********************

FIG. 11 cont.
```

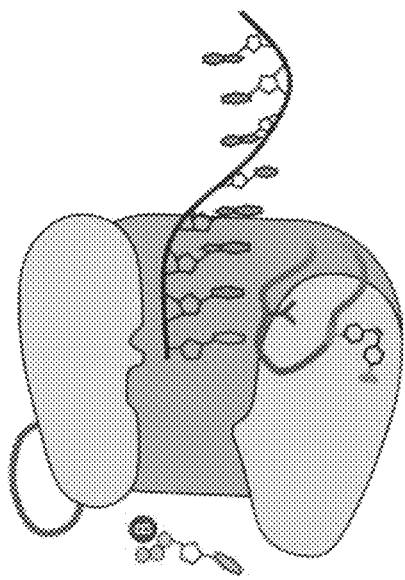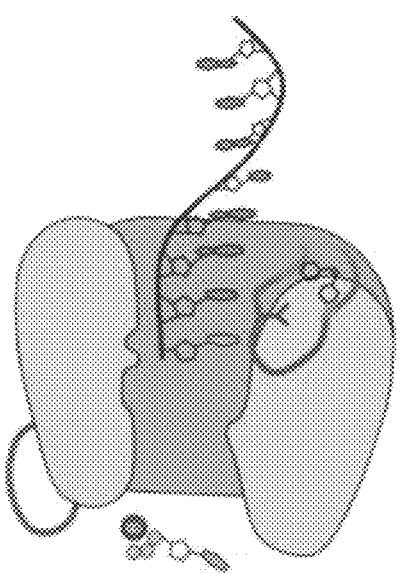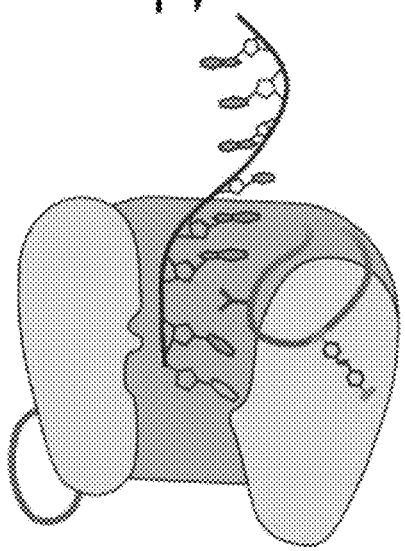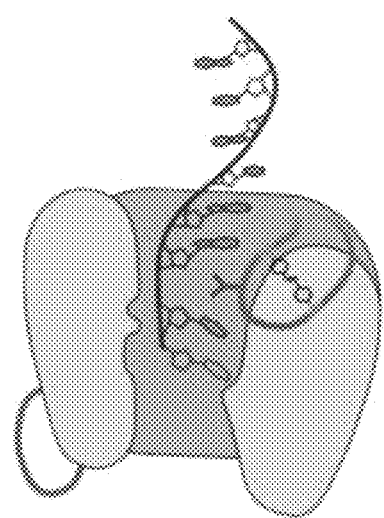
FIG. 13A
FIG. 13B

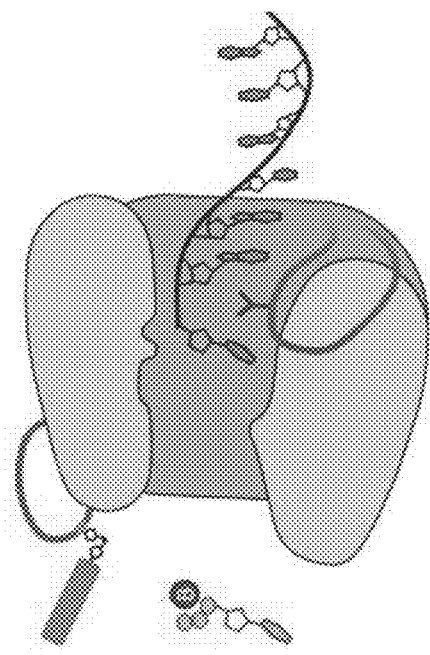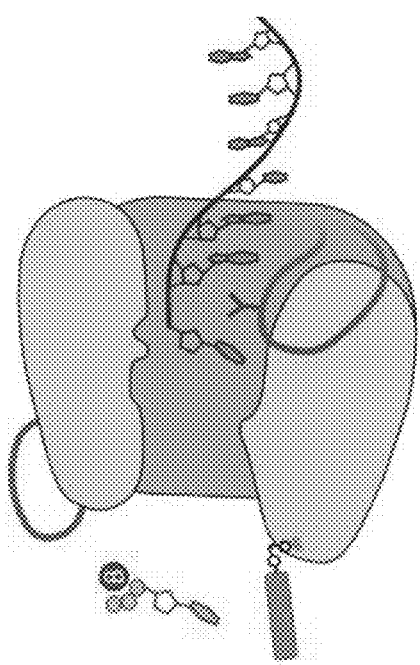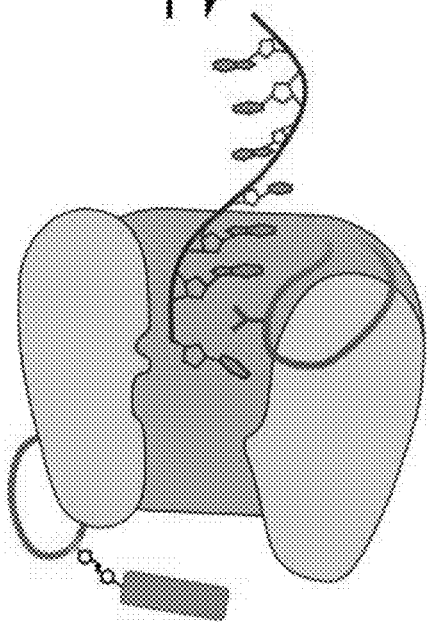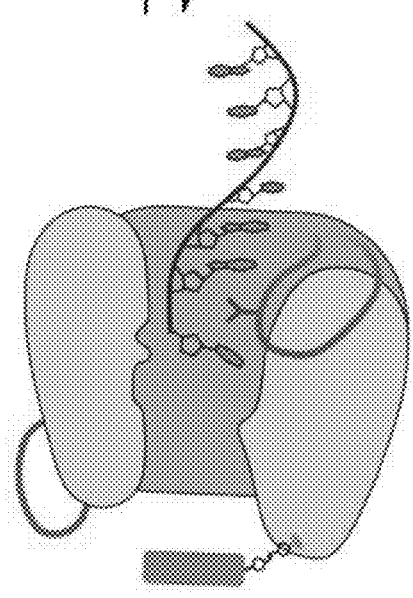
FIG. 14A
FIG. 14B

MODIFIED TEMPLATE-INDEPENDENT DNA POLYMERASE

RELATED APPLICATIONS

This application is a § 371 National Phase Application of International Application No. PCT/US2018/033798, filed on May 22, 2018, now International Publication No. WO 2018/217689 A1, published on November 29, 2018, which International Application claims the benefit under 35 U.S.C. § 119 (e) of U.S. Provisional Application Nos. 62/542,410, filed on Aug. 8, 2017 and 62/509,549 filed May 22, 2017, all of which are incorporated herein by reference in their entirety.

INCORPORATION BY REFERENCE OF MATERIAL IN ASCII TEXT FILE

This application incorporates by reference the Sequence Listing contained in the following ASCII text file:
File name:
0352-0024WO1_CSDL-6045-WO-01_Sequence_Listing Replacement_ST25.txt; created Aug. 7, 2018, 21 KB in size.

BACKGROUND OF THE INVENTION

DNA polymerases are enzymes responsible for the replication of genetic material in vivo and in vitro. Specifically, these enzymes are responsible for catalyzing the addition of nucleotide triphosphates (e.g., dNTPs and analogs thereof) to the three-prime end of a primer or seed strand of DNA. The majority of DNA polymerases replicate DNA in a largely template-dependent manner. That is: synthesizing the reverse complement strand of a DNA strand. However, a few polymerases have template-independent activity, wherein they can synthesize random sequences of DNA without the influence or need of a template strand.

Terminal deoxynucleotidyl transferase (also referred to herein as Tdt or TDT) is a DNA polymerase capable of catalyzing the random addition of nucleotides. In vivo, specifically in premature immune cells undergoing antibody and t cell receptor recombination, TdT acts in conjunction with DNA repair pathways to generate highly diverse sequences at VDJ junction sites. In vitro, TdT also displays template-independent activity, enabling its widespread use for applications such as poly A tailing of DNA. Because TdT does not require a DNA primer strand for DNA synthesis it is an ideal enzyme for in vitro DNA synthesis (see, e.g., Gouge, Jérôme, et al. "Structures of intermediates along the catalytic cycle of terminal deoxynucleotidyl transferase: dynamical aspects of the two-metal ion mechanism." Journal of Molecular Biology 425.22 (2013): 4334-4352). However, TdT adds nucleotides in an uncontrolled manner, and therefore has not yet been successfully used for the synthesis of sequence-specific DNA. While this template independence provides a means to synthesize entirely novel sequences of DNA from scratch, to do so in a highly controlled and sequence specific manner requires the control of the enzyme.

The availability of a TdT enzyme capable of controllably adding or inserting a single nucleotide (mononucleotide) at a time would enable new DNA synthesis strategies not previously possible, with benefits over existing strategies, and in particular would enable control of the enzyme for the synthesis of sequence-specified DNA, RNA, or other nucleic acid molecules.

SUMMARY OF THE INVENTION

The present invention encompasses compositions, methods and kits for improved polynucleotide synthesis. Specifically described herein are methodologies for engineering the terminal deoxynucleotidyl transferase protein/enzyme in order to control the addition of nucleotides to a growing nucleotide strand. TdT may be engineered by a number of methods described herein, including, but not limited to: careful control of the enzyme's environment, specific changes made to the enzyme's amino acid sequence, exogenous molecular components added to the system, and generally, modifications made to the structure and mechanism of the enzyme.

Terminal deoxynucleotidyl transferase is a template-independent DNA polymerase. As described herein, an engineered TdT can be used to controllably synthesize DNA of a desired sequence. Specifically described herein is an engineered terminal deoxynucleotidyl transferase (TdT), wherein one, or more, amino acid residues of the TdT are modified either through genetically controlled substitution of amino acids and/or chemical modifications, resulting in a TdT capable of controlled addition of nucleotides to the 3' end of a single-stranded polynucleotide. Engineering modifications to TdT can enable photo control of the enzymatic polymerase activity (e.g., the use of light to control DNA synthesis).

In one embodiment of the present invention, the engineered TdT is a photoisomerizable TdT, and in particular, a TdT wherein one, or more amino acid residues of the TdT are substituted with a non-naturally occurring amino acid comprising a photoswitchable moiety, such as an azobenzene derivative. The use of a modified TdT comprising an azobenzene photoswitch, for example, can controllably block entry or binding of nucleotides into the active site of the enzyme, thereby inhibiting, regulating or gating entry or binding of a mononucleotide to the active site of TdT.

Based on the crystal structure of murine TdT from Gouge et al. (J. Mol. Biol. (2013) 425, p. 4334-4352), as described herein, suitable locations have been identified as targets for the addition of one, or more, photoswitchable moieties. Some residues found in murine TdT have been excluded from the crystal structure, potentially due to their contribution to disorder in the structure. Residues absent from the crystal structure can also be desirable targets for engineering. For example, suitable residues are surface exposed and do not typically play an important role in enzyme function. (See FIG. 1). The complete amino acid sequence of murine TdT is described herein as SEQ ID NO: 1.

Suitable residue locations are, for example, the lysines at positions 199, 238, 247, 250, 276, 338 or 419 of the murine TdT (SEQ ID NO:1). Sequences of homologous TdTs are described herein (bovine SEQ ID NO:2; human SEQ ID NO:3; and shark SEQ ID NO:4; and the catalytic core of murine TdT (SEQ ID NO:5)). Other homologous TdTs are known to those skilled in the art. Specifically, homologous TdTs that are suitable for the engineered modifications described herein will have at least about 30%, 40%, 50%, 60%, 70%, 80%, 90%, 95% or greater sequence identity with SEQ ID NO:1 or with SEQ ID NO:5. There are a number of additional residues that can also be reasonably suitable for modification with a photoswitchable moiety, and, based on the description herein, locations of these residues can be readily ascertained by one of skill in the art.

Also encompassed by the present invention are the nucleic acid sequences corresponding to the amino acid sequences described above. Corresponding nucleic acid sequences are nucleic acids that encode their respective TdT amino acid sequences, e.g., SEQ ID NOs: 1-5, and other suitable homologous TdT sequences. Such encoding nucleic acids and their nucleic acid sequences can be determined by those of skill in the art using standard, routine methods.

Photoswitchable moieties can be introduced into a DNA polymerase, and in particular the TdT, through the incorporation of non-natural/unnatural amino acids through methods such as using custom tRNAs, e.g., for example, the Amber codon (UAG). The Amber codon can be used to genetically regulate the incorporation of the non-natural amino acids at particular residue sites (site-specific incorporation) within the specific protein. These techniques are known to those skilled in the art. These amino acids can either directly contain the photoswitchable group, or contain a click reactive group, such as dibenzocyclooctyne (DBCO), to which the photoswitch molecule can be attached. The DBCO can react with an azide on the photoswitch to form a covalent bond.

In some cases, attachment of a photoactivatable, or photo isomerizing group will give photo control over the activity of the enzyme. For example, an attached azobenzene may enable photo control over conformational changes necessary for the action of the enzyme, or enable the enzyme to be switched between an "on" and "off" state. This can include but is not limited to: switching between conformation states of the enzyme, switching between template dependent and template independent activity, switching between open and closed conformations of the enzyme, switching between an accessible and inaccessible substrate binding site for either incoming nucleotides or the DNA primer potentially by switching the position of a blocking group, switching between binding of a competitive inhibitor and an accessible substrate binding pocket, switching between binding of a non-competitive inhibitor and an active enzyme, and switching between steps along the catalytic cycle of the enzyme for controlled progression through the enzyme's catalytic cycle.

In some cases, the use of an orthogonal amino acid to specifically introduce a click chemistry attachment point on TdT will enable the attachment of an azobenzene moiety. The azobenzene can act on its own, or can be attached further to a blocking group that can reversibly disrupt substrate binding. Control of the azobenzene conformation by light will enable the movement or otherwise change in the blocking group that will switch the blocking group from disrupting substrate binding to permitting substrate binding, or vice versa. Thus, the enzyme could be switched between "on" and "off" states, and/or its catalytic cycle controlled.

In another embodiment of the present invention, the engineered TdT comprises a photoswitchable azobenzene derivative that is capable of cross-linking at least two amino acid residues of the TdT. One or more of these amino acid residues comprising the cross-linking azobenzene derivative may be located in the loop of the TdT protein associated with the DNA ratcheting/translocation function of the TdT (Loop 1). The cross-linking azobenzene derivative regulates or gates the translocation/ratcheting, of the TdT along the growing single-stranded polynucleotide thereby inhibiting the insertion/addition of a subsequent mononucleotide to the strand until the TdT ratcheting function is restored/re-activated. Inhibiting DNA ratcheting will prevent DNA extension. Conformational changes involved in TdT's mechanism may be controlled by azobenzene attachment to other residues involved in the conformation change, outside of Loop 1.

For example, a photoswitchable crosslink between two amino acids in the loop responsible for TdT ratcheting can provide direct control over the conformational change of the loop responsible for the DNA ratchet behavior after an incorporation event. This will enable a pause in DNA extension, and can also provide a point in the synthesis process where incorporation of the mononucleotide can be verified, for example, by fluorescence means such as FRET, quenching, or other detection means using a detectable label known to those of skill in the art.

As described above, using the structure of murine TdT, amino acids can be identified in the murine, and other homologous TdTs, that are reasonably suitable for azobenzene modification or cross-linking. One skilled in the art can also modify the TdT with the addition or deletion of one, or more, amino acid(s) that alter (e.g., enhance) the enzymatic activity of the polymerase, for example, including the insertion of stretches of suitable amino acids, or the deletion of segments, or e.g., partial loops of the enzyme where those additions or deletions alter the activity of the enzyme as desired.

For example, two sets of amino acids that can be cross-linked to provide control over the ratchet process are: D399->K403 and K387->D441 of SEQ ID NO: 1. The TdT protein can be modified either to introduce artificial amino acids at these locations to provide click reactive groups, as described above, or selenocysteine amino acids, which can be selectively introduced and targeted. The chemistry of the photoswitch would differ from that described above as it has reactive groups at both ends. Different click chemistries can be introduced at the different amino acid locations to direct the orientation of the photoswitch. For example, in the case of the selanocysteine cross-linking, methanethiosulfonyl or other suitable groups can be introduced at each end of the photoswitch molecule.

Also encompassed by the present invention is a modified azobenzene molecule specifically comprising one, or more reactive groups as described herein. The reactive groups of the azobenzene molecule can be cross-linking groups allowing the azobenzene to act as a cross-linker between two, or more, biomolecules that contain suitable reactive groups. For example, the cross-linking can trigger a conformational change(s) that can result in the modulation of enzyme activity.

In another embodiment, the reactive groups of the modified azobenzene can cross-link an engineered TdT of the present invention with a peptide. For example, the peptide can be an affinity tag (e.g., a HIS tag known to those of skill in the art), thus enabling purification of enzymes only containing azobenzene molecules. Also encompassed by the present invention are azobenzene molecules cross-linked to a peptide wherein the peptide blocks or gates the binding of a nucleotide to the active site of a DNA polymerase described herein, thus, providing an alternative method of controlling nucleotide synthesis. More particularly, the azobenzene cross-linked peptide can comprise two domains wherein one domain is a blocking domain that blocks the entry or binding of a nucleotide to the active site of the TdT and the other domain comprises an affinity domain with an affinity tag peptide.

In another example, the reactive groups of the modified azobenzene molecule can cross-link a polymerase, such as TdT, with an enzyme inhibitor that specifically inhibits the activity of a DNA polymerase. Upon breakage of the cross-linking bond, the inhibitor is removed and the polymerase activity is restored.

In yet another example, the azobenzene molecule comprises a cross-link between a polymerase and a nucleic acid (e.g., DNA) wherein the DNA is positioned within the active site of the polymerase and thus acts as an inhibitor. When the cross-link is broken, the DNA is removed and the polymerase activity is restored.

More specifically encompassed by the present invention is a composition comprising a photoswitchable azobenzene moiety, wherein the azobenzene molecule is modified and the modification comprises introduction of an attachment site for a click reactive group and/or introduction of an attachment site for an amino acid side chain.

As described herein, the photoswitch can be an azobenzene molecule with modifications to enable its attachment to the TdT protein. Modifications can include, at one or both ends of the molecule, for example, 1) an attachment point (amine or alcohol) for addition of a clickable moiety (e.g., azide, alkyne, tetrazine, norbornene, or trans-cyclooctene) and 2) an attachment point for addition of short chains of amino acids (peptides) to provide enhanced inhibition of the nucleotide entry. The peptides will enable control over the length, orientation and chemical functionality of the photoswitch. Moreover, the physical properties of the peptide side-chain can be tailored to modulate the localized polarity of the reaction medium of the photoswitch, altering the isomerization wavelengths and rates. The azobenzene molecule can be coupled to a peptide via either an amine or carboxylic acid modification, enabling the reaction with a peptide via standard coupling protocols.

The azobenzene photoswitch operates through light-mediated isomerization between cis and trans stereoisomers. The electronic properties of the azobenzene photoswitch can be tailored by modifying the substituents on the aromatic rings (e.g., use of para-electron-donating groups on one ring with para-electron donating groups on the other ring generates a push-pull system, generally increasing the rate of thermal isomerization). Tailoring the electronic properties also tailors the wavelengths of light that will trigger isomerization events, for example, introduction of electron-donating groups will red-shift the absorbance spectra of the trans-isomer.

Examples of azobenzenes with different electronic properties are shown in FIG. 2A-B. FIG. 2A depicts an azobenzene with two para electron-donating groups, which should red-shift the absorption and lead to short half-lives of the cis-isomer. An example of an azobenzene push-pull system with both a clickable moiety (azide) and peptide chain is depicted in FIG. 2B. $R^1$ and $R^2$ are independently selected from the group consisting of alkyl, substituted alkyl, acyl, cycloalkyl, substituted cycloalkyl, aryl, substituted aryl, heterocyclyl, substituted heterocyclyl, heteroaryl, and substituted heteroaryl. Optionally, $R^1$ and $R^2$ may contain moieties that allow for bioconjugation to occur either via click chemistry or by chemistries such as amidation reactions, thiol-ene reactions, or maleimides-thiol conjugations. Such moieties are referred to herein as bio-reactive moieties, or bioconjugation moieties. These moieties and methods of conjugation are well-known to those of skill in the art.

Based on the teachings described herein, other photoswitchable azobenzene molecules can be produced and tested for efficacy by one skilled in the art for use in the present invention.

Thus, as a result of the invention and its embodiments described herein, an improved, accurate and cost-effective method of in vitro polynucleotide synthesis is now available.

BRIEF DESCRIPTION OF THE DRAWINGS

FIG. 4A shows the entry of new deoxyribonucleotide triphosphate (formation of pre-catalytic state). 1.1 shows the binding of new nucleotide into the active site of TdT, the nucleotide is coordinated by a metal ion (metal B). 1.2 shows the binding of Metal A into the active site activates the 3'OH of the extending strand and creates the assembled active site capable of addition of the incoming nucleotide, Leu 398 is in position to force the 3'nucleotide into position to attack the incoming base.

FIG. 4B shows the nucleotide addition and metal release (formation of post-catalytic state. 2.1 shows that the 3'OH of the extending DNA attacks the triphosphate, resulting in a new phosphodiester bond. 2.2 shows that the released pyrophosphate and coordinating metal B are released from the active site. 2.3 shows that Metal A is released from the active site or translocates to metal C binding site. 2.4 shows the movement of Metal A drives a conformational change in TdA-DT resulting in the movement of Loop 1, and Leu 398 flips out from its intercalating position allowing strand translocation.

FIG. 4C shows the strand translocation. 3.1 shows that after the DNA strand is permitted to translocate such that the active site is recreated, metal is removed, either released by the enzyme or translocated internally. 3.2 shows that Loop 1 undergoes the reverse conformational change, and Leu 398 returns to position intercalating between bases in the extending DNA strand.

FIG. 4D shows the return to competent state of the enzyme. 4.1 shows that the enzyme is returned to the competent state of 1.1, as the next nucleotide enters the active site for elongation.

FIG. 5A-D show conformational changes in the TdT enzyme during DNA synthesis.

FIG. 10 A-E show the amino acid sequences of murine TdT (SEQ ID NO:1); bovine TdT (SEQ ID NO:2); human (SEQ ID NO:3); shark (SEQ ID NO:4) and the catalytic core of murine TdT (SEQ ID NO:5).

FIG. 11 shows the amino acid sequence alignment for murine, human, bovine and shark TdT.

FIG. 13A-B is a depiction of potential methods by which a photo-activatable cross-linker, incorporated into the enzyme's structure, could render photo-control over the enzyme's catalytic cycle. In the images shown, an azobenzene moiety crosslinks loop 1 either to another residue in the protein backbone (FIG. 13A) or to itself (FIG. 13B), enabling the photo-control of the conformational change in loop 1. Such photo-control would enable the activity of TdT to be modulated, enabling new controlled DNA synthesis techniques.

FIG. 14A-B show potential methods by which the catalytic cycle of TDT may be controlled via addition of a photo-isomerizable moiety capable of reversibly blocking the active site. Potential attachment points include Loop 2 of the enzyme (FIG. 14A), or areas on the protein backbone suitable for active site blocking (FIG. 14B). The blocking group may act as a competitive inhibitor, reversibly preventing nucleotide binding to the active site of the enzyme. The blocking group may be composed of a range of chemical groups, including but not limited to peptides, nucleic acids, known competitive inhibitors of TdT, PEGs, DNA, and other bulky chemical groups capable of preventing nucleotide binding.

DETAILED DESCRIPTION OF THE PREFERRED EMBODIMENTS

The Catalytic Cycle of Terminal Deoxynucleotidyl Transferase

There are distinct steps along the catalytic cycle of TdT. The enzyme has 2 major activities during in vitro non-templated DNA synthesis: transferring nucleotides onto the 3-prime end of a growing DNA strand, and "ratcheting" down the strand of DNA in order to position the active site such that the next nucleotide can be added. (See for example, Gouge, Jérôme, et al. "Structures of intermediates along the catalytic cycle of terminal deoxynucleotidyl transferase: dynamical aspects of the two-metal ion mechanism." J. Mol. Biol. (2013) 425, 4334-4352).

The methods described herein make use of these discrete activities, and thus provide the means to engineer the enzyme, or the conditions around the enzyme, such that only one of these activities can occur at a time, therefore preventing the addition of multiple bases without outside influence.

Metal Ion Binding and Release and the Catalytic Steps

The catalytic cycle of TdT is driven largely by the binding and release of the two metal ions necessary for the activity of the enzyme. These metal ions are expected to be Magnesium in vivo, but can be replaced with Cobalt, Manganese, or Zinc in vitro, each with varying effects on the activity of TdT. Specifically, it has been described that addition of Zinc increases the addition of pyrimidines, Manganese and Magnesium have higher rates of addition of purines, and Cobalt has more versatility, playing the role of both Magnesium of Zinc, and is therefore commonly used in in vitro experiments.

Figure 1:
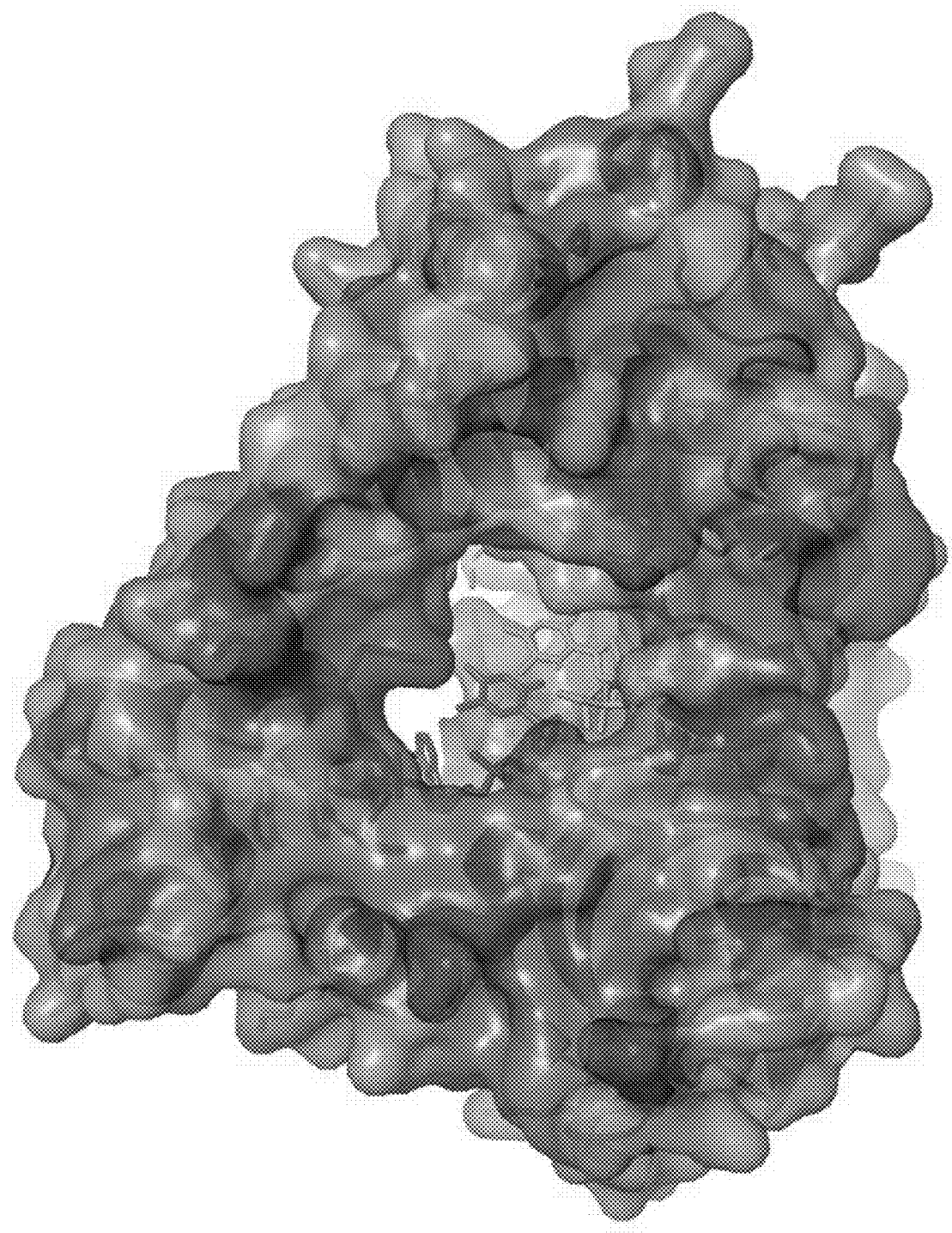
FIG. 1 is a molecular model of mTdT generated from PDB 4i27 [1]. Residues that are surface-exposed with 30 square angstroms of solvent-exposed surface are shown in orange and red. The subset shown in red are residues that are examples of residues that could be used for control of nucleotide entry via attachment of a photo-controlled inhibitor or steric blocking group. Incoming nucleotide is shown in teal. The elongating DNA primer is shown in dark blue.
Figures 2A, 2B:
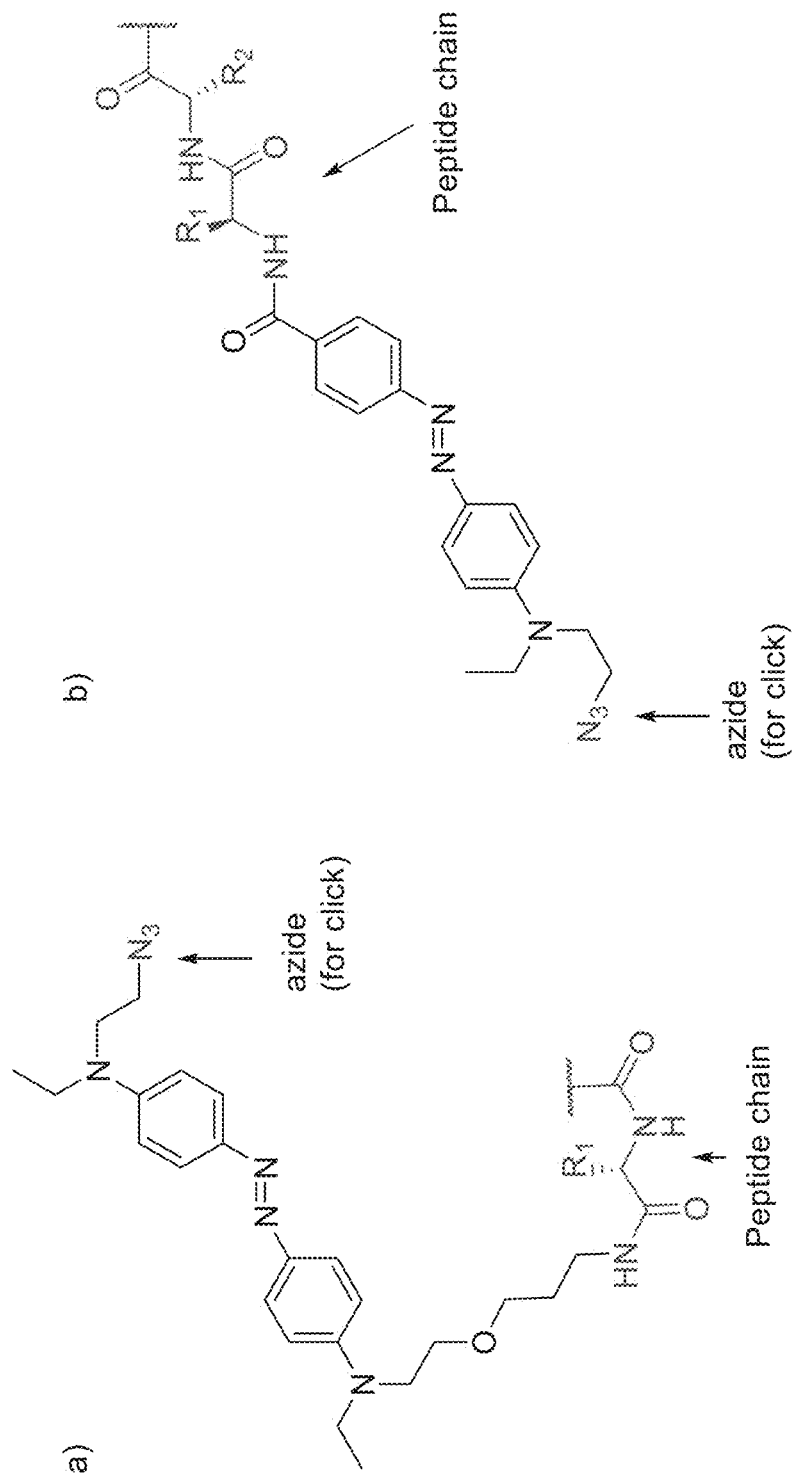
FIG. 2 A-B depict structures exemplifying a modified azobenzene molecule with substituent groups suitable for bioconjugation.
Figure 3:
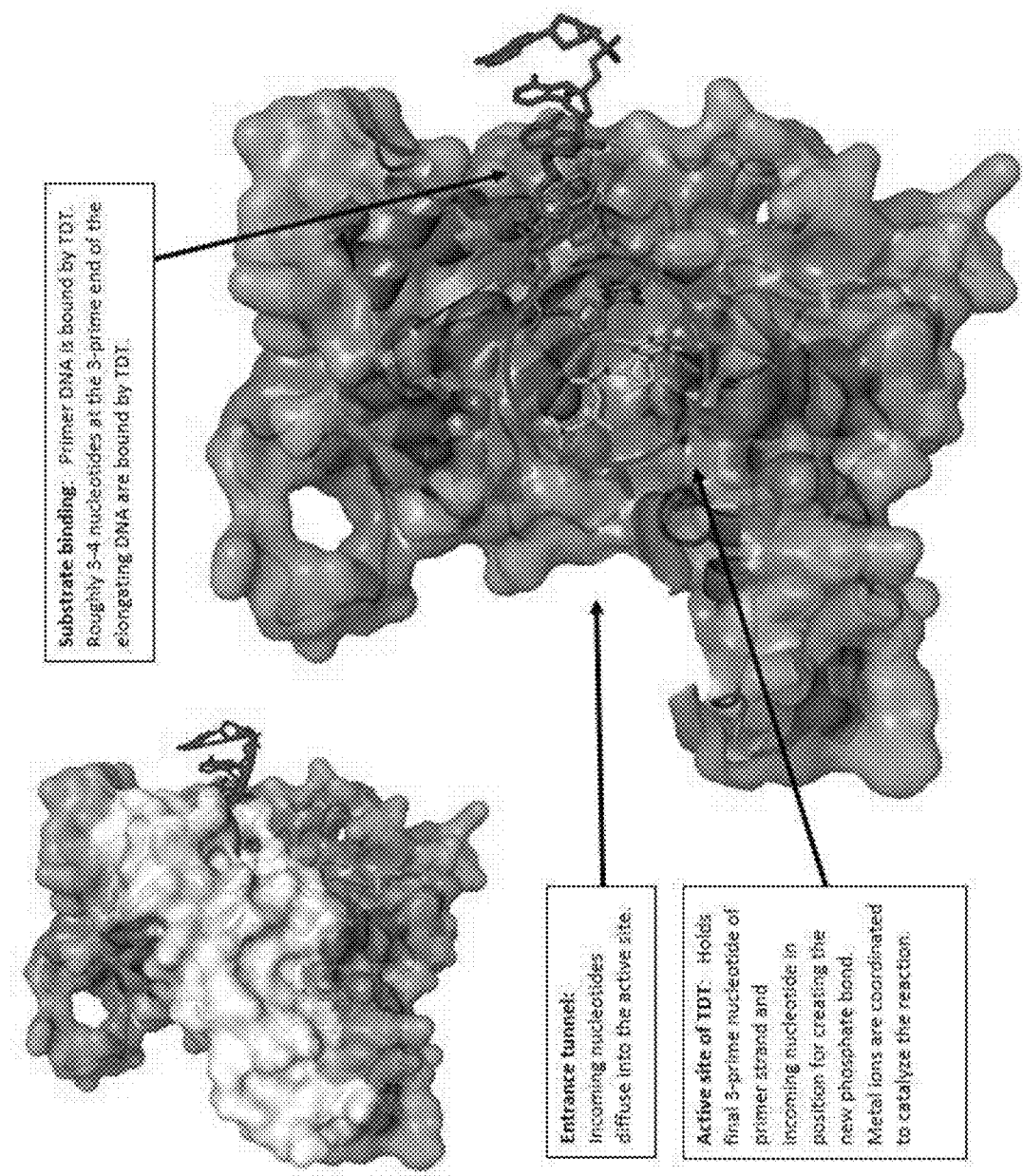
FIG. 3 depicts a view of the structure of mTdT. Top left: mTdT enzyme PDB 4i27, shown in white is a section of the protein removed in the subsequent structure (bottom right) in order to give a cross-sectional view of the mTdT active site. Indicated by arrows are the Entrance Tunnel, where incoming nucleotides diffuse into the active site, the DNA Substrate-Binding portion of TdT, where the 3-prime end of the elongating DNA strand is bound by TDT, and the Active Site of mTdT, where the addition of dNTPs to the 3-prime end of the DNA strand is catalyzed.
Figure 4A:
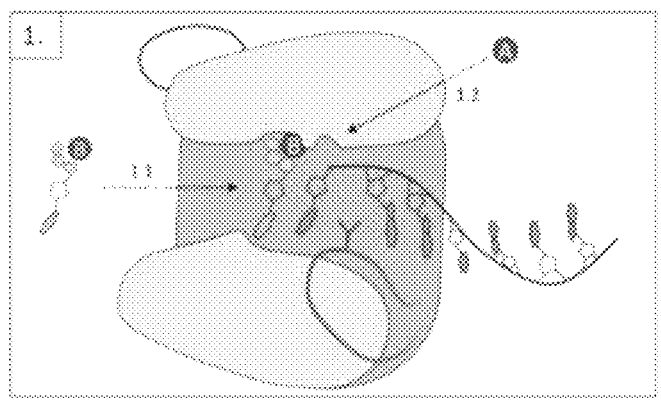
FIG. 4A-D is a graphic depicting the TdT catalytic mechanism. (The catalytic cycle and enzyme structure steps depicted herein are based on the description of ref. [1]).
Figure 4B:
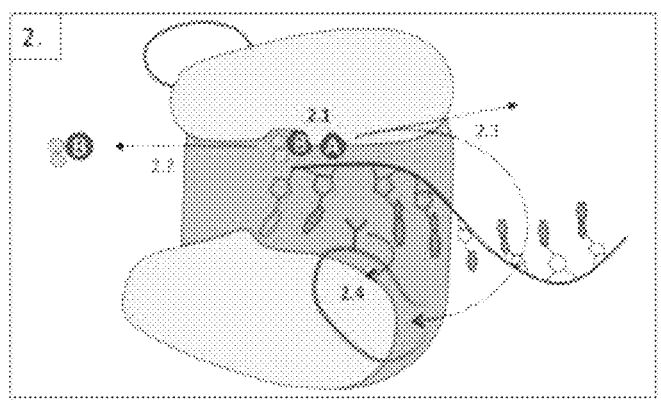
Figure 4C:
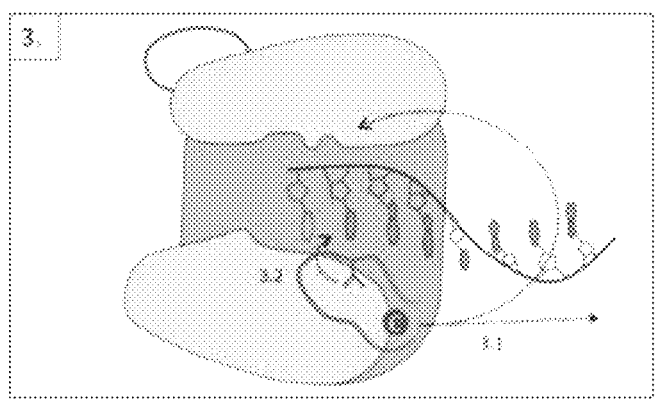
Figure 4D:
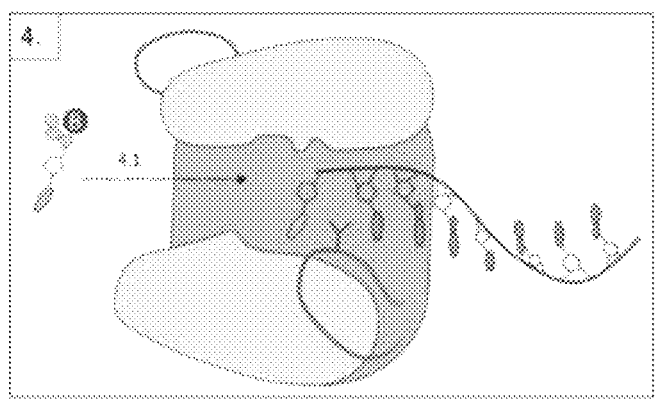
Figure 6:
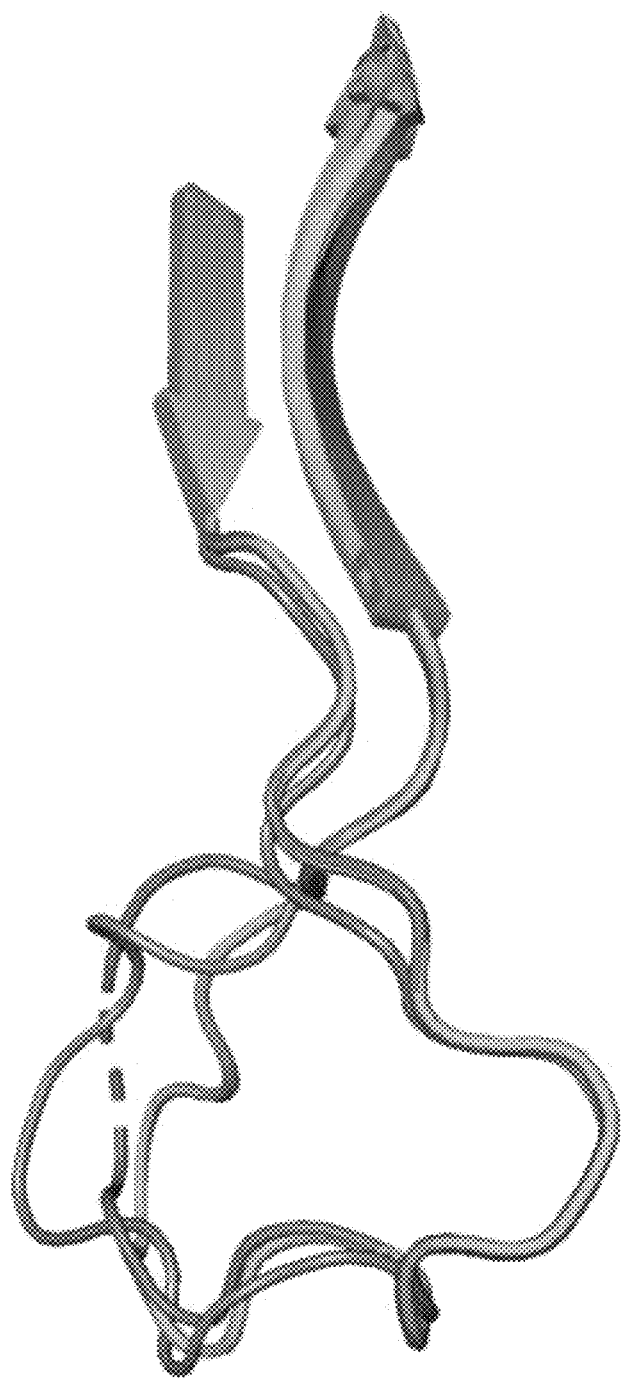
FIG. 6 is a graphic depicting TdT loop 1, positions 382-401, and the adjacent beta sheets 3 and 4. In teal and green are PDB structures 4i2b and 4i2f, in light purple is PDB 4i29, and in dark purple is PDB 1jms [1,2]. Each structure is believed to represent a different step along the catalytic cycle of TDT. The obvious major conformational changes in Loop 1 are an example of locations that may be of interest for engineering towards control of TdT's catalytic cycle.

TdT's activity begins with binding a template strand, which is a process that is not dependent on the presence of metal ions, and is likely done via 3d diffusion, as TdT does not seem to have DNA-scanning activity. Next, an incoming nucleotide can bind into the active site. (FIG. 3) Metal B accompanies the binding of an incoming nucleotide, as it is necessary for stabilizing the triphosphate and thus promoting binding of the nucleotide triphosphate to the enzyme. Metal B promotes the binding of the next added base, but is not the catalytic metal. Metal A binding is necessary for the catalytic step. (FIG. 4)

The next step of the catalytic cycle is that the protein undergoes a conformational change such that Leucine 398 flips up intercalating between the last nucleotide on the 3-prime end of the primer strand and the rest of the strand. This step may occur before or after the binding of the incoming nucleotide. This positions the final nucleotide into a position such that the 3-prime hydroxyl group is capable of carrying out nucleophilic attack on the phosphate of the incoming nucleotide in order to add the next base. The next step is for Metal A (the second metal) to bind to the active site, activating the three prime hydroxyl group for nucleophilic attack on the phosphate of the incoming nucleotide, thus catalyzing the addition of a nucleotide to the end of the growing DNA strand. Metal B is released with the pyrophosphate as Histidine 342 rotamers away from the metal B site. This completes the chemical step of the enzyme's catalytic cycle.

At this point, the enzyme has incorporated/added a single nucleotide, but cannot yet incorporate a second nucleotide, as the translocation step must occur to reveal the active site once again. The translocation step involves the movement of the enzyme one base down the strand of DNA, such that it is in position once again to incorporate a base onto the 3-prime end of the growing DNA chain.

Metal A binds transiently to the Metal A binding site, and its release from the Metal A site is necessary for translocation, and perhaps powers the translocation step that returns the enzyme to the competent state. Metal A may simply be released and diffuse away from the enzyme, or it may, as is put forth by Gouge, Jérôme, et al., move internally (within the enzyme) to another putative metal binding site called Metal site C. The dissociation, or movement, of Metal A, drives and allows a conformational change in the protein, specifically in Loop 1 (which includes SDR1 and SDR2 sites).

This conformation change is responsible for the ratcheting mechanism. After ratcheting down the primer strand by one base, the Metal is released from site C and can return to site A (but does not have to be there for nucleotide binding). Finally, Leucine 398 can flip up into the position in which it forces the final nucleotide in the DNA primer out of its typical stacking conformation with the rest of the primer and into the active site, and the next nucleotide triphosphate can enter the active site with metal B. Again, these two actions may happen in either order. The result however is a return to the competent state, the cycle is complete, and TDT may incorporate the next base. TDT has some processivity, capable of adding hundreds of nucleotides to a growing strand. The rate of insertion of nucleotides is largely dependent on the type and concentration of metal present, and the type and concentration of nucleotides present. (see FIG. 5A-D as shown in Gouge, et al. J. Mol. Biol. (2013) 425 at p. 4347).

Conformation Changes in the Protein

The conformational changes in the protein that constitute the ratcheting mechanism referred to above are believed to be driven by metal binding and dissociation, and allow TdT to translocate the DNA primer by one nucleotide such that the enzyme-DNA complex is returned to the competent state. Loop 1 undergoes a conformational change in response to the dissociation of Metal A from site A, and putative movement of Metal A to site C. Loop 1 is composed of SDR 1 and SDR 2, which include a number of catalytically critical residues that are highly conserved between species. Mutants of these residues often result in enzymes with highly decreased catalytic activity, some of which with interesting properties that will be discussed further. The residues exist as rotamers that rotate upon the conformational change. The Loop itself inserts into the primer strand with Leucine 398, and upon conformational change pulls out of this insertion, allowing the primer strand to shift before the loop is reinserted into the primer strand, locking it once again in place for attack on the next incoming nucleotide. Thus, the movement of this loop is directly responsible for the translocation of the DNA, and the return of the Enzyme to a position in which the next base can enter the active site.

Methodologies of Controlling the Catalytic Cycle for Single Nucleotide Insertion This catalytic cycle provides a number of steps at which the enzyme can be engineered such that only a single base can be controllably inserted at a time. The first is that nucleotide binding can be separated from nucleotide incorporation, as metal A must bind for incorporation, but is not required for nucleotide binding. Thus, methods by which nucleotides are bound, but not inserted, until an exogenous action is taken on the enzyme or enzyme's environment, allow TdT to be engineered such that a single base will be inserted at a time. These methods will focus on ways in which Metal B and Metal A binding can be separated, such that the binding of metal B occurs under conditions different from the conditions under which metal A binds. This same approach can be taken towards Metal A and Metal C sites, for the next step of translocation. Methods aimed to separate the binding of Metal A and Metal C, such that these processes occur under different conditions, will also yield an enzyme capable of only inserting a single nucleotide until exogenous action has been taken. Finally, methods by which the conformational change of TdT can be controlled will also yield an enzyme that is capable of single insertions. Therefore methods by which the conformational change can be prevented from occurring, or forced to occur under specific conditions will be examined. In other words, controllably trapping the enzyme in one of the stages of its catalytic cycle will allow the controlled addition of single nucleotides.

Steps of the Catalytic Cycle that can be Engineered (FIG. 4A-D)

1. After an incoming base has bound the active site, a binding of metal A catalyzes insertion of next base
2. Metal A leaving/transfer to site C causes a conformational shift in the enzyme
3. The DNA strand translocates up by one base, the conformational shift is righted, and metal leaves site c, perhaps transferring back to site A
4. The next nucleotide binds the active site, accompanied by Metal B Metallic Control of TdT (Control of Catalytic Steps)

The following section will discuss general methods by which the wildtype TdT, or a mutant version thereof, could be controlled for metal binding, thus controlling the catalytic cycle of TdT such that single nucleotide insertion may be achieved.

Control of Wildtype TdT

Methods will focus on the separation of metal ion binding to sites A and B or sites A and C. If binding to one site occurs under conditions that do not allow metal binding to another site, then it will be possible to control the enzyme's catalytic mechanism precisely such that only a single nucleotide is added at a time.

Metal Ion Concentration

The concentration of metals may be controlled such that there is sufficient metal for nucleotide binding, but insufficient metal for the catalytic step, thus allowing excess nucleotide to be removed from the enzyme's surroundings before metal concentration is spiked allowing the catalytic step to ensue, and the cycle to complete.

Figure 7:
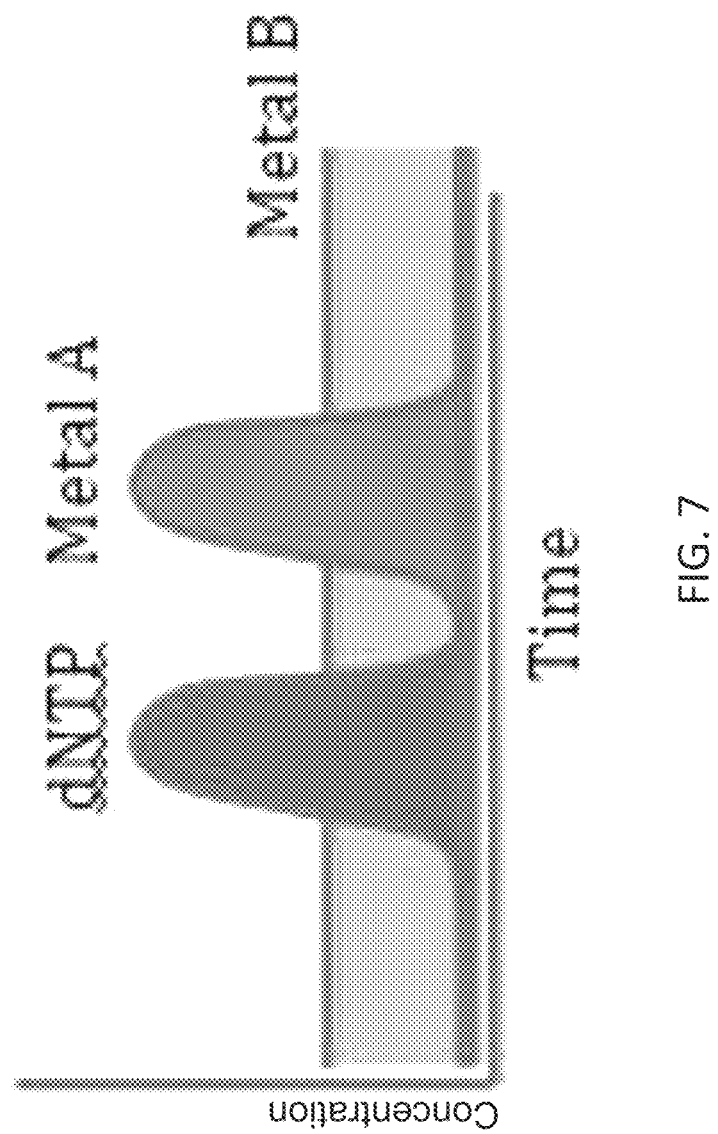
FIG. 7 is a graph showing the concentration of metals used to control TdT catalysis.
Figure 8:
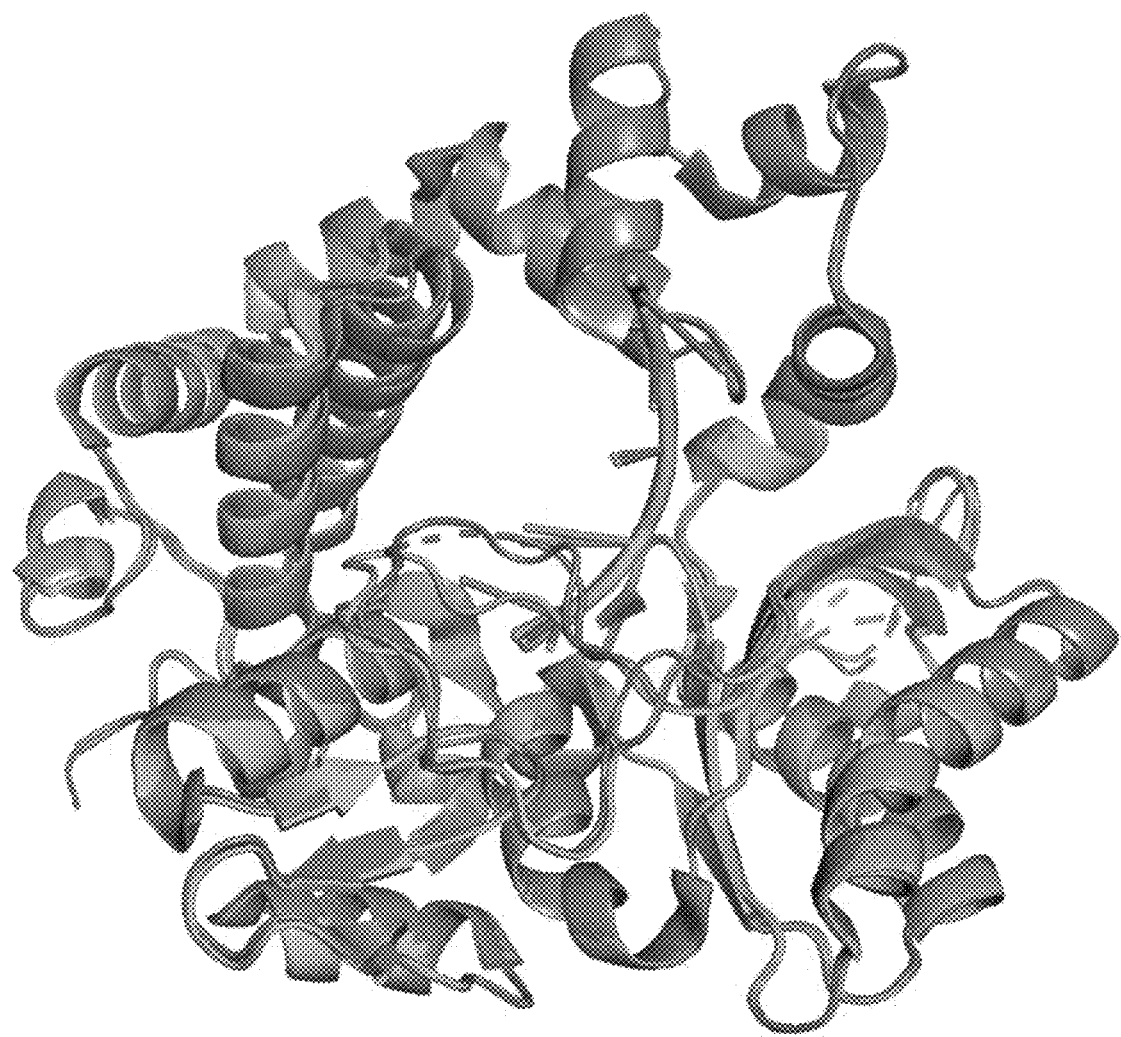
FIG. 8 depicts the global alignment of mTdT under varying crystallization conditions intended to capture mTdT at different steps along its catalytic cycle. In teal and green are PDB structures 4i2b and 4i2f, in light purple is PDB 4i29, and in dark purple is PDB 1jms [1,2]. Residues undergoing conformational changes, and residues that are disordered, represent residues that may be of the greatest interest for engineering in order to control the catalytic cycle of TdT.
Figure 9:
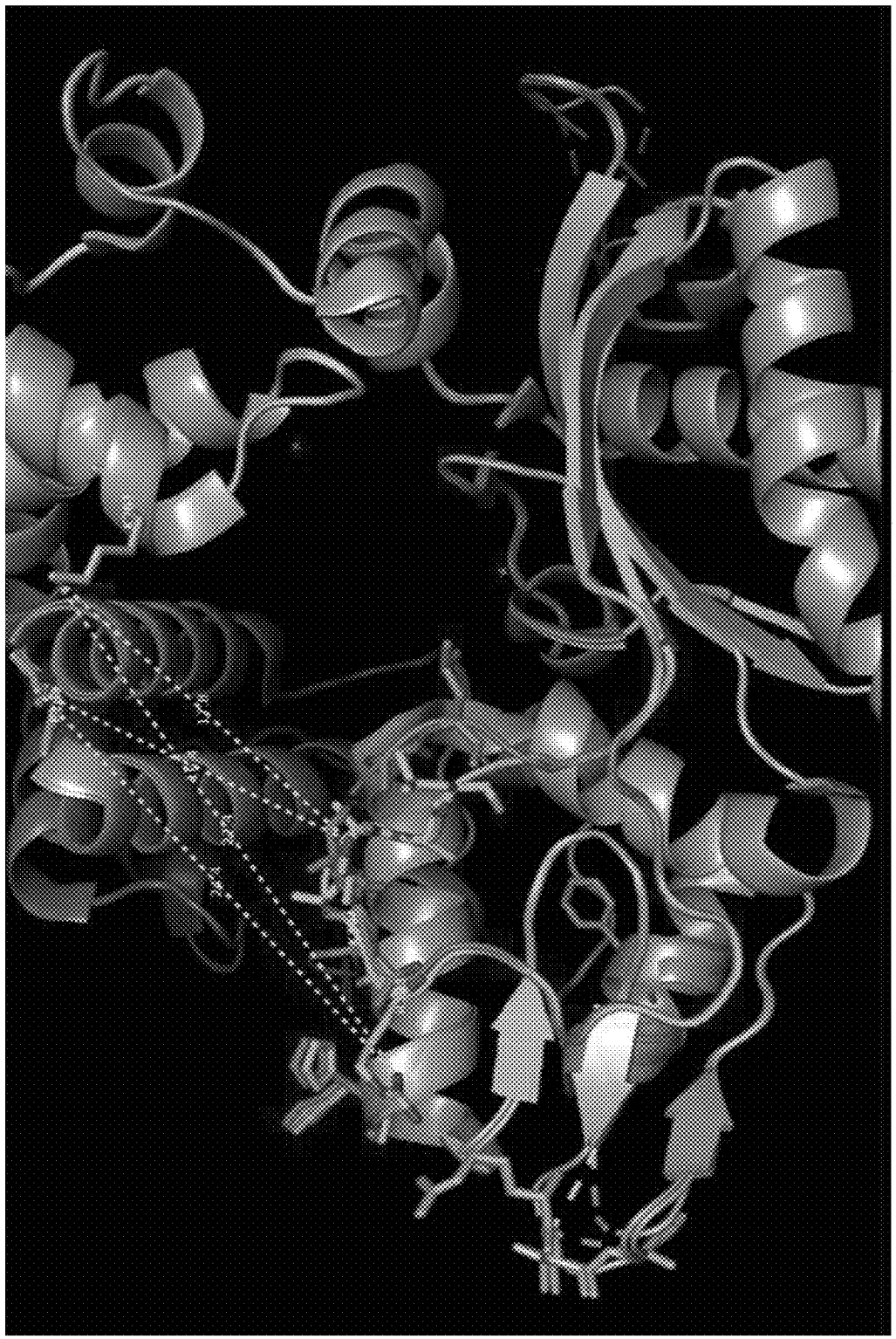
FIG. 9 depicts the Global alignment of murine TDT at different steps in the catalytic cycle. In teal and green are PDB structures 4i2b and 4i2f depicting the translocation step, and in purple is PDB 4i29 depicting the pre-catalytic state, each colored only for loop 1 [1]. Dotted yellow lines show measurements for the distances between: residues on the loop that are prime for crosslinking, and have conformational changes between these catalytic steps, and residues that are on the backbone of the enzyme, and do not undergo conformational change. The distances for crosslinking are given in angstroms. Such crosslinking could enable the specific photo-control of conformation changes in Loop 1. These are examples of cross-linkable residues that could enable photo-control; there are many suitable residues and possible combinations of residues that could achieve the same result.TdT.

In a microfluidic chip, wherein the DNA to be extended, or TdT itself is immobilized, fluid flow through the chip can be used to control the concentration of metal ions, dNTPs and other reaction components at the site of extension. Thus, careful control of metal ion concentration, and other reagents, can allow control of the catalytic cycle of TdT. (FIG. 7).

Use of Different Metal Ions

Mg, Mn, Zn, Ni, and Co may favor binding to each of the different metal binding sites of the protein, or another metal ion may be able to bind and have activity in only one of the sites. Therefore the type of metal ion present may be enough to allow one step in the catalytic cycle to initiate while not allowing the full cycle to complete. For example, metals that have activity for site B but not site A, could be used to allow dNTP binding to the active site pocket. Once bound, excess dNTP could be washed away and Metal A spiked in to promote catalytic addition of the incoming nucleotide, and single nucleotide addition would be achieved. As long as a significant difference in rate between steps in the catalytic cycle is achieved, it will be possible to incorporate only a single nucleotide.

Use of Chelators

Chelators that specifically target one type of metal ion, that can strip metals from one binding site but not another, or simply used to precisely control the availability of metal ions to the TdT enzyme, may have the ability to significantly affect the rates of each of the steps along the catalytic cycle, or allow one step to ensue while preventing a subsequent step in the catalytic cycle. Thus, they may be used to control the enzyme's activity in order to achieve single nucleotide addition.

Use of Electrodes to Control Accessibility of Metal Ions

The microfluidic chip's flow-based control of reaction component concentrations offers a good method for controlling the accessibility of reagents to the enzyme. However electrodes can control the accessibility of metal ions to the enzyme as well. This gives another method of controlling metal ion concentration, that is perhaps more scalable and gives tighter control over local metal ion concentrations.

Use of pH to Control Metal Ion Binding

It is reasonable to promote metal ion binding to one site over another site by carefully controlling the pH of the enzyme's environment. Differences in the isoelectric point of specific residues could make a certain pH suitable for metal binding at one of the metal binding sites, but not another, if a previously negatively charged side chain that took part in the chelation of a metal ion becomes uncharged at a lower pH. Therefore pH modulation could be used to prevent the addition of multiple nucleotides.

SUMMARY

All these methods, combined or used individually, are options for controlling the catalytic cycle of TdT. However, modification made to the structure of TdT, by amino acid substitutions, protein engineering, and/or chemical or structural modifications to the enzyme, may generate mutants or versions of TdT that are controllable by these same methods.

Control of Mutant or Modified TdT

The TdT enzyme may be mutated or altered such that the enzyme is more susceptible to the types of control previously described for wildtype TdT. Modifications made to make the enzyme responsive to certain conditions, to make the enzyme incapable of proceeding through the catalytic cycle without outside influence, and to make the enzyme more easily controlled by modulation of the metal ions accessible to it, will generate an engineered TdT capable of single nucleotide insertion, and thus accurate and efficient DNA synthesis.

Metal Specificity of Binding Sites

Enzyme engineering, including but not limited to making point mutations to the amino acid sequence of TdT, can render one or more of the metal binding pockets capable of using only certain metal ions. This can be used to give control over TdT's catalytic cycle, by making certain steps require the addition of metal ions that are otherwise not present.

For example, if metal binding site A is mutated such that it can no longer accept magnesium, but must use cobalt, manganese, or nickel, and the other metal binding sites are left such that they are fully capable of using magnesium, then the enzyme will be modified such that a single nucleotide insertion is possible. Nucleotide binding can be carried out in the presence of magnesium, allowing a single nucleotide to bind to the active site with the accompanying magnesium metal B. However, the nucleotide cannot be added to the growing chain as metal A has not yet bound to catalyze the addition of the incoming nucleotide (magnesium cannot serve as metal A as it cannot bind to the metal A site). Therefore, excess nucleotide can be removed from the microfluidic chamber before a metal capable of acting as metal A, such as cobalt, is introduced to the microfluidic chamber. Thus single-nucleotide insertion is achievable, simply by controlling the concentration or accessibility of different metal ions.

pH Control

Mutagenesis of the amino acid sequence of TdT can also generate mutant versions of TdT that are capable of only binding metal ions at a specific pH for certain metal binding sites. For example, residues involved in the metal A site that are typically negatively charged at neutral pH such as Aspartate could be mutated or altered to residues that are neutral at neutral or acidic pH, but negatively charged at a higher pH. Thus, nucleotide binding can occur at a lower pH at which catalysis cannot occur as Metal A cannot bind to the enzyme. Then, unbound nucleotides can be washed from the enzyme before the pH is raised, and Metal A binds causing the catalytic cycle to continue, and a single base to be inserted.

Control of the Ratcheting Mechanism

Besides controlling the accessibility and binding of metal ions, the ratcheting mechanism and catalytic cycle of TdT can also be controlled by controlling the ability of the enzyme to undergo conformational changes. This can be done simply through point mutants or engineered versions of TdT for which the conformational changes are no longer efficient, and therefore the enzyme is either incapable, or very slow, at ratcheting down the DNA strand to insert the next base. Or, more complicated engineering strategies, such as molecular staples of the protein backbone that undergo conformational change in the presence of specific wavelengths of light, could be used to give more complete, precise, and local control of the ratcheting of TdT. The native rate of nucleotide addition for TdT can be quite fast, reaching rates of greater than 100 nt/minute. If switching mechanisms for enzymatic control are too slow to enable individually-gated nucleotide additions, the enzyme may need to be modified to slow down the rate of incorporation. Amino acid substitutions in TdT such as D399A, K403R, C438T, and D473A to slow down the enzyme can be combined with other mutations to attach photoswitches or enable enzyme control through the other methodologies detailed below.

Interrupted Ratcheting

Generation of a mutant or engineered TdT that is incapable of efficiently adding more than a single nucleotide at a time is an engineering strategy that can yield an enzyme suitable for DNA synthesis. Point mutants such as mTdT (mouse TdT) D399A have been shown to have significantly decreased activity, and it is postulated that this is due to an interruption in the DNA ratcheting mechanism. This mutant likely adds a single base before pausing for periods of time, until the enzyme can fall off the DNA primer, can shift down the strand by thermal fluctuations, or can ratchet by its typical mechanism, albeit much less efficiently. Mutants that interrupt the conformational change, either by disrupting the protein domains responsible for the conformational change itself, or mutants of the Metal C binding site, may also be controlled exogenously for single nucleotide insertion. For example, enzymes with an interrupted ratcheting mechanism could be controlled by adjusting the temperature of the reaction, or the concentration of reaction reagents such as metal ions, or by denaturing the enzyme to replace it with a new enzyme. Alternatively mutants of the metal C binding site may have controllable activity via metal ion concentration and the addition of chelators.

Control of Conformation

Mutant versions of TdT, or perhaps wildtype TdT itself, may be able to be controlled by modulating temperature, pH, light, or another aspect of the enzyme's environment, if that factor is able to induce a conformational change in the enzyme in order to pause the enzyme at specific steps in the catalytic cycle.

pH, Heat, or Other Exogenous Control of Protein Conformation

Protein engineering of TdT can yield mutant versions that have inducible conformation changes in response to shifts in pH, heat, or an exogenous chemical. This can be done through point mutagenesis to yield mutant TdT enzymes with pH, heat, or chemical, dependent activity. Alternatively, it may be done through the addition of protein domains that are responsive to exogenous control, such as over protein conformation. Such enzymes could allow the insertion of a single nucleotide, but would prevent ratcheting to allow a second nucleotide into the active site of the enzyme. Some outside action would be required in order to allow ratcheting, or another means, to return TdT to the position in which it can insert another base. However, before allowing or causing ratcheting to occur, excess dNTP would be removed from the area surrounding the enzyme, and thus single nucleotide addition would be achieved.

Photo-Activated Switches in Conformation

One method of exogenous control of protein conformation would be the use of a photo-activatable change in conformation. This may be done through the addition of protein domains that are responsive to exogenous control, such as the CRY2-CIB1 blue-light responsive domains (or versions thereof), that could be used to give exogenous control over protein conformation. Alternatively, a particularly intriguing method can be the use of a photo-activated staple in the protein backbone. For example, an azobenzene photoswitch staple switches from trans to cis in the presence of UV light, and back to trans in the presence of visible light or heat. By stapling two parts of the protein backbone responsible for the change in protein conformation, such that the protein conformation change is directly linked to the change in conformation of the photoactivatable staple, the conformation of the protein could be directly controlled by light and/or heat. Thus, the enzyme, after inserting a single base, could be locked in a non-ratcheting conformation while excess dNTPs are removed from the microfluidic device until a light signal is used to induce conformation change and force the enzyme through the rest of the catalytic cycle. In this manner, nucleotides can also be excluded from the enzyme's active site if desired. This gives greater spatial and temporal control over the enzyme's activity. This enzyme may be suitable for arrayed synthesis of DNA strands by light-control of specific nucleotide incorporation, where many DNA strands of different sequence can be synthesized in parallel.

Blocked dNTP Binding

The methods described deal with control of the catalytic cycle of TdT. They may be used individually, or in combination to yield a system by which dNTP incorporation may be controlled. However, there are other possible methods of enzyme engineering, less related to the catalytic cycle, and more related to the acceptance of an incoming nucleotide, that may be used individually or in combination with the previously described methods to give greater control over the enzyme's activity. One method of protein engineering, would be to design versions of TdT with a reversibly, or irreversibly, blocked nucleotide entrance tunnel, that may be used to help ensure single nucleotide addition.

Irreversible Blocking of Nucleotide Entrance Tunnel

Irreversibly blocked entrance tunnels for TdT could enable a synthesis strategy whereby TdT is initially bound to a nucleotide, and then used as a reagent for the attachment of single nucleotides to a growing DNA, and washed off by denaturing conditions. Thus, the modified TdT enzymes would become single-use, incorporating a single nucleotide before being denatured and removed.

Reversible Blocking of Nucleotide Entrance Tunnel

Reversibly blocked entrance tunnels (be it by protein engineering, by an exogenous factor added to the solution, etc.) can enable greater control over single nucleotide incorporation. In one scenario, a reversibly blocked TdT is used in conjunction with metal ion gating in order to give greater spatial and temporal control over DNA synthesis. In this scenario, metal gating is used to control the addition of an incoming nucleotide as previously described; nucleotide binding occurs under conditions separate from nucleotide addition. However, an addition level of control is added, as nucleotide binding can now be controlled as well via the reversibly blocked entrance tunnel. Now nucleotide binding to the pocket can be gated, such that a single nucleotide is allowed to enter and bind to the active site, but cannot be incorporated due to metal ion constraints, and the nucleotide is sealed into the active site while excess nucleotide is removed from the surrounding solution. The bound nucleotide can be added by introduction of the catalytically necessary metal (or conditions), and the cycle can continue. In this method, nucleotides can also be excluded from the enzyme's active site if desired, similarly to the gated ratcheting engineering methods previously discussed such as the azobenzene photo-switching molecular staple previously described. Thus, again the specific control over nucleotide binding can yield an enzyme capable of being used in an array format to synthesize multiple strands of DNA with different sequences at once.

One reasonable engineering method for generating such an enzyme is to engineer the protein with a new domain that is capable of blocking the nucleotide entrance tunnel under certain conditions. For example, use of the CRY2-CIB1 blue-light responsive domains (or versions thereof), could give optical control over TDT's nucleotide binding activity, thus giving tight control over the enzyme's addition of nucleotides. In this scenario, blue light would cause the localization of two protein domains, which would be engineered to close up the nucleotide entrance tunnel. Therefore, in the presence of blue light, nucleotides would not be able to bind or escape from the active site of the enzyme.

Assays Used to Select for Engineered Enzymes

The following section describes potential assays that can be used to select and identify engineered TdT enzymes with particular activity that is controllable for single nucleotide insertions.

General assay for a single nucleotide insertion:

Mass spec can be used in a 96 well format for analysis of extension products. Mass spec should be able to differentiate between no insertion products, single insertions products, and multiple insertion products. This method may be the simplest available analysis method, and is scalable and sensitive.

The addition of a single nucleotide can also be linked to a new functionality of a DNA molecule, which would aid in its detection. For example, conjugates of the nucleotide to another chemical group such as biotin, fluorophores, etc. can aid in the detection of extended products. Finally, an extended nucleotide can make a PCR reaction previously impossible possible, if, for example, now a 3-prime end of a primer can anneal and initiate synthesis. However, recognizing a single insertion as opposed to multiple insertions may be difficult in these cases.

Alternatively, the addition of a single nucleotide can impart genetic functionality on a DNA substrate such that no insertion, or multiple insertions do not impart that same functionality. This assay has the potential to be very sensitive. For example, a compartmentalized pool of engineered TdT enzymes can be screened for single nucleotide insertions. An immobilized DNA primer that contains the reverse complement of a reporter protein up to the last base of a start codon (but not containing the first two) is acted upon by the pool of TdT enzymes. Addition of a single nucleotide, and subsequent splinted ligation with a DNA containing a promoter region for t7 RNA polymerase, yields an active genetic DNA component capable of generating a reporter protein only when a single nucleotide is added to the DNA primer. Thus, the single nucleotide addition activity can be probed for very sensitively.

Metal Ion Specificity

In order to engineer versions of TdT with altered metal binding sites such that there is greater specificity for the required metal ion, an assay can be developed to determine if an engineered enzyme has the desired properties. One assay that can be tested in bulk reactions is to determine if an engineered enzyme now has greater metal ion selectivity. If the engineered enzyme cannot function in the presence of one metal ion (that it was engineered to not be able to use for one of the metal binding sites) but can work in the presence of other metal ions, then it will likely have the desired properties for an engineered enzyme. It is not necessary in this case to verify the ability to incorporate single nucleotides in bulk, multiple insertions will be perfectly expected when the correct metal ions are present.

The test to determine this enzyme's ability to incorporate single nucleotides will be a microfluidic-based assay, in which metal ion type and concentration is controlled to attempt to achieve single-molecule insertions. The extension products are analyzed by sequencing in order to determine the effectiveness of single-nucleotide control, for each of the dNTPs, under varying conditions.

pH, Heat, or Other Exogenous Control of Metal Binding or Conformation

For engineered versions of TdT whose activity requires fluctuations in heat, pH, exogenous factors, etc., over the course of the reaction, another assay will be necessary. Versions of the engineered enzyme will be screened first for a lack of activity under conditions intended to cause pausing at some step in the cycle. Once inhibited versions are identified, or conditions that result in inhibition are identified, (the conditions and the enzyme may be engineered towards each other), then the remaining enzymes will be screened for those that possess activity under another condition, or can be controlled through their catalytic cycle, resulting in successful addition of nucleotides.

As described herein, these assays will identify good candidates, but in order to assess this enzyme's ability to incorporate single nucleotides, microfluidic control of single nucleotide insertions and verification by sequencing will be necessary.

EXAMPLES

The invention will be further described with reference to the following non-limiting examples. The teachings of all the patents, patent applications and all other publications and their websites cited in the examples and elsewhere herein are incorporated by reference in their entirety.

Methods for Optically Controlling DNA Sequence by Gating an Engineered Enzyme

Example 1. Gating Synthesis by Using a Photo-Controlled Inhibitor

This method requires an engineered enzyme that has been modified with an azobenzene derivative or other photoswitchable molecule enabling the gating of nucleotide entry into the active site of the enzyme. A suitable system or device enabling the introduction and flushing of reactants and the optical stimulation of the enzyme is also required.

I. TdT is incubated with a template (seed) DNA strand to enable TdT association with seed DNA substrate.

II. The first nucleotide in the desired DNA sequence is introduced into the reaction chamber. The nucleotides can either be added with additional TdT or without.

III. The enzyme is illuminated at the wavelength required to switch an azobenzene molecule, from the trans to the cis configuration. For thermally fast relaxing "push-pull" azobenzenes, this wavelength will be in the blue range, at about 450 nm, for example. Azobenzene molecules that have not been modified for fast relaxation require illumination at about, for example, about 320 nm. The change in configuration of the azobenzene unblocks the entrance of the enzyme enabling the entrance of a nucleotide into the active site.

Figure 26:
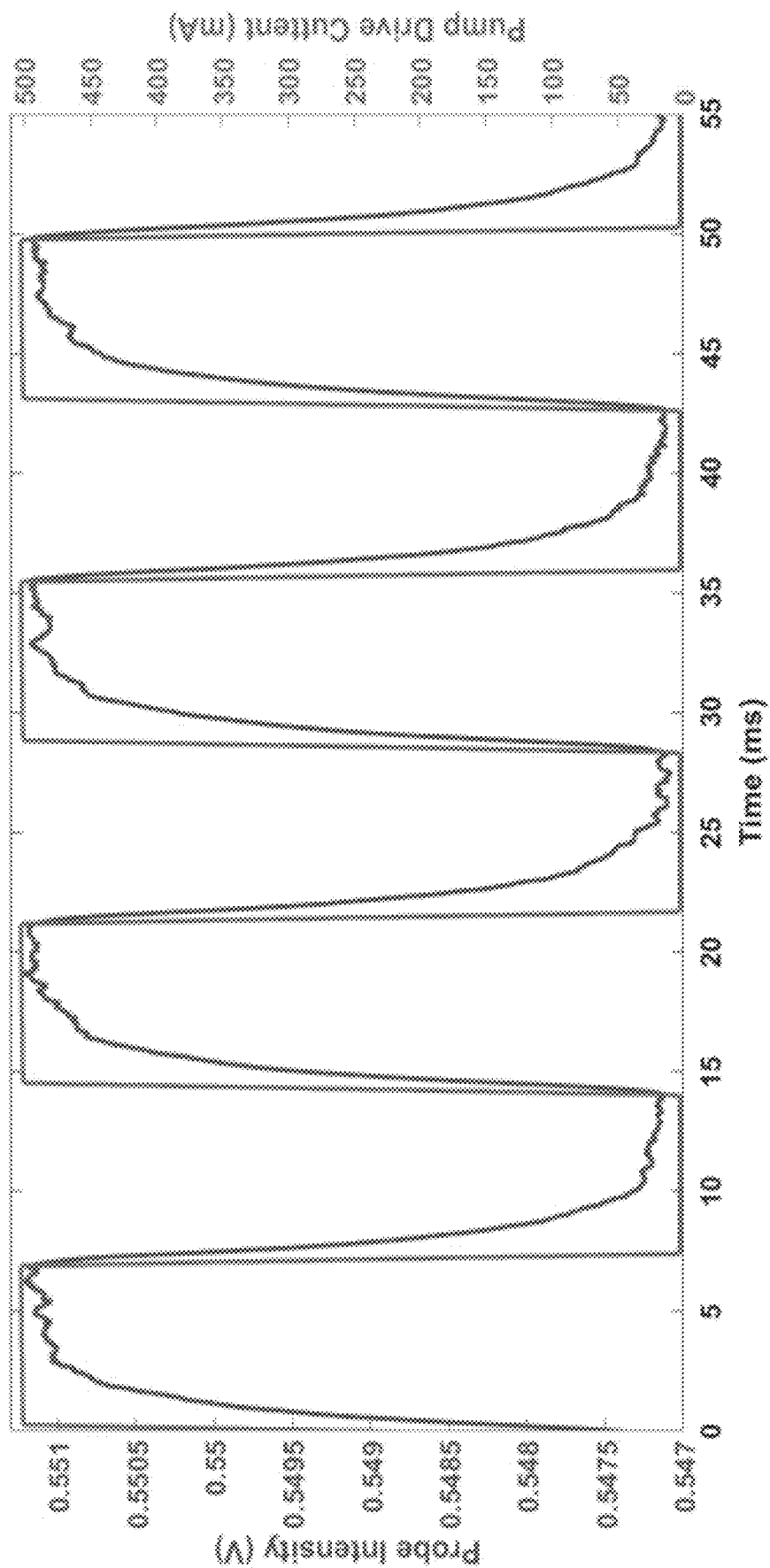
FIG. 26 shows the change in absorbance of a push-pull azobenzene molecule as it switches from the cis to trans configuration under cycled illumination. The switching speed of the molecule is about 1 ms.

IV. After a suitable amount of time has elapsed for a single nucleotide to enter the enzyme, but before multiple nucleotide incorporations can occur the light is turned off, preventing further nucleotides from entering the enzyme. In the case of the "push-pull" azobenzene the molecule will rapidly (ms) return to the inhibitory trans state, as shown in FIG. 26, while for traditional azobenzene molecules illumination at about 460 nm may be required to transition back to the trans state rapidly.

V. The reaction chamber is flushed to remove all excess nucleotides.

VI. The nucleotide and enzyme are co-incubated for sufficient time to enable nucleotide attachment to the template DNA strand, on the order of about 1 to about 10 seconds.

VII. The next nucleotide is introduced into the reaction chamber, as in step II and the cycle is repeated until the desired sequence has been synthesized.

Example 2: Criterion for Selection of Amino Acid Residue Site for Functionalization of the Protein with a Photoswitchable Moiety 1. The residue must be surface exposed, or sufficiently lacking in steric hindrance, and positioned on the molecule such that:
   a. the protein conformation is not changed or impeded in such a way as to prevent the function of the enzyme
   b. the enzyme is able to undergo the necessary conformational changes for its function
   c. the photoswitchable moiety is able to change conformation in response to light excitation
2. The photoswitchable moiety can be positioned to block the active site of the enzyme, but must be removable from the active site by light-induced conformation change of the photoswitch
3. The photoswitch must not occupy or be a modification of catalytically necessary residues such that the enzyme can no longer function Suitable Residues for Modification
1. (6) lysine residues at positions 199, 238, 247, 250, 276, 338 or 419 of the amino acid sequence of mTdT (highlighted in yellow in the sequence alignment)
2. (2) glutamine residues at positions 166 and 423
3. The glutamic acid residue at position 279
4. The methionine residue at 339.
5. (3) phenylalanine residues at 385, 401, and 405
6. Surface exposed residues (bold as shown in the sequence alignment) between:
   a. Residues 146 and 254
   b. Residues 271 and 282
   c. Residues 295 to 341
   d. Residues comprising Loop 1 between 380 and 401
   e. 457 to 471
   f. 478 to 506
   g. Any residues before 146 that are surface exposed and positioned near enough to the active site to enable control of substrate binding by light-activation
7. Charged surface residues such as lysine, arginine, glutamate, aspartate.
8. Polar or hydrophilic side chains
9. Bulky side chains Types of Modifications
1. Insertions of an amino acid (canonical or non-canonical) modified with the photoswitchable moiety
2. Replacements of existing amino acids with a modified amino acid
3. Deletions larger than 1 amino acid, and insertion of the modified photoswitch
4. Modifications onto the side chains of the amino acids As described herein (see for example in FIGS. 1, 3, 6, 8, 9 and 15) residues that are of increasing surface exposure can be determined. Such residues can be suitable for side-chain modifications. (See e.g., Delarue, M. et al. "Crystal structures of a template-independent DNA polymerase: murine terminal deoxynucleotidyl transferase" EMBO 21:3 (2002) 427-439).

TdT Protein Sequence Alignment

Comparing protein sequences (FIG. 10A-D, SEQ ID NOS: 1-4) of murine, bovine (77.7% identity to murine TdT), human (77.5% identity) and shark TdT (52.5% identity) to identify conserved residues suitable for substitution (see alignment below and FIG. 11). The catalytic core (cc) of the murine TdT, SEQ ID NO:5, which begins at AA 130 and underlined in the below alignments, is sufficient provide catalytic activity, as described in [2] and shown by the DNA extension data presented in FIGS. 22 and 23. The number of AA locations for TdT-cc are all in reference to the full length enzyme.

```
MURINE    1  MDPLQAVHLGPRKKRPRQLGTPVASMPYDIRFRELVLFILEKKMGTTRRA   50
             |||.:.|||.||||||||||.|..:||.|.||:|:|||:||||||||||
HUMAN     1  MDPPRASHLSPRKKRPRQTGALMASSPQDIKFQDLVVFILEKKMGTTRRA   50

MURINE   51  FLMELARRKGFRVENELSDSVTHIVAENNSGSDVLEWLQLQNIKASSEFE  100
             ||||||||||||||||||||||||||||||||||||||.|.:.:.||:.|
HUMAN    51  FLMELARRKGFRVENELSDSVTHIVAENNSGSDVLEWLQAQKVQVSSQPE  100

MURINE  101  LLDISWLIECMGAGKPVEMMGRHQLVVNRNSSPSPVPGSQNVPAPAVKKI  150
             |||:||||||:.||||||.|.||||||..|:.:.|...||..||..|:||
HUMAN   101  LLDVSWLIECIRAGKPVEMTGKHQLVVRRDYSDSTNPGPPKTPPIAVQKI  150

MURINE  151  SQYACQRRTTLNNYNQLFTDALDILAENDELRENEGSCLAFMRASSVLKS  200
             |||||||||||||:|||||||.||||||:.||||:.|||.||:|||||||
HUMAN   151  SQYACQRRTTLNNCNQIFTDAFDILAENCEFRENEDSCVTFMRAASVLKS  200

MURINE  201  LPFPITSMKDTEGIPCLGDKVKSIIEGIIEDGESSEAKAVLNDERYKSFK  250
             |||.|.||||||||||||.|||.|||.||||||||||.|||||||||:||
HUMAN   201  LPFTIISMKDTEGIPCLGSKVKGIIEEIIEDGESSEVKAVLNDERYQSFK  250

MURINE  251  LFTSVFGVGLKTAEKWFRMGFRTLSKIQSDKSLRFTQMKAGFLYYEDLV  300
             ||||||||||||:|||||||||||||:||||||:|||||||||||||||
HUMAN    251 LFTSVFGVGLKTSEKWFRMGFRTLSKVRSDKSLKFTRMQKAGFLYYEDLV  300

MURINE  301  SCVNRPEAEAVSMLVKEAVVTFLPDALVTMTGGFRRGKMTGHDVDFLITS  350
             |||.|.||||||:||||||..|||||.||||||||||||..||||||||
HUMAN   301  SCVTRAEAEAVSVLVKEAVWAFLPDAFVTMTGGFRRGKKMGHDVDFLITS  350

MURINE  351  PEATEDEEQQLLHKVTDFWKQQGLLLYCDILESTFEKFKQPSRKVDALDH  400
             |.:|||||.|||.||.:.|:::||||||.|:|||||||.:.||||||||
HUMAN   351  PGSTEDEE-QLLQKVMNLWEKKGLLLYYDLVESTFEKLRLPSRKVDALDH  399

MURINE  401  FQKCFLILKLDHGRVHSEKSGQQEGKGWKAIRVDLVMCPYDRRAFALLGW  450
             ||||||||.||...||.:.|..|||||.||||||||||||:|||||||||
HUMAN   400  FQKCFLIFKLPRQRVDSDQSSWQEGKTWKAIRVDLVLCPYERRAFALLGW  449

MURINE  451  TGSRQFERDLRRYATHERKMMLDNHALYDRTKRVFLEAESEEEIFAHLGL  500
             ||||||||||||||||||||:|||||||||:|||:||:|||||||||||
HUMAN   450  TGSRQFERDLRRYATHERKMILDNHALYDKTKRIFKAESEEEIFAHLGL  499

MURINE  501  DYIEPWERNA  510
             ||||||||||
HUMAN   500  DYIEPWERNA  509

MURINE    1  MDPLQAVHLGPRKKRPRQLGTPVASMPYDIRFRDLVLFILEKKMGTTRRA   50
             ||||.....||||||||||:|.|:..||.|:|.|::||||||||||||.
BOVINE    1  MDPLCTASSGPRKKRPRQVGASMASPPHDIKFQNLVLFILEKKMGTTRRN   50

MURINE   51  FLMELARRKGFRVENELSDSVTHIVAENNSGSDVLEWLQLQNIKASSEFE  100
             |||||||||||||||||||||||||||||||:||||||:|||:|||:.|
BOVINE   51  FLMELARRKGFRVENELSDSVTHIVAENNSGSEVLEWLQVQNIRASSQLE  100

MURINE  101  LLDISWLIECMGAGKPVEMMGRHQLVVNRNSSPSPVPGSQNVPAPAVKKI  150
             |||:||||||.|||||||.|||||||||.:|:.|:.||.|.|:||||||
BOVINE  101  LLDVSWLIESMGAGKPVEITGKHQLVVRTDYSATPNGFQKTPPLAVKKI  150

MURINE  151  SQYACQRRTTLNNYNQLFTDALDILAENDELRENEGSCLAFMRASSVLKS  200
             ||||||:||||||||:||||||.|:||||:|:||||.:|..|||.|||||
BOVINE  151  SQYACQRKTTLNNYNHIFTDAFEILAENSEFKENEVSYVTFMRAASVLKS  200

MURINE  201  LPFPITSMKDTEGIPCLGDKVKSIIEGIIEDGESSEAKAVLNDERYKSFK  250
             |||.|.||||||||||||||||.|||.||||||||||.||||||||:|||
BOVINE  201  LPFTIISMKDTEGIPCLGDKVKCIIEEIIEDGESSEVKAVLNDERYQSFK  250

MURINE  251  LFTSVFGVGLKTAEKWFRMGFRTLSKIQSDKSLRFTQMKAGFLYYEDLV  300
             ||||||||||||:||||||||||:|||.||||.||||||||||||||||
BOVINE  251  LFTSVFGVGLKTSEKWFRMGFRSLSKIMSDKTLKFTKMQKAGFLYYEDLV  300

MURINE  301  SCVNRPEAEAVSMLVKEAVVTFLPDALVTMTGGFRRGKMTGHDVDFLITS  350
             |||.|.||||||:||||||..|||||.||||||||||||..||||||||
BOVINE  301  SCVTRAEAEAVGVLVKEAVWAFLPDAFVTMTGGFRRGKKIGHDVDFLITS  350

MURINE  351  PEATEDEEQQLLHKVTDFWKQQGLLLYCDILESTFEKFKQPSRKVDALDH  400
             |.:|||||.|||.||.:.|:::|||||.|.|||||||||||.||||.||
BOVINE  351  PGSAEDEE-QLLPKVINLWEKKGLLLYYDLVESTFEKFKLPSRQVDTLDH  399

MURINE  401  FQKCFLILKLDHGRVHSEKSGQQEGKGWKAIRVDLVMCPYDRRAFALLGW  450
             ||||||||||||..|||..||.||||.|||||||||||:|||||||||
BOVINE  400  FQKCFLILKLHHQRVDSSKSNQQEGKTWKAIRVDLVMCPYENRAFALLGW  449
```

```
MURINE   451  TGSRQFERDLRRYATHERKMMLDNHALYDRTKRVFLEAESEEEIFAHLGL       500
              ||||||||||:|||||||||||||||||||||:||||||:||||||||||
BOVINE   450  TGSRQFERDIRRYATHERKMMLDNHALYDKTKRVFLKAESEEEIFAHLGL       499

MURINE   501  DYIEPWERNA                                               510
              ||||||||||
BOVINE   500  DYIEPWERNA                                               509

MURINE     1  ---MDPLQAVHLGPRKKRPRQLGTPVASMPYDIRFRDLVLFILEKKMGTT        47
                 ...|..:..|::||.:...........:||:|||..:|:|:|||::
SHARK      1  MSLAGSLGGMGIIPKRKRQKVTEVCSSQSKHQVRFQDLTIFIVERKMGSS        50

MURINE    48  RRAFLMELARRKGFRVENELSDSVTHIVAENNSGSDVLEWLQLQNIKASS        97
              ||:|||:|:||||||||:.:||||||||.||||..:.:|:|...|..:.
SHARK     51  RRSFLMDLARKKGFRVEDVMSDSVTHIVTENNSWDEIWDWIQNLKLLNAD       100

MURINE    98  EFELLDISWLIECMGAGKPVEMMGRHQLVVNRN-SSPSPVPGSQNVPAPA       146
              :.::|:|||...:.|.||||||:..||:|.|:.  .|.||:       |.
SHARK    101  KLKMLNISWFTDSMAAGKPVEIEERHKLQVQKMLQSNSPLP-------PP       143

MURINE   147  VKKISQYACQRRTTLNNYNQLFTDALDILAENDELRENEGSCLAFMRASS       196
              |..||||||||:||||.|::|||||||||||.|...||..:.||.||:|
SHARK    144  VVTISQYACQRRSTLNNRNKIFTDALEILAENEFNENESAYVAFARATS       193

MURINE   197  VLKSLPFPITSMKDTEGIPCLGDKVKSIIEGIIEDGESSEAKAVLNDERY       246
              :||||.|.:..|..:.||.||.||::|||.|:|||.||:::..:.||:|
SHARK    194  LLKSLPYTISKMAALDGLPCFGDQTRAIIEEILEDGVSSKVDDLLCDEKY       243

MURINE   247  KSFKLFTSVFGVGLKTAEKWFRMGFRTLSKIQSDKSLRFTQMQKAGFLYY       296
              |:.|||||||||||||:|||:|.||||:..|||.|.|.|:||||||||||
SHARK    244  KARKLFTSVFGVGLKTADKWYGQGFRTLEAVKASKDLKFTKMQKAGFLYY       293

MURINE   297  EDLVSCVNRPEAEAVSMLVKEAVVTFLPDALVTMTGGFRRGKMTGHDVDF       346
              ||:.:.|.|||||||.:::::.|...|||:|||:||||||||:||||||
SHARK    294  EDINNAVTRPEAEAVAQIIETIVHNYAPDAIVTLTGGFRRGKETGHDVDF       343

MURINE   347  LITSPEATEDEEQQLLHKVTDFWKQQGLLLYCDILESTFEKFKQPSRKVD       396
              ||:.||  |.||  ..|.|::...:||||||.|:.:|||||..|:|.|
SHARK    344  LISCPE-TMDE--NFLRKIVNKLDFRGLLLYYDMVEATFEKRKLSSQKYD       390

MURINE   397  ALDHFQKCFLILKLDHGRVH-----------------SEKSGQQEGKGW       428
              |:||||||||||||:|.||.                 :|...|..|
SHARK    391  AMDHFQKCFLILKLNKALVKNRVSMSSVSAARPTDEGAEPEVKTQIKDW       440

MURINE   429  KAIRVDLVMCPYDRRAFALLGWTGSRQFERDLRRYATHERKMMLDNHALY       478
              |||||||:|:...:.||||||||||||||||||||:.||.||:|||||
SHARK    441  KAIRVDLVIVPTQQFAYALLGWTGSRQFERDLRRYTNHEKSMILDNHGLY       490

MURINE   479  KRTKRVFLEAESEEEIFAHLGLDYIEPWERNA                         510
              ||.|:||.|:||||||||||.|:||||||||
SHARK    491  DRKKKIFLNAKTEEEIFAHLDLEYIEPWERNA                         522

BOVINE        ---MDPLCTASSGPRKKRPRQVGASMASPPHDIKFQNLVLFILEKKMGTTRRNFLMELAR
HUMAN         ---MDPPRASHLSPRKKRPRQTGALMASSPQDIKFQDLVVFILEKKMGTTRRAFLMELAR
MURINE        ---MDPLQAVHLGPRKKRPRQLGTPVASMPYDIRFRDLVLFILEKKMGTTRRAFLMELAR
SHARK         MSLAGSLGGMGIIPKRKRQKVTEVCSSQSKHQVRFQDLTIFIVERKMGSSRSSFLMDLAR
                ..       *::**  :     .  :     :::*::*.:**:*:*** *** :***

BOVINE        RKGRFVENELSDSVTHIVAENNSGSEVLEWLQVQNIRASSQLELLDVSWLIESMGAGKPV
HUMAN         RKGRFVENELSDSVTHIVAENNSGSDVLEWLQAQKVQVSSQPELLDVSWLIECIRAGKPV
MURINE        RKGRFVENELSDSVTHIVAENNSGSDVLEWLQLQNIKASSEFELLDISWLIECMGAGKPV
SHARK         KKGRFVEDVMSDSVTHIVTENNSWDEIWDWIQNLKLLNADKLKMLNISWFTDSMAAGKPV
              :******: :********:**** .:: :*:*   ::   ::  *::**  :.: *****

BOVINE        EITGKHQLVVRTDYSATPNPGFQKTPPLAVKKISQYACQRKTTLNNYNHIFTDAFEILAE
HUMAN         EMTGKHQLVVRRDYSDSTNPGPPKTPPIAVQKISQYACQRRTTLNNCNQIFTDAFDILAE
MURINE        EMMGRHQLVVNRNSSPSPVPGSQNVPAPAVKKISQYACQRRTTLNNYNQLFTDALDILAE
SHARK         EIEERHKLQVQKMLQSNS------PLPPPVVTISQYACQRRSTLNNRNKIFTDALEILAE
              *:   :*:* *.  . .  .      .*    .*:*********:.;****:****:****

BOVINE        NSEFKENEVSYVTFMRAASVLKSLPFTIISMKDTEGIPCLGDKVKCIIEEIIEDGESSEV
HUMAN         NCEFRENEDSCVTFMRAASVLKSLPFTIISMKDTEGIPCLGDKVKGIIEEIIEDGESSEV
MURINE        NDELRENEGSCLAFMRASSVLKSLPFPITSMKDTEGIPCLGDKVKSIIEGIIEDGESSEA
SHARK         KFEFNENESAYVAFARATSLLKSLPYTISKMAALDGLPCFGDQTRAIIEEILEDGVSSKV
              : * *:.***   : :* **.*:****** .*  *   *:**:*.*.:.  *** *:***  **:.

BOVINE        KAVLNDERYQSFKLFTSVFGVGLKTSEKWFRMGFRSLSKIMSDKTLKFTKMQKAGFLYYE
HUMAN         KAVLNDERYQSFKLFTSVFGVGLKTSEKWFRMGFRTLSKVRSDKSLKFTRMQKAGFLYYE
```

-continued

```
MURINE  KAVLNDERYKSFKLFTSVFGVGLKTAEKWFRMGFRTLSKIQSDKSLRFTQMQKAGFLYYE
SHARK   DDLLCDEKYKARKLFTSVFGVGLKTADKWYGQGFRTLEAVKASKDLKFTKMQKAGFLYYE
        . :* **:*:: **************:;**: ***:*. : :* *:** **********

BOVINE  DLVSCVTRAEAEAVGVLVKEAVWAFLPDAFVTMTGGFRRGKKIGHDVDFLITSPGSAEDE
HUMAN   DLVSCVTRAEAEAVSVLVKEAVWAFLPDAFVTMTGGFRRGKKMGHDVDFLITSPGSTEDE
MURINE  DLVSCVNRPEAEAVSMLVKEAVVTFLPDALMTVTGGFRRGKMTGHDVDFLITSPEATEDE
SHARK   DINNAVTRPEAEAVAQIIETIVHNYAPDAIVTLTGGFRRGKETGHDVDFLISCP---ETM
        *:  ..*.*.*****. ::: * : ***:**:******** ********:.*   *

BOVINE  EQ-LLPKVINLWEKKGLLLYYDLVESTFEKFKLPSRQVDTLDHFQKCFLILKLHHQRVD-
HUMAN   EQ-LLQKVMNLWEKKGLLLYYDLVESTFEKLRLPSRKVDALDHFQKCFLIFKLPRQRVD-
MURINE  EQQLLHKVTDFWKQQGLLLYCDILESTFEKFKQPSRKVDALDHFQKCFLILKLDHGRVH-
SHARK   DENFLRKIVNKLDFRGLLLYYDMVEATFEKRKLSSQKYDAMDHFQKCFLILKLNKALVKN
        :: :* *: :  .:***** *::*:**** : .*:: *::**********:**   *.

BOVINE  -----------------SSKSNQQEGKTWKAIRVDLVMCPYENRAFALLGWTGSRQFERD
HUMAN   -----------------SDQSSWQEGKTWKAIRVDLVLCPYERRAFALLGWTGSRQFERD
MURINE  -----------------SEKSGQQEGKGWKAIRVDLVMCPYDRRAFALLGWTGSRQFERD
SHARK   RVLSMSSVSAARPTDEGAEPEVKTQIKDWKAIRVDLVIVPTQQFAYALLGWTGSRQFERD
                         :.  : * *********: * :. *:**************

BOVINE  IRRYATHERKMMLDNHALYDKTKRVFLKAESEEEIFAHLGLDYIEPWERNA
HUMAN   LRRYATHERKMILDNHALYDKTKRIFLKAESEEEIFAHLGLDYIEPWERNA
MURINE  LRRYATHERKMMLDNHALYDRTKRVFLEAESEEEIFAHLGLDYIEPWERNA
SHARK   LRRYTNHEKSMILDNHGLYDRKKKIFLNAKTEEEIFAHLDLEYIEPWERNA
        :***:.**:.*:**** .***.*::**:*:;********.*:********

BOVINE  MDPLCTASSGPRKKRPRQVGASMASPPHDIKFQNLVLFILEKKMGTTRRNFLMELARRKG
HUMAN   MDPPRASHLSPRKKRPRQTGALMASSPQDIKFQDLVVFILEKKMGTTRRAFLMELARRKG
MURINE  MDPLQAVHLGPRKKRPRQLGTPVASMPYDIRFRDLVLFILEKKMGTTRRAFLMELARRKG
        ***   :  .******** *: :** * **:*:**:************ **********

BOVINE  FRVENELSDSVTHIVAENNSGSEVLEWLQVQNIRASSQLELLDVSWLIESMGAGKPVEIT
HUMAN   FRVENELSDSVTHIVAENNSGSDVLEWLQAQKVQVSSQPELLDVSWLIECIGAGKPVEMT
MURINE  FRVENELSDSVTHIVAENNSGSDVLEWLQLQNIKASSEFELLDISWLIECMGAGKPVEMM
        **********************:****** *:::.**: ****:*****. : ******:

BOVINE  GKHQLVVRTDYSATPNPGFQKTPPLAVKKISQYACQRKTTLNNYNHIFTDAFEILAENSE
HUMAN   GKHQLVVRRDYSDSTNPGPPKTPPIAVQKISQYACQRRTTLNNCNQIFTDAFDILAENCE
MURINE  GRHQLVVNRNSSPSPVPGSQNVPAPAVKKISQYACQRRTTLNNYNQLFTDALDILAENDE
        *:*****.. : * :. **   :.*..*********:******* *::****::***** *

BOVINE  FKENEVSYVTFMRAASVLKSLPFTIISMKDTEGIPCLGDKVKCIIEEIIEDGESSEVKAV
HUMAN   FRENEDSCVTFMRAASVLKSLPFTIISMKDTEGIPCLGSKVKGIIEEIIEDGESSEVKAV
MURINE  LRENEGSCLAFMRASSVLKSLPFPITSMKDTEGIPCLGDKVKSIIEGIIEDGESSEAKAV
        :;:** * :;****:*********.* *************.*** *** *********.***

BOVINE  LNDERYQSFKLFTSVFGVGLKTSEKWFRMGFRSLSKIMSDKTLKFTKMQKAGFLYYEDLV
HUMAN   LNDERYQSFKLFTSVFGVGLKTSEKWFRMGFRTLSKVRSDKSLKFTRMQKAGFLYYEDLV
MURINE  LNDERYKSFKLFTSVFGVGLKTAEKWFRMGFRTLSKIQSDKSLRFTQMQKAGFLYYEDLV
        ******:***************:********:***: ***:*:**:**************

BOVINE  SCVTRAEAEAVGVLVKEAVWAFLPDAFVTMTGGFRRGKKIGHDVDFLITSPGSAEDEEQ-
HUMAN   SCVTRAEAEAVSVLVKEAVWAFLPDAFVTMTGGFRRGKKMGHDVDFLITSPGSTEDEEQ-
MURINE  SCVNRPEAEAVSMLVKEAVVTFLPDALVTMTGGFRRGKMTGHDVDFLITSPEATEDEEQQ
        ***.*.***** :******  ******** **********   ***********  :****

BOVINE  LLPKVINLWEKKGLLLYYDLVESTFEKFKLPSRQVDTLDHFQKCFLILKLHHQRVDSSKS
HUMAN   LLQKVMNLWEKKGLLLYYDLVESTFEKLRLPSRKVDALDHFQKCFLIFKLPRQRVDSDQS
MURINE  LLHKVTDFWKQQGLLLYCDILESTFEKFKQPSRKVDALDHFQKCFLILKLDHGRVHSEKS
        ** ** ::*::  ****** *::****** *::***:**:**********:** : **.*.:*

BOVINE  NQQEGKTWKAIRVDLVMCPYENRAFALLGWTGSRQFERDIRRYATHERKMMLDNHALYDK
HUMAN   SWQEGKTWKAIRVDLVLCPYERRAFALLGWTGSRQFERDLRRYATHERKMILDNHALYDK
MURINE  GQQEGKGWKAIRVDLVMCPYDRRAFALLGWTGSRQFERDLRRYATHERKMMLDNHALYDR
        . ****.*********:***: .***************:***********:********:

BOVINE  TKRVFLKAESEEEIFAHLGLDYIEPWERNA
HUMAN   TKRIFLKAESEEEIFAHLGLDYIEPWERNA
MURINE  TKRVFLEAESEEEIFAHLGLDYIEPWERNA
        ***:**:**********************
```

Example 3. Gating Synthesis by Photo-Controlling DNA Ratcheting

This method requires an engineered enzyme that has been modified with a cross-linking azobenzene derivative or other photoswitchable molecule. The cross-linking group will change the configuration of the loop responsible for DNA ratcheting. After extension of the DNA by TdT the protein ratchets the DNA to enable the addition of a subsequent nucleotide. By placing the ratcheting function under photocontrol, extension of the DNA can be gated as desired. A system enabling the introduction and flushing of reactants and the optical stimulation of the enzyme is also required.

I. TdT is incubated with a template (seed) DNA strand to enable TdT association with seed DNA substrate. It may be required to illuminate the enzyme during this step to enable association of the enzyme with the DNA.

II. The first nucleotide in the desired DNA sequence is introduced in into the reaction chamber.

III. The nucleotide and enzyme are co-incubated for sufficient time to enable nucleotide attachment to the template DNA strand, on the order of 1-10 seconds. Multiple incorporations are not possible, because the DNA is unable to ratchet and so the active site is blocked from further incorporation.

IV. The reaction chamber is flushed to remove all excess nucleotides.

V. The enzyme is illuminated at the wavelength required to switch an azobenzene molecule, from the trans to the cis configuration. For thermally fast relaxing "push-pull" azobenzenes, this wavelength will be in the blue range at about 405 to about 450 nm for example, and more specifically at about 450 nm. Azobenzene molecules that have not been modified for fast relaxation can be typically illuminated in, for example, the UV light range at about 320 nm to about 356 nm. The change in state of the azobenzene switches the configuration of the loop enabling the ratcheting of the DNA, thereby freeing the active site for a subsequent nucleotide addition.

VI. The next nucleotide is introduced into the reaction chamber, as in step II and the cycle is repeated until the desired sequence has been synthesized.

Example 4: Cross-Linking Residues in TdT to Create the Photo-Controlled Enzyme-Target Residues to Modify the TdT Ratchet Loop Residues on Loop 1 comprised of amino acids between 380 and 401 in the mTDT sequence. The modification may be between residues within the Loop, or between the loop and the rest of the protein. The residues will be identified by modeling the conformation change in the protein to identify residues that, relative to one another, change positions through the conformation change.

Criterion:
1. The residues must be exposed such that a photoswitchable linker can connect them
2. The residues must be close enough to be acted upon by a linker
3. The residues must change conformation in a manner necessary for the overall protein conformation change
4. The residues must change position such that the change in conformation of a photoswitchable moiety can be linked to the relative change in positions of the amino acids, through the protein's conformational change Potential residues:
K387 and D441
D399 and K403

Example 5. Gating Synthesis Through the Control of Metal Ion Introduction

This method can be carried out with native TdT, but optimally requires an enzyme modified such that the sites for binding MA and MB accept different metal ions, thereby enabling MB to facilitate nucleotide binding in the pocket, but inhibiting extension until such a time as MA is introduced.

I. TdT is incubated with a template (seed) DNA strand to enable TdT association with seed DNA substrate.

II. The first nucleotide in the desired DNA sequence is introduced in into the reaction chamber, along with MB to facilitate nucleotide binding.

III. The reaction chamber is flushed to remove all excess nucleotides.

IV. MA is introduced into the reaction chamber for sufficient time to enable nucleotide attachment to the template DNA strand, on the order of about 1 to about 10 seconds. Following incorporation MA will leave the enzyme.

V. A chelating agent, such as EDTA, is introduced into the chamber to sequester metal ions and the chamber will be flushed.

VI. The next nucleotide is introduced into the reaction chamber, as in step II and the cycle is repeated until the desired sequence has been synthesized.

Example 6. Fluorescently-Verified and Photo-Controlled Synthesis

Figure 12:
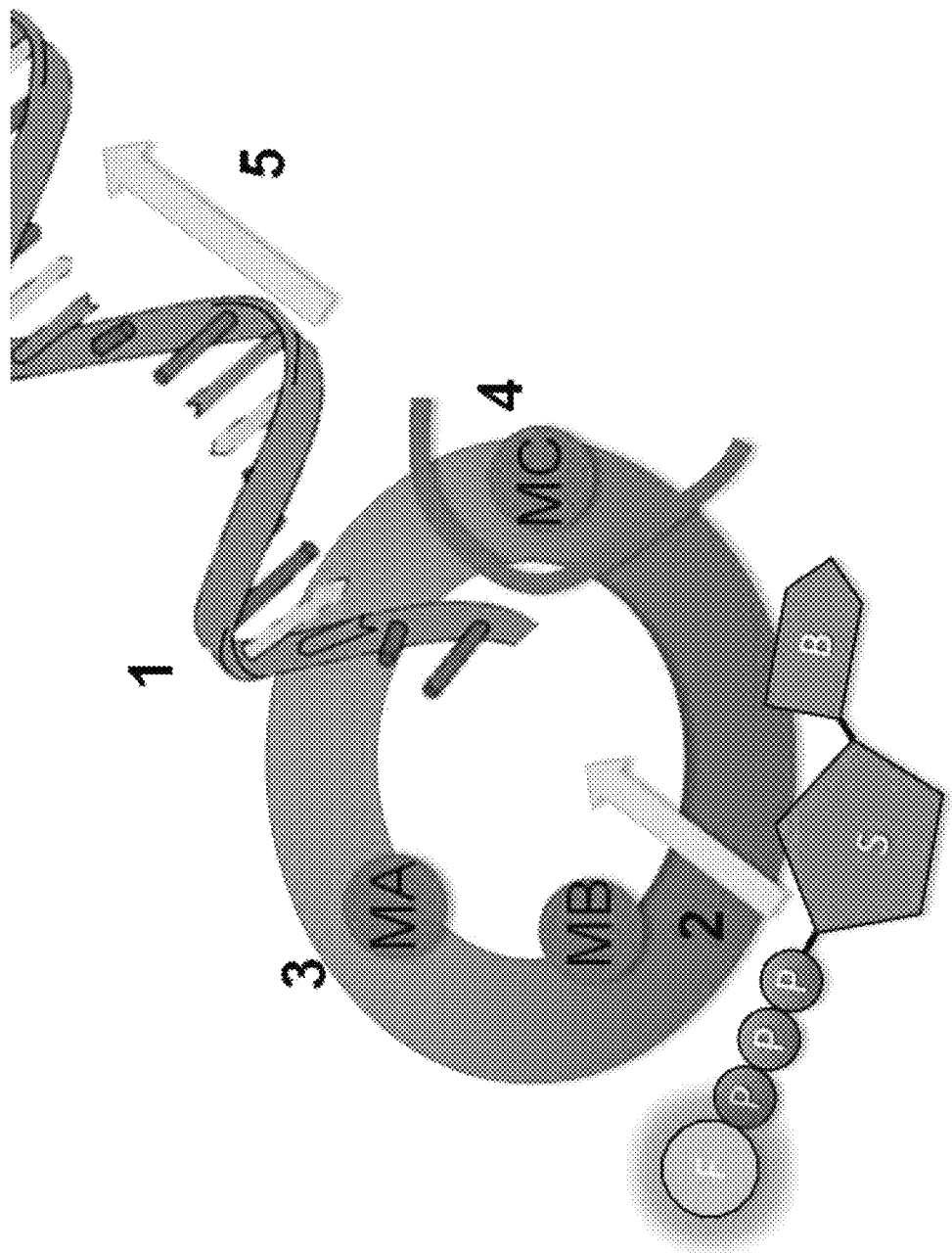
FIG. 12 is a graphic showing fluorescently-verified and photo-controlled synthesis.
Figure 15:
FIG. 15 shows the global alignment of four structures of murine TDT bound to nucleotide competitive inhibitors of mTDT. In light blue and light green are 4IQT and 4IQV respectively, and in light purple and brown are 4IQU and 4IQW respectively [5], each pair representing 1 class of inhibitor. Such inhibitors could be used as reversible inhibitors of nucleotide synthesis. For example, they could serve as the blocking group on a photo-activatable blocking moiety such as that depicted in FIG. 14. These competitive inhibitors, and the others described in the [5], could effectively block the active site from nucleotide addition, until a light source induces isomerization in the azobenzene cross-linking the inhibitor to the enzyme, forcing the inhibitor to temporarily leave the active site and activate the enzyme.

This method enables the enzymatic addition to be paused at multiple points to both provide precise control of enzymatic extension and to verify nucleotide incorporation fluorescently. It requires both the enzyme modifications described in Examples 2 and 3 above, as well as a nucleotide that has a cleavable fluorescent label and can be incorporated by TdT. The ideal nucleotide for this application is one with a phosphate coupled fluorophore, as the fluorophore will be cleaved upon incorporation. An alternative nucleotide is one that is labeled on the base. The fluorophore can then be cleaved either chemically, photochemically, or electrochemically, when the incorporation if verified. Such a nucleotide needs to be designed with care so that complementary pairing with the base is not impeded after fluorophore removal. (FIG. 12).

I. TdT is incubated with a template (seed) DNA strand to enable TdT association with seed DNA substrate.

II. The first nucleotide in the desired DNA sequence is introduced in into the reaction chamber, along with MB to facilitate nucleotide binding.

II. The reaction chamber is flushed to remove all excess nucleotides.

IV. The presence of a nucleotide in the pocket is verified fluorescently.

V. MA is introduced into the reaction chamber for sufficient time to enable nucleotide attachment to the template DNA strand, on the order of about 1 to about 10 seconds. Following incorporation MA will leave the enzyme.

VI. For phosphate labeled nucleotides, the incorporation is verified through the change in fluorescence associated with the cleavage of the fluorophore.

VII. A chelating agent, such as EDTA, is introduced into the chamber to sequester metal ions and the chamber will be flushed.

VIII. The enzyme is illuminated at the wavelength required to switch an azobenzene molecule, from the trans to the cis configuration. For thermally fast relaxing "push-pull" azobenzenes, this wavelength will be in the visible blue range, about 405 nm to about 450 nm, for example. Azobenzene molecules that have not been modified for fast relaxation require illumination in the UV light range, e.g., at about 320 nm to about 356 nm. The change in state of the azobenzene switches the configuration of the loop enabling the ratcheting of the DNA, thereby freeing the active site for a subsequent nucleotide addition.

IX. The next nucleotide is introduced into the reaction chamber, as in step II and the cycle is repeated until the desired sequence has been synthesized.

Example 8: Methods for Inserting Artificial Amino Acids in the TdT Protein

Methods for introducing non-natural/unnatural amino acids into a protein are known to those of skill in the art. For example, some methods are outlined in "Replacing amino acids in translation: Expanding chemical diversity with non-natural variants" White et al., Methods 60 (2013) 70-74.

The approach currently being investigated involves the use of an IVTT (in vitro transcription and translation) system lacking one of the release factors, therefore freeing one of the redundant stop codons for genetic recoding. Alternatively, a similar approach can be taken in vivo using cells (*E. coli* for example) that are recoded to eliminate a particular stop codon (i.e. the Amber codon). An engineered tRNA that binds to the Amber stop codon TAA can then be used to incorporate a non-canonical amino acid. This stop codon, inserted into the amino acid sequence of a protein, will allow the engineered tRNA to bind and incorporate the non-canonical amino acid in a site-specific way. Amino acids that contain either the desired modification, or a chemical group that can be acted upon in a site-specific manner (such as click chemistry side chains), can be attached to the tRNA prior to the IVTT reaction or cellular expression and provided to the reaction in trans. The incorporation of unnatural amino acids (UAA) can be accomplished in vivo using an evolved aminoacyl-tRNA synthetase. (aaRS)/tRNA pair. The tRNA must be evolved so that its anticodon binds to the desired codon, such as the Amber stop codon, while the aaRS must "charge" the evolved tRNA by attaching the UAA. This pair will be chosen from an orthogonal system, such as *Methanocalcodoccus jannaschii*, to prevent interference with normal host translation, for example by the aaRS charging a host tRNA. Genes for the desired aaRS/tRNA pair can be delivered on a plasmid and expressed in either a constitutive or inducible manner, while the unnatural amino acid can be provided by media supplementation. Several methods can be used to prevent the codon reassignment and native host systems from interfering with protein expression: (1) high expression of the mutant tRNA can overwhelm the endogenous tRNA. (2) the desired codon can be removed from the host genome and replaced with a conserved codon (i.e. a silent mutation) (3) a tRNA suppressor can be expressed to curb native tRNA activity. After production within the host, the mutant protein can be purified using classical methods such as Histidine-tagged purification.

Insertion of the artificial amino acids can be achieved using the NEB PURExpress system delta RF 123 kit, which lacks the 3 release factors but provides them separately. This kit will allow only 1 or 2 of the release factors to be used such that one of the stop codons is no longer recognized as such. tRNAs charged with a click chemistry—modified lysine amino acid can then be incorporated at sites specified by the recoded stop codon.

Example 9: Method for Synthesizing the Azobenzene Photoswitch-Modified Amino Acid Click chemistry refers to a group of reactions that are modular, wide in scope, have very high yields, generate only inoffensive byproducts that can be removed by nonchromatographic methods. While the reactions can be stereospecific, they do not need to be enantioselective. Click chemistry characteristics include simple reaction conditions (e.g., under ideal conditions, the process should be insensitive to oxygen and water), readily available starting materials and reagents, the use of no solvent or solvents that are benign (such as water) or easily removed, and simple product isolation.

Nonchromatographic purification methods that could be used involve crystallization or distillation. Generally, the result is a product that is stable under physiological conditions. See, e.g., Kolb H C, Finn M G, Sharpless K B. *Click Chemistry: Diverse Chemical Function From a Few Good Reactions*, Angew. Chem., Int. Ed., Engl. 2001; 40:2004-2021.

Aspects of the invention rely on click chemistry principles to incorporate a photoswitch, an azobenzene-based compound, for example, in TdT. In many implementations, the resulting TdT is photoisomerzable and contains one or more azobenzene moiety or moieties that can regulate entry or binding of a mononuceotide to an active site of the enzyme.

Examples of some common click chemistries that can be used or adapted in conducting embodiments of the invention include but are not limited to linking reactions that utilize azide-cyclooctyne (dibenzenecyclooctyne or DBCO, for instance); trans-cyclooctene-tetrazine or norbornene-tetrazine. A general click chemistry review is provided by Patterson, D. M.; Nazarova, L. A.; Prescher, J. A. ACS Chemical Biology, 2014, 9, 592. Details regarding the DBCO/azide chemistry can be found in Jewett, J. C.; Sletten, E. M.; Bertozzi, C. R. J. Am. Chem. Soc. 2010, 132, 3688.

Further aspects of the invention relate to suitable photoswitchable azobenzene moieties and methods for preparing them.

Azobenzenes with substituents available for introduction of clickable moieties and peptide chains can be synthesized either from commercially available azobenzenes (e.g., disperse red or 4,4'-(diazene-1,2-diyl)dianiline) or by reacting appropriately substituted anilines (e.g., 2-(ethyl(phenyl) amino)ethanol, having the N-ethanol substituent as a functional handle) with appropriately substituted aniline compounds (e.g., 4-aminobenzoic acid) in the presence of sodium nitrite and acid.

Alternatively, an aniline substituted with an electron-donating group containing a functional handle (e.g., 4-(ethyl (2-hydroxyethyl)amino)benzenaminium sulfate)) can be converted to a symmetrical azobenzene (also known as "diazobenzene") after treatment with sodium bicarbonate and manganese dioxide, as described, for instance, by L. Chi et al., Bioconjugate Chem 2006, 17, 670-676. The molecule can be desymmetrized via mono-etherification of one ethanol substituent with a linker containing another functional group handle (e.g., a Boc-protected amine). The molecule will now have amine and alcohol substituents that can be modified further for introduction of peptides or clickable moieties.

Other possible synthetic methods for preparing substituted azobenzene are described by F. Hamon et al., Tetrahedron 65 (2009) 10105-10123.

In all cases one functional group handle, present in the azobenzene synthesized, will be converted to a clickable moiety (e.g., an azide) by either direct conversion of an alcohol to an azide (via tosylation and displacement with sodium azide) or by etherification with a linker containing an amine; the amine can be then reacted with an N-hydroxysuccinimidyl ester-containing molecule that also has a clickable moiety.

Figure 27:
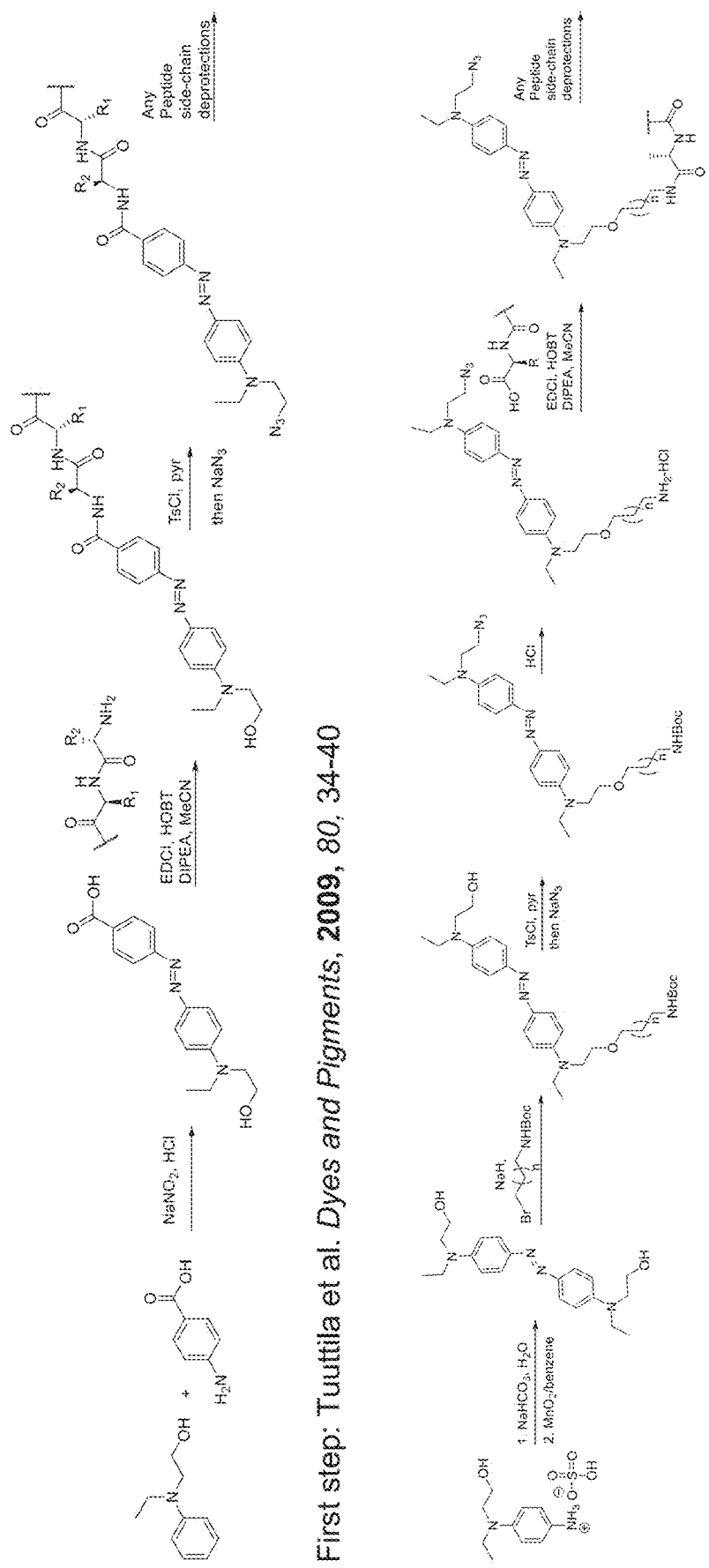
FIG. 27 presents pathways that can be used in the embodiments described herein.
Figure 27:
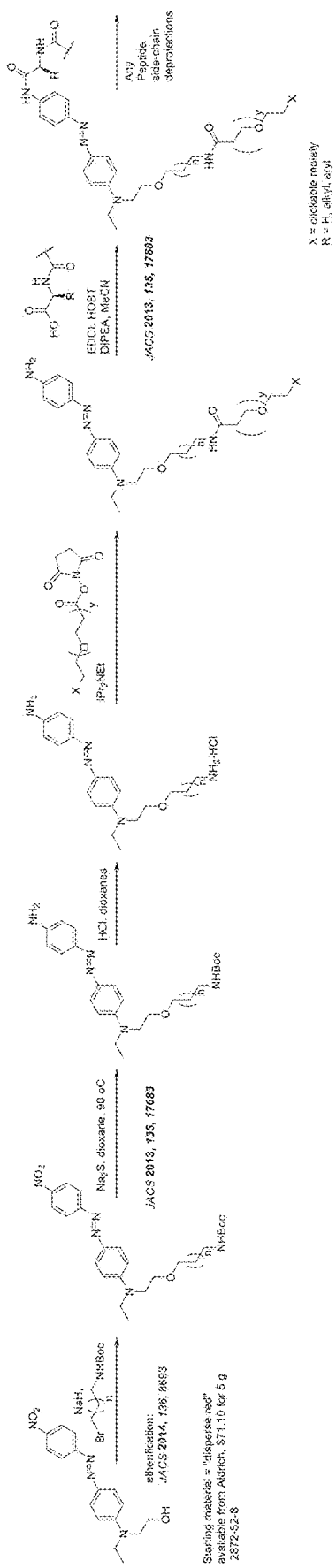

Peptides can be introduced via standard peptide coupling reactions to either an acid or amine substituent on the diazobenzene. Side-chain deprotections can be performed if necessary. Illustrative reactions are shown in FIG. 27.

While azobenzenes are believed to offer ideal photophysical properties and kinetics for applications described herein, spiropyrans, hemithioindigos, diarylethenes, are other possible photoswitchable compounds that can be employed.

Example 10: Azobenzene Compounds and Synthetic Schemes

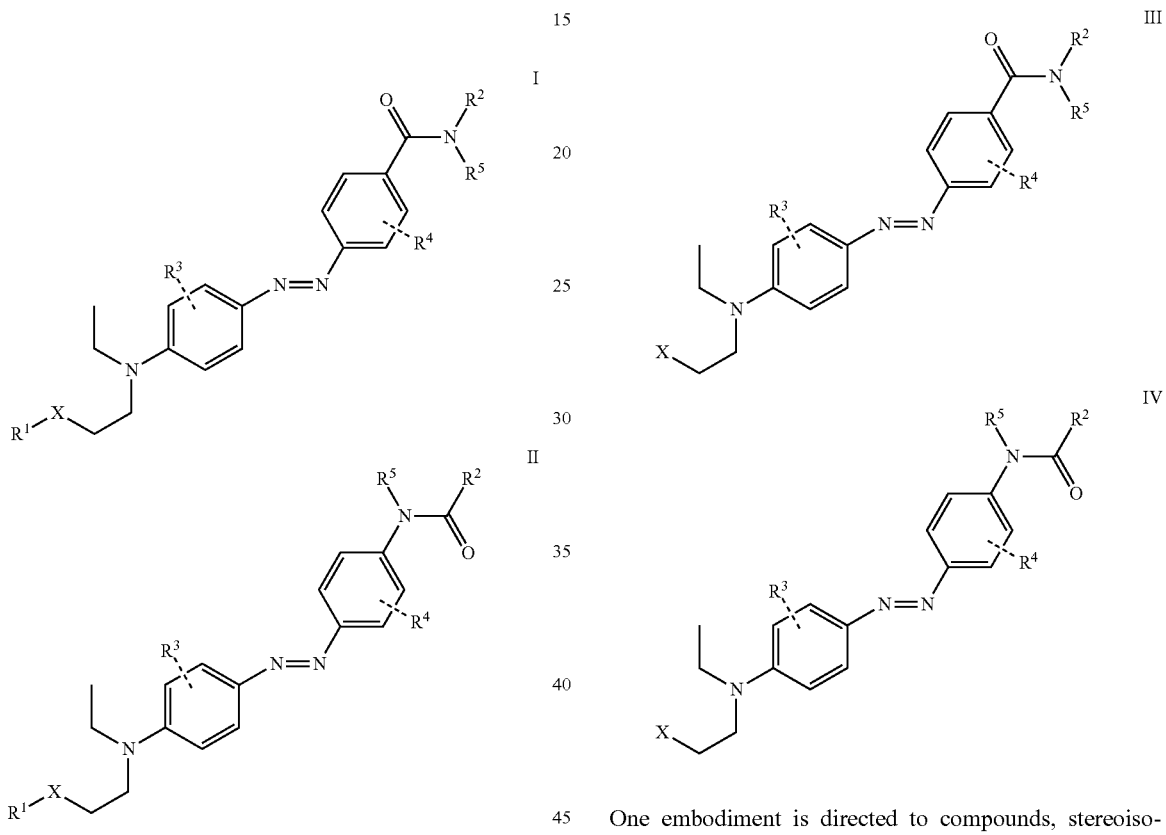

As described herein, the engineered TdT of the present invention can comprise a photoswitchable azobenzene derivative. In particular the azobenzene molecules of the present invention can be derivatized/modified with chemical moieties that allow for bioconjugation. More specifically, the azobenzenes of the present invention comprise a clickable functional group. Examples of suitable azobenzene core structures and suitable chemical moieties/substituents for use in the present invention are described.

One embodiment is directed to compounds, stereoisomers, tautomers, and solvates of Formulas I and II, where X is O, N-alkyl, NH, S, S(O), HN—C(O)—O, or O—C(O)—O.

$R^1$ and $R^2$ are independently selected from the group consisting of alkyl, substituted alkyl, acyl, cycloalkyl, substituted cycloalkyl, aryl, substituted aryl, heterocyclyl, substituted heterocyclyl, heteroaryl, and substituted heteroaryl; $R^1$ and $R^2$ contain moieties that allow for bioconjugation to occur either via click chemistry or by chemistries such as amidation reactions, thiol-ene reactions, or maleimides-thiol conjugations.

$R^3$ and $R^4$ are independently selected from the group consisting of hydrogen, halo, alkyl, substituted alkyl, acyl, cycloalkyl, substituted cycloalkyl, aryl, substituted aryl, heterocyclyl, substituted heterocyclyl, heteroaryl, substituted heteroaryl, amino, substituted amino, acylamino, alkoxy, substituted alkoxy, carboxyl, carboxyl ester, substituted sulfonyl, aminosulfonyl, and aminocarbonyl.

$R^5$ is selected from the group consisting of hydrogen, alkyl, substituted alkyl, acyl, cycloalkyl, substituted cycloalkyl, aryl, substituted aryl, heterocyclyl, substituted heterocyclyl, heteroaryl, and substituted heteroaryl;

One embodiment is directed to compounds, stereoisomers, tautomers, and solvates of Formulas III and IV, where X is OH, N-alkyl, $NH_2$, SAc, OAc, or $N_3$ $R^2$ is selected from the group consisting of alkyl, substituted alkyl, acyl, cycloalkyl, substituted cycloalkyl, aryl, substituted aryl, heterocyclyl, substituted heterocyclyl, heteroaryl, and substituted heteroaryl; $R^2$ contains moieties that allow for bioconjugation to occur either via click chemistry or by chemistries such as amidation reactions, thiol-ene reactions, or maleimides-thiol conjugations.

$R^3$ and $R^4$ are independently selected from the group consisting of hydrogen, halo, alkyl, substituted alkyl, acyl, cycloalkyl, substituted cycloalkyl, aryl, substituted aryl, heterocyclyl, substituted heterocyclyl, heteroaryl, substituted heteroaryl, amino, substituted amino, acylamino, alkoxy, substituted alkoxy, carboxyl, carboxyl ester, substituted sulfonyl, aminosulfonyl, and aminocarbonyl.

$R^5$ is selected from the group consisting of hydrogen, alkyl, substituted alkyl, acyl, cycloalkyl, substituted cycloalkyl, aryl, substituted aryl, heterocyclyl, substituted heterocyclyl, heteroaryl, and substituted heteroaryl;

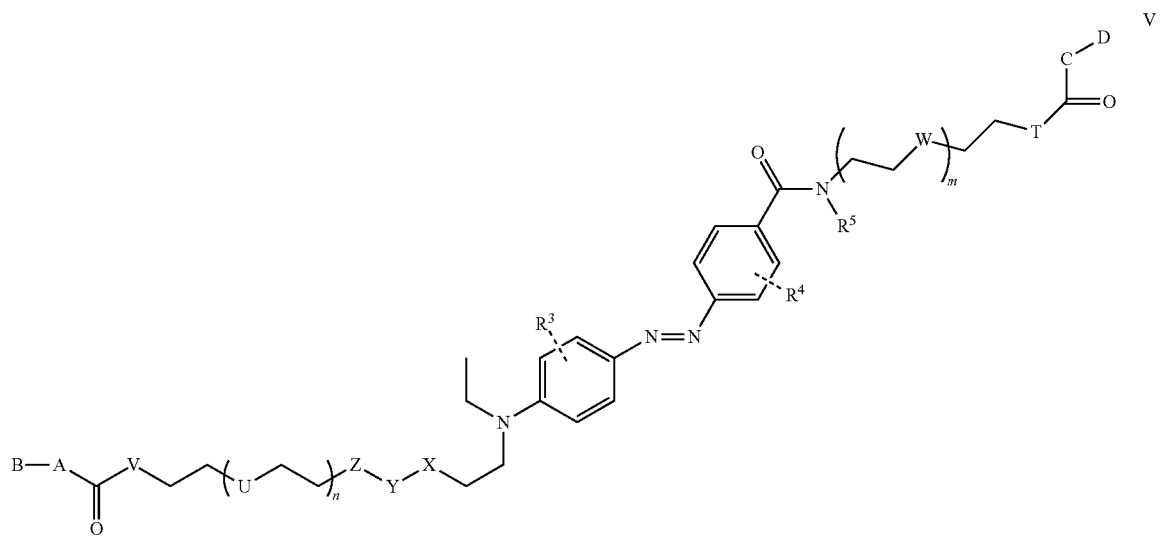

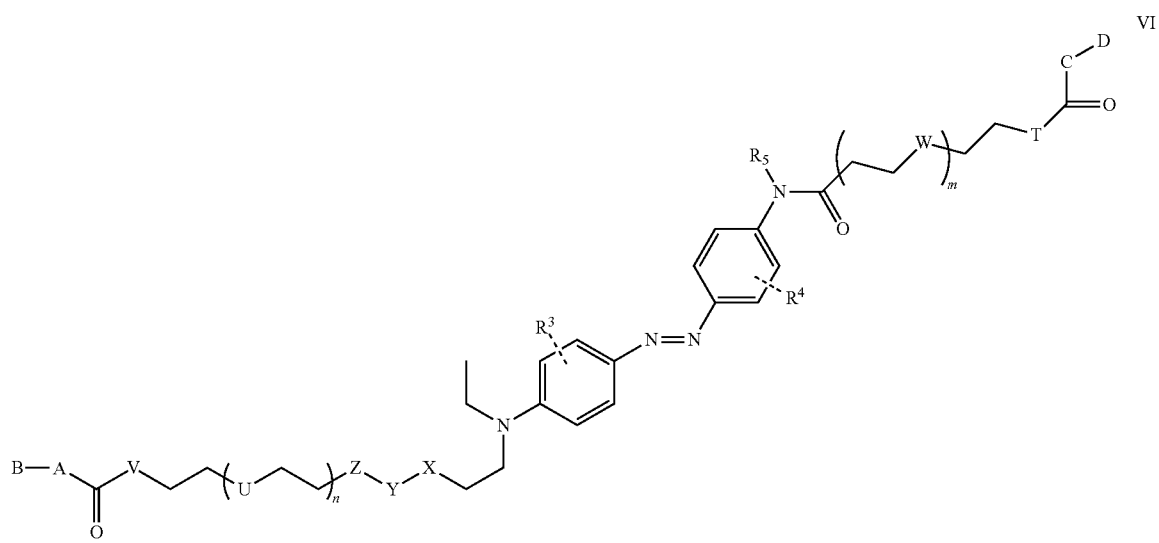

One embodiment is directed to compounds, stereoisomers, tautomers, and solvates of Formulas V and VI, where U, X, Y, W, Z are independently selected from a group consisting of O, N-alkyl, NH, S, S(O), $CH_2$, or C(O), or $CH_2$; optionally, in some cases any one of Z, Y, or X may be omitted.

U and W are independently selected from a group consisting of O, NH, N-alkyl, S, S(O), or $CH_2$ V and T are independently selected from a group consisting of NH, O, S, N-alkyl or N-acyl n is 0, or an integer from 1 to 15 m is 0 or an integer from 1 to 15

A and C represent and are selected from linkers that could consist of alkyl groups, alkoxy groups, alkenyl groups, or alkynyl groups B and D represent and are selected from functional groups used in bioconjugation including amine, carboxylate, carboxylic acid, aldehyde, ketone, maleimide, or click chemistry groups including alkyne, cycloocytne, trans-cyclooctene, norbornene, azide, and other functionalities used in bioconjugation chemistries described in Patterson, D. M.; Nazarova, L. A.; Prescher, J. A. *ACS Chemical Biology* 2014, 9, 592.

$R^3$ and $R^4$ are independently selected from the group consisting of hydrogen, halo, alkyl, substituted alkyl, acyl, cycloalkyl, substituted cycloalkyl, aryl, substituted aryl, heterocyclyl, substituted heterocyclyl, heteroaryl, substituted heteroaryl, amino, substituted amino, acylamino, alkoxy, substituted alkoxy, carboxyl, carboxyl ester, substituted sulfonyl, aminosulfonyl, and aminocarbonyl.

$R^5$ is selected from the group consisting of hydrogen, alkyl, substituted alkyl, acyl, cycloalkyl, substituted cycloalkyl, aryl, substituted aryl, heterocyclyl, substituted heterocyclyl, heteroaryl, and substituted heteroaryl;

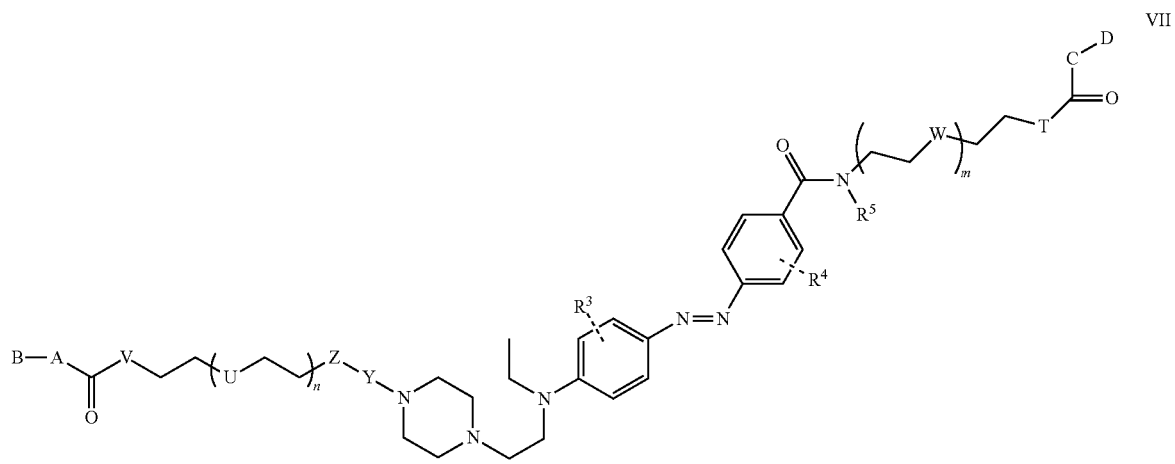

VII

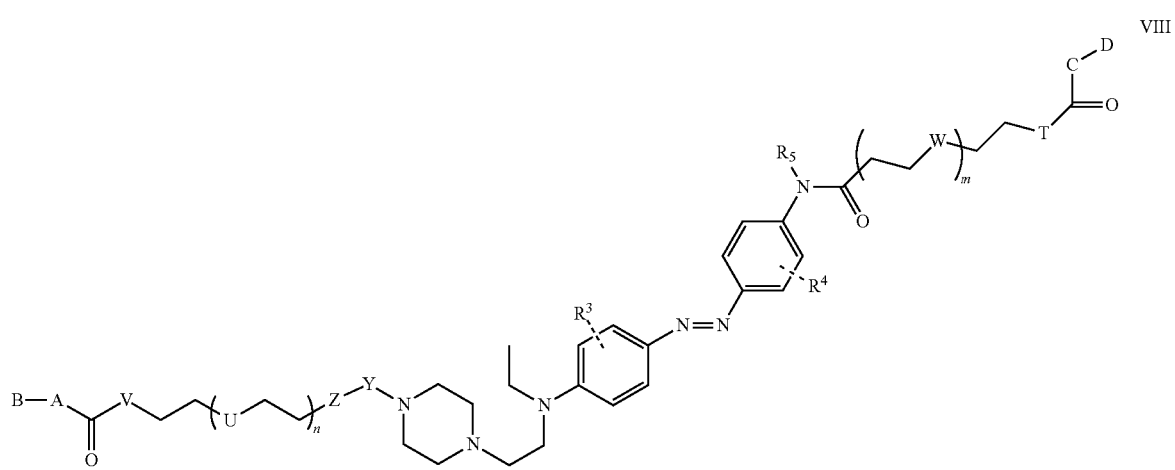

VIII

One embodiment is directed to compounds, stereoisomers, tautomers, and solvates of Formulas VII and VIII, where U, Y, W, Z are independently selected from a group consisting of O, N-alkyl, NH, S, S(O), CH$_2$, or C(O), or CH$_2$; optionally in some cases any one of Z, Y, or X may be omitted.

U and W are independently selected from a group consisting of O, NH, N-alkyl, S, S(O), or CH$_2$ V and T are independently selected from a group consisting of NH, O, S, N-alkyl or N-acyl n is 0, or an integer from 1 to 15 m is 0 or an integer from 1 to 15

A and C represent and are selected from linkers that could consist of alkyl groups, alkoxy groups, alkenyl groups, or alkynyl groups B and D represent and are selected from functional groups used in bioconjugation including amine, carboxylate, carboxylic acid, aldehyde, ketone, maleimide, or click chemistry groups including alkyne, cycloocytne, trans-cyclooctene, norbornene, azide, and other functionalities used in bioconjugation chemistries described in Patterson, D. M., Nazarova, L. A.; Prescher, J. A. *ACS Chemical Biology* 2014, 9, 592.

R$^3$ and R$^4$ are independently selected from the group consisting of hydrogen, halo, alkyl, substituted alkyl, acyl, cycloalkyl, substituted cycloalkyl, aryl, substituted aryl, heterocyclyl, substituted heterocyclyl, heteroaryl, substituted heteroaryl, amino, substituted amino, acylamino, alkoxy, substituted alkoxy, carboxyl, carboxyl ester, substituted sulfonyl, aminosulfonyl, and aminocarbonyl.

R$^5$ is selected from the group consisting of hydrogen, alkyl, substituted alkyl, acyl, cycloalkyl, substituted cycloalkyl, aryl, substituted aryl, heterocyclyl, substituted heterocyclyl, heteroaryl, and substituted heteroaryl;

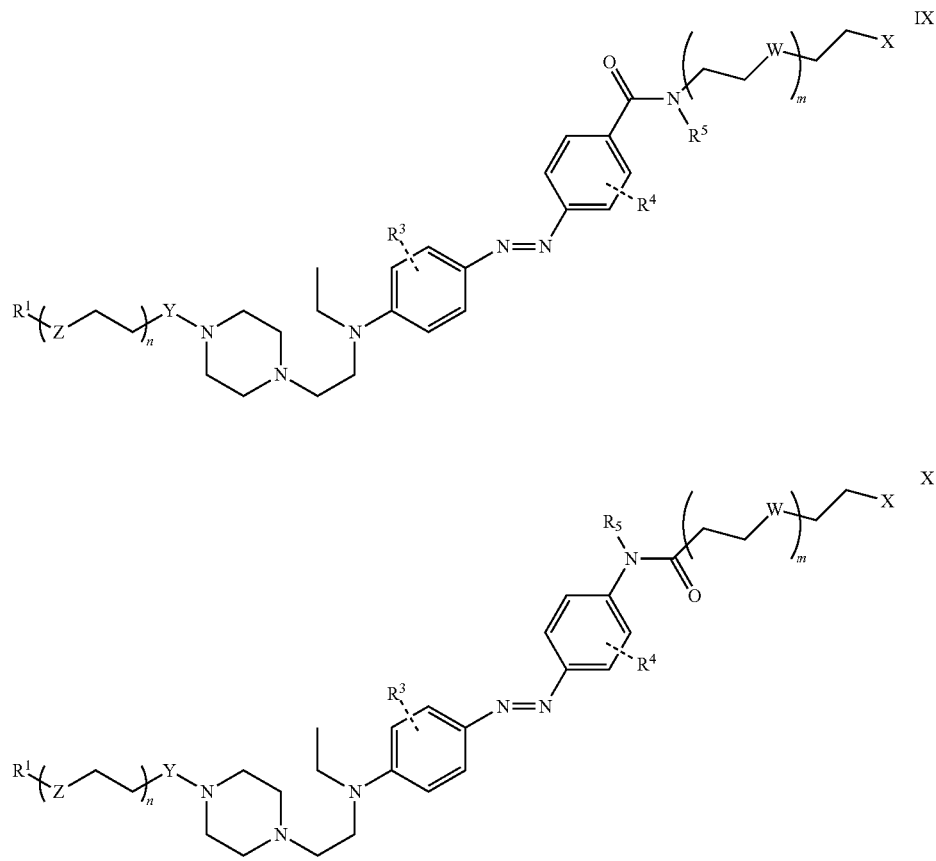

One embodiment is directed to compounds, stereoisomers, tautomers, and solvates of Formulas IX and X where W, X, Y, and Z are independently selected from a group consisting of O, N-alkyl, NH, S, S(O), $CH_2$, or C(O), $CH_2$, $NH_2$, or $N_3$ n is 0, or an integer from 1 to 15 m is 0 or an integer from 1 to 15

$R^3$ and $R^4$ are independently selected from the group consisting of hydrogen, halo, alkyl, substituted alkyl, acyl, cycloalkyl, substituted cycloalkyl, aryl, substituted aryl, heterocyclyl, substituted heterocyclyl, heteroaryl, substituted heteroaryl, amino, substituted amino, acylamino, alkoxy, substituted alkoxy, carboxyl, carboxyl ester, substituted sulfonyl, aminosulfonyl, and aminocarbonyl.

$R^5$ is selected from the group consisting of hydrogen, alkyl, substituted alkyl, acyl, cycloalkyl, substituted cycloalkyl, aryl, substituted aryl, heterocyclyl, substituted heterocyclyl, heteroaryl, and substituted heteroaryl;

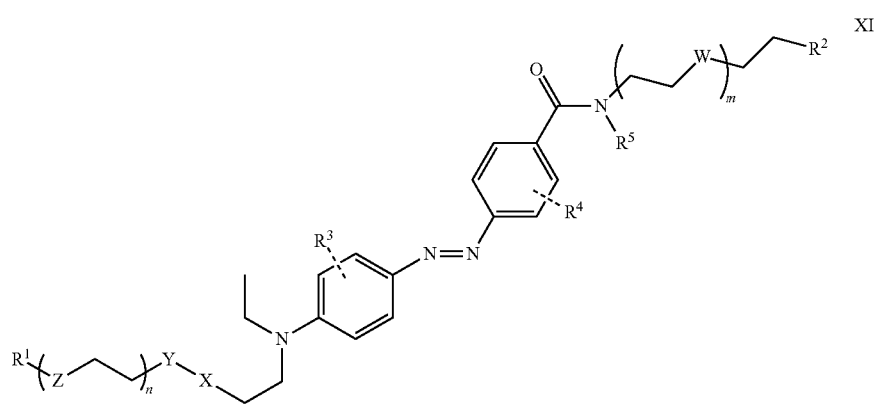

-continued

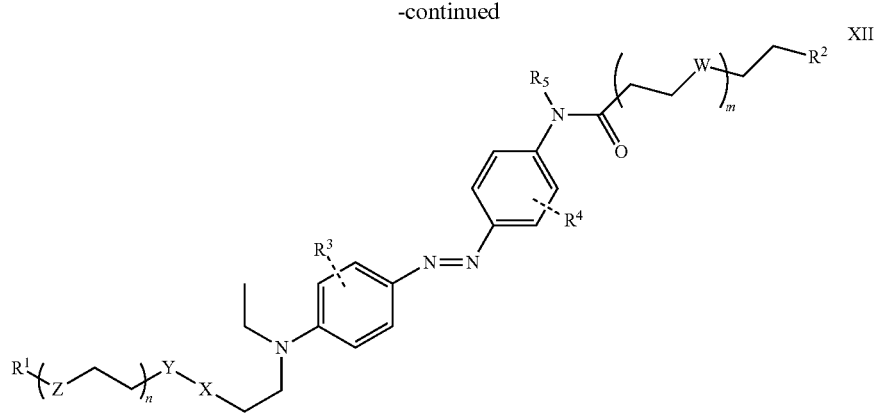

One embodiment is directed to compounds, stereoisomers, tautomers, and solvates of Formulas XI and X, where XII is O, N-alkyl, NH, S, S(O), HN—C(O)—O, or O—C(O)—O.

$R^1$ and $R^2$ are independently selected from the group consisting of alkyl, substituted alkyl, acyl, cycloalkyl, substituted cycloalkyl, aryl, substituted aryl, heterocyclyl, substituted heterocyclyl, heteroaryl, and substituted heteroaryl, or azide; $R^1$ and $R^2$ contain moieties that allow for bioconjugation to occur either via click chemistry or by chemistries such as amidation reactions, thiol-ene reactions, or maleimides-thiol conjugations.

$R^3$ and $R^4$ are independently selected from the group consisting of hydrogen, halo, alkyl, substituted alkyl, acyl, cycloalkyl, substituted cycloalkyl, aryl, substituted aryl, heterocyclyl, substituted heterocyclyl, heteroaryl, substituted heteroaryl, amino, substituted amino, acylamino, alkoxy, substituted alkoxy, carboxyl, carboxyl ester, substituted sulfonyl, aminosulfonyl, and aminocarbonyl.

$R^5$ is selected from the group consisting of hydrogen, alkyl, substituted alkyl, acyl, cycloalkyl, substituted cycloalkyl, aryl, substituted aryl, heterocyclyl, substituted heterocyclyl, heteroaryl, and substituted heteroaryl;

W, X, Y, and Z are independently selected from the group consisting of O, N, NH, N-alkyl, S, S(O), C(O), or $CH_2$ n is 0, or an integer from 1 to 15 m is 0 or an integer from 1 to 15

Example 11: General Synthetic Methods

Schemes 1-6 illustrate general methods for the preparation of intermediates and compounds of the azobenzene derivatives that are suitable for use as described herein. These general synthetic methods can be modified/adapted to produce azobenzene compounds that are suitable for bioconjugation and use as photoswitchable azobenzene derivatives to modify the DNA polymerases of the present invention. One skilled in the art is familiar with these general synthetic methods and the determination of the appropriate reaction conditions for producing the azobenzene compounds suitable for use in the methods described herein. For example, determination of the appropriate solvents, temperature and/or protecting groups are routine and known to those of skill. See, for example, Kienzler, M. A.; Reiner, A.; Trautman, E.; Yoo, S.; Trauner, D.; isacoff, E. Y. *J. Am. Chem. Soc.* 2013, 135, 17683. Reis, S. A.; Ghosh, B.; Hendricks, J. A.; Szantai-Kis, D. M.; Tork, L.; Ross, K. N.; Lamb, J.; Read-Button, W.; Zheng. B.; Wang, H.; Salthouse, C.; Haggarty, S. J.; Mazitschek, R. *Nature Chemical Biology,* 2016, 12, 317, or Li, L.; Shen, X.; Xu, Q-H.; Yao, S. Q. *Angewandte Chemie Int. Ed.* 2015, 52, 424 or other references where synthesis and synthetic modifications of azobenzene derivatives are disclosed.

The starting materials or linking groups are generally known compounds or can be prepared by known procedures or obvious modifications thereof. Starting materials are available from commercial suppliers such as Millipore-Sigma. Alfa-Aesar/Fisher Scientific, VWR, Click Chemistry Tools, or others. Other materials can be prepared by procedures, or obvious modifications thereof, described in standard reference texts such as Larock's *Comprehensive Organic Transformations* (VCH Publishers Inc., 1989), or Organic Reactions, Volumes 1-40 (John Wiley and Sons, 1991).

Table of Abbreviations Used Herein

| | |
|---|---|
| Boc | tert-butyloxycarbonyl |
| CDI | carbonyldiimidazole |
| DBCO | dibenzylcyclooctyne |
| DMAP | 4-dimethylaminopyridine |
| DMF | N,N-dimethylformamide |
| EDCI | 1-ethyl-3-(3-dimethylaminopropyl)carbodiimide |
| ESI | Electrospray ionization |
| Et | ethyl |
| Fmoc | fluorenylmethyloxycarbonyl |
| HOBT | 1-hydroxybenzotriazole |
| Me | methyl |
| MS | |
| OAc | acetate |
| Ph | phenyl |
| Pr | propyl |
| Ts | p-toluenesulfonyl |
| Tris | tris(hydroxymethyl)aminomethane |

Scheme 1.
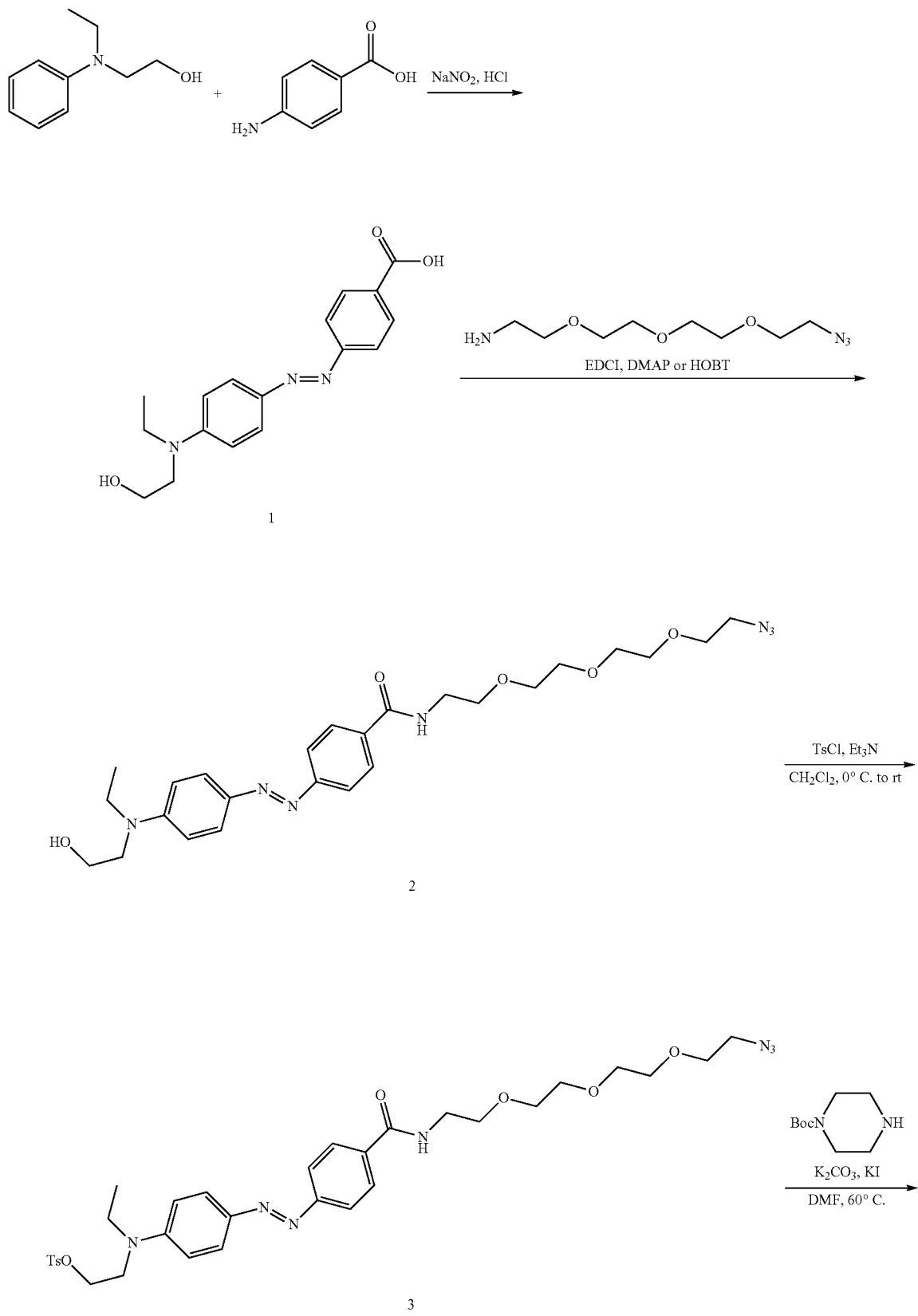

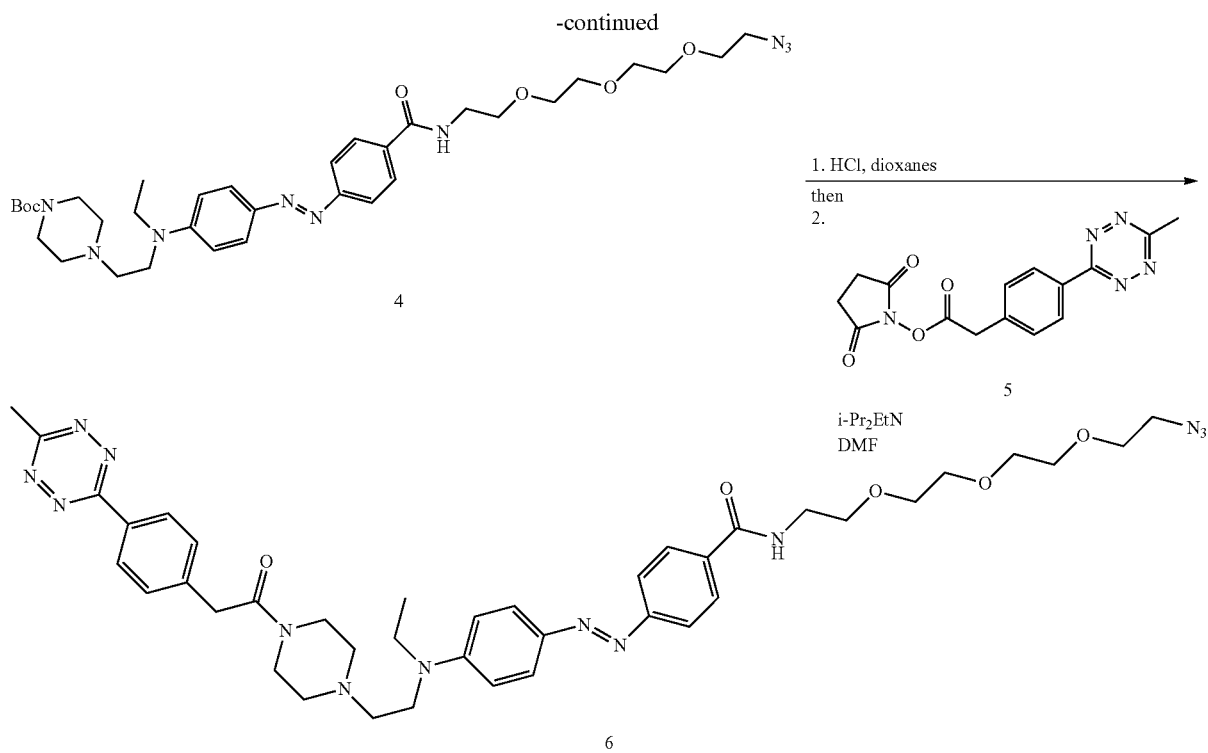

As shown in Scheme 1, a push-pull azobenzene can be synthesized by diazetization of an aniline (4-aminobenzoic acid is shown in the scheme as an example) and reaction with a sufficiently electron rich substituted benzene as described in Tuuttila, T.; Lipsonen, J.; Huuskonen, J.; Rissanen, K. Dyes and Pigments, 2009, 80, 34. Carbodiimide (EDCI)-mediated amide bond formation can be used to append an azide linked through a pegylated linker to afford amide 2. The free alcohol of 2 can be tosylated to activate it for a displacement reaction. Tosylated compound 3 can be treated with a mono-protected diamine (1-Boc-piperazine is used as an example) along with suitable base and heating to afford bifunctional compound 4, which contains both a masked amine and an azide functional group. 1-Boc-piperazine is used as an example; other mono-protected diamines consisting of either primary or secondary amine components can be used. The masked amine (Boc-protected amine) can be treated with a suitable acid such as hydrochloric acid to remove the Boc protecting group to provide the amine as the salt of the acid (in this case the hydrochloride salt), which can be subsequently elaborated by reaction with the N-hydroxysuccinimidyl ester of a desired linking group, for example, compound 5, to create an amide bond tethered to a methyl-substituted tetrazine. Examples of reacting primary or secondary amines with N-hydroxysuccinimidyl esters are numerous, for example in Thurber, G. M.; Yang, K. S.; Reiner, T.; Kohler, R. H.; Sorger, P.; Mitchison, T; Weissleder R. *Nature Communications* 2013, 4, 1504 or Yang, K. S.; Budin, G.; Reiner, T.; Vinegoni, C.; Weissleder R. *Angewandte Chemie Int. Ed.* 2012, 51, 6598. Other versions of activated carboxylic acids may be used in place of an N-hydroxysuccinimidyl ester, for example 4-nitrophenylcarbonate derivatives or pentafluorophenol derivatives. An unactivated carboxylic acid can also be reacted with compound 4 (or analogs thereof) after deprotection of the amine and in-situ activation of the unactivated carboxylic acid using peptide-coupling agents, for example carbodiimide reagents.

Scheme 2.

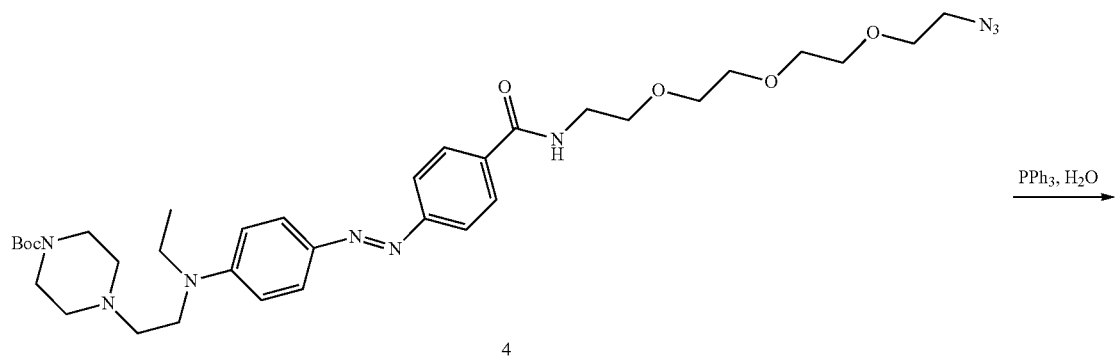

-continued

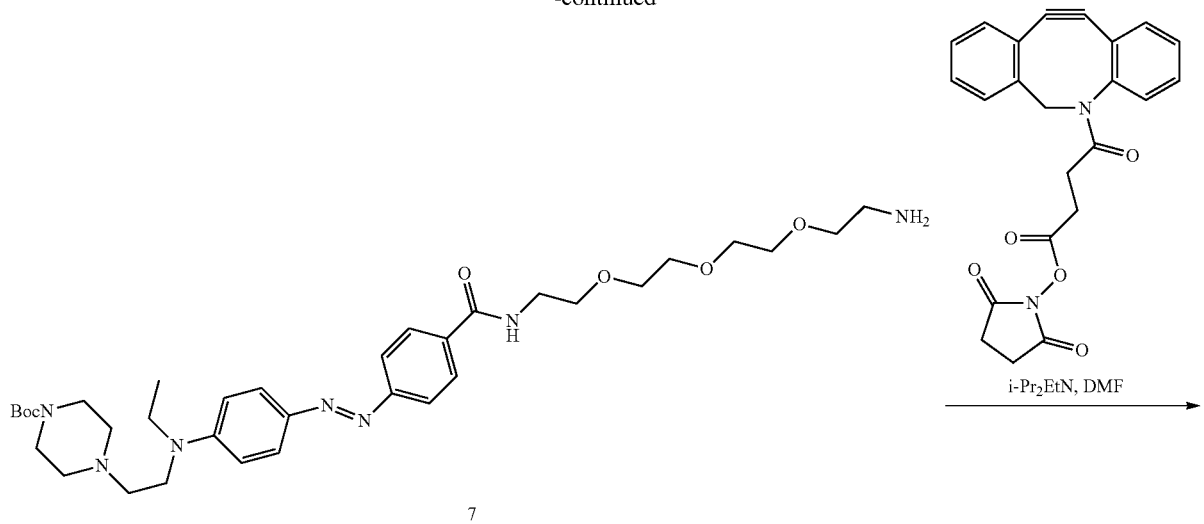

7

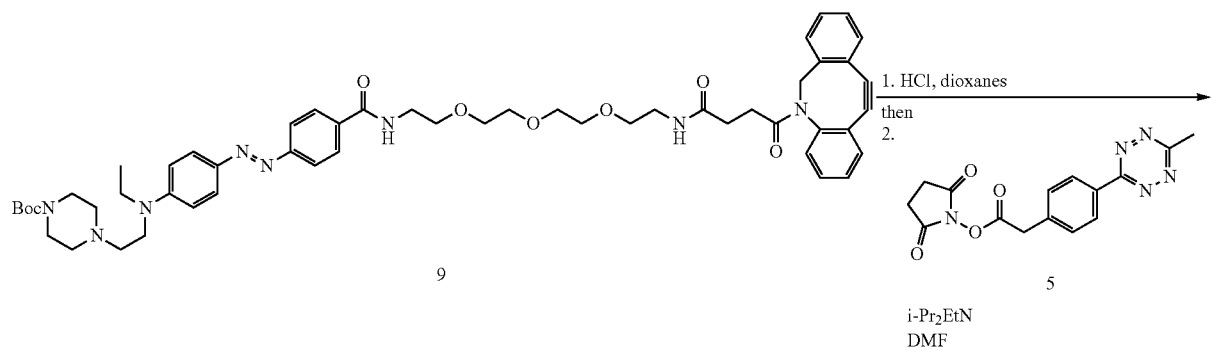

9

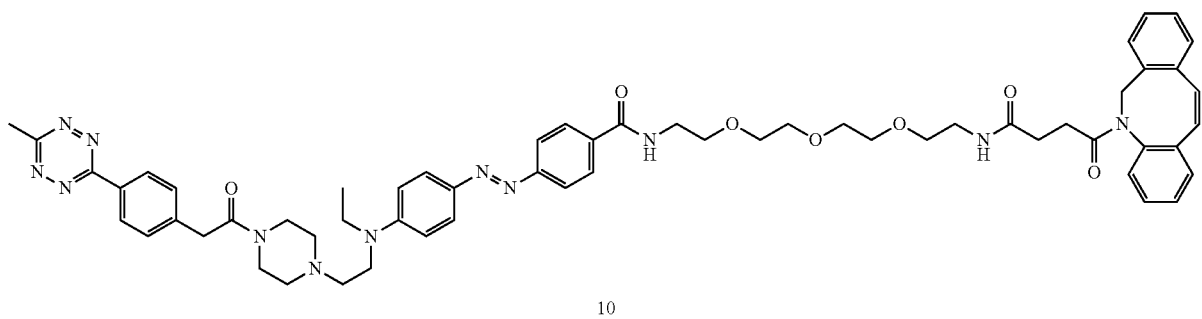

10

In Scheme 2, a compound with an azide and protected amine group such as 4 can be elaborated further to contain orthogonal click functionalities. The azide in compound 4 can be reduced to the amine using triphenylphosphine followed by hydrolysis of the resulting intermediate. The amine 7 can be reacted with an activated acid such as an N-hydroxysuccinimidyl ester tethered to a click functional group through a linker, such as an alkyl-tethered dibenzylcyclooctyne to form compound 8. The Boc-protected amine of compound 8 can be unmasked using hydrochloric acid and then reacted with an activated acid such as an N-hydroxysuccinimidyl ester to append an orthogonal click moiety, a tetrazine in the case of compound 10.

Scheme 3

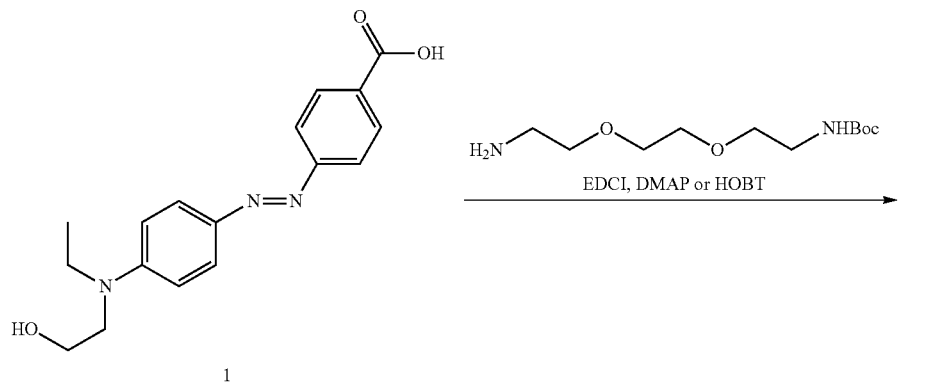

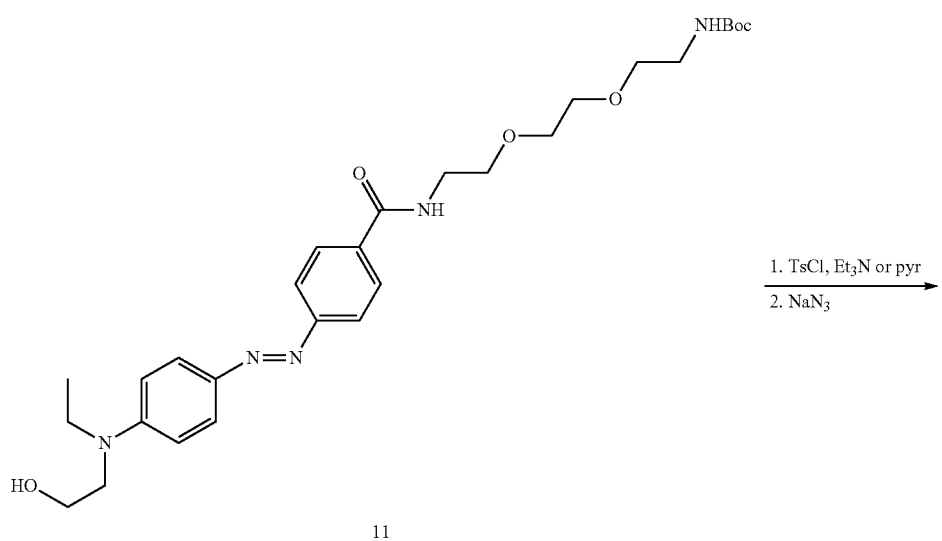

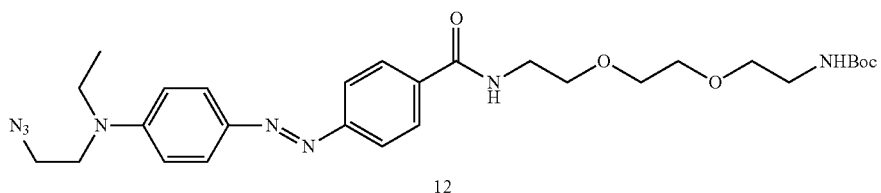

Scheme 3 shows another example of preparation of push-pull azobenzene having a clickable functional group (azide) and a protected amine (which can be unmasked and then reacted with activated carbonyl compounds to introduce other clickable functions. In this case, a representative mono-protected diamine (N-Boc-2,2'-(ethylenedioxy)diethylamine) can be reacted with the push-pull azobenzene (E)-4-((4-(ethyl(2-hydroxyethyl)amino)phenyl)diazenyl) benzoic acid via amide-bond forming methods such as carbodiimide-mediated amidation using EDCI. The free alcohol of compound 11 can activated as the tosylate and then displaced using sodium azide. The resulting azide of 12 can be used for click chemistry attachment to peptides or proteins or reduced to the free amine for further conjugation chemistries as described in Scheme 2. The Boc-protected amine can be converted to a free amine upon treatment with acid and then either reacted with a free carboxylic acid/carboxylate using carbodiimide-mediated conditions or reacted with an activated carboxylic acid (such as an N-hydroxysuccinimidyl ester).

Scheme 4

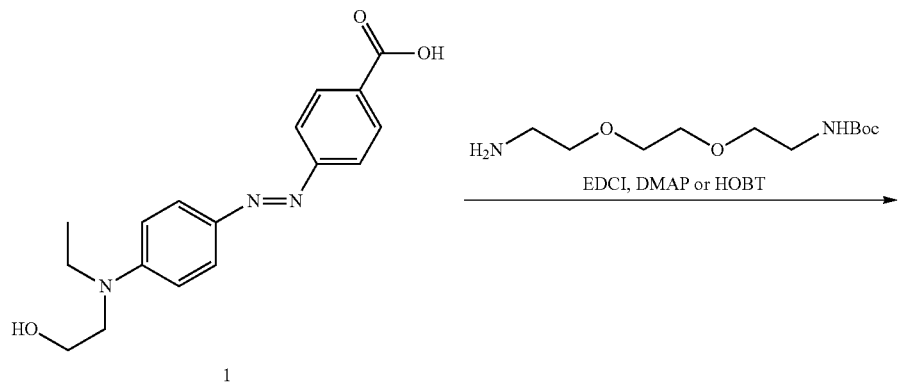

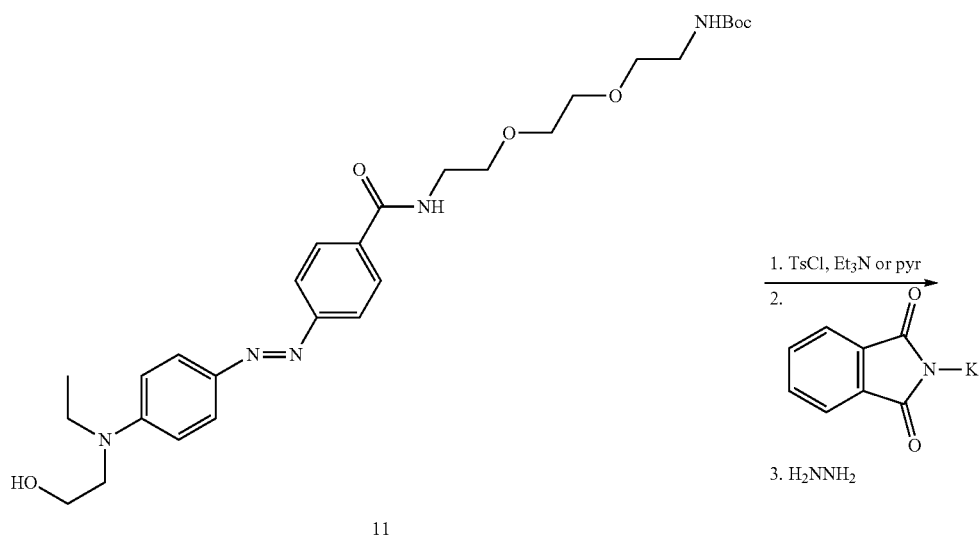

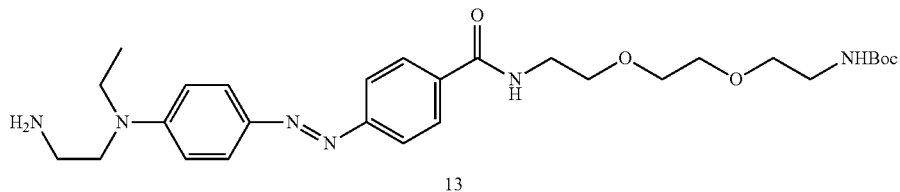

Scheme 4 shows a variant of Scheme 3 where the free alcohol of 11 is instead converted to an amine via activation with p-toluenesulfonyl chloride and reaction with the potassium salt of phthalimide, which can be reacted with hydrazine to produce an amine, analogous to the protocol described in Kienzler, M. A.; Reiner, A.; Trautman, E.; Yoo, S.; Trauner, D.; isacoff, E. Y. *J. Am. Chem. Soc.* 2013, 135, 17683.

Scheme 5

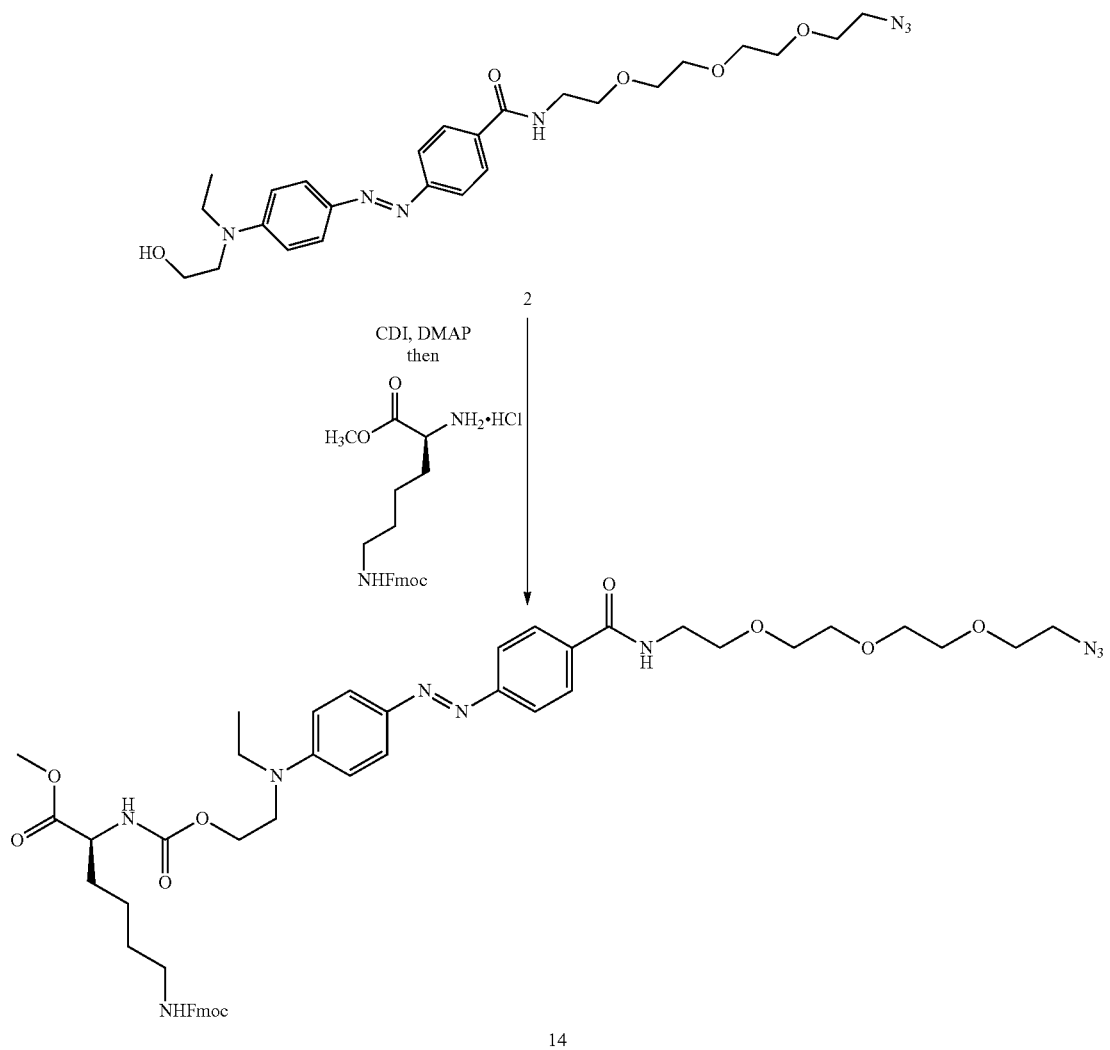

Scheme 5 shows an example of elaborating a clickable diazobenzene derivative 2 via a carbamate linkage. In this example, the free alcohol of 2 is activated with carbonyldiimidazole and then reacted with L-lysine-N^ε-Fmoc-methyl ester hydrochloride to form carbamate 14. Similarly, carbamates could be formed using amines tethered to orthogonal click groups, such as an amine tethered to a tetrazine via either an alkyl or a PEG-chain linker.

Scheme 6

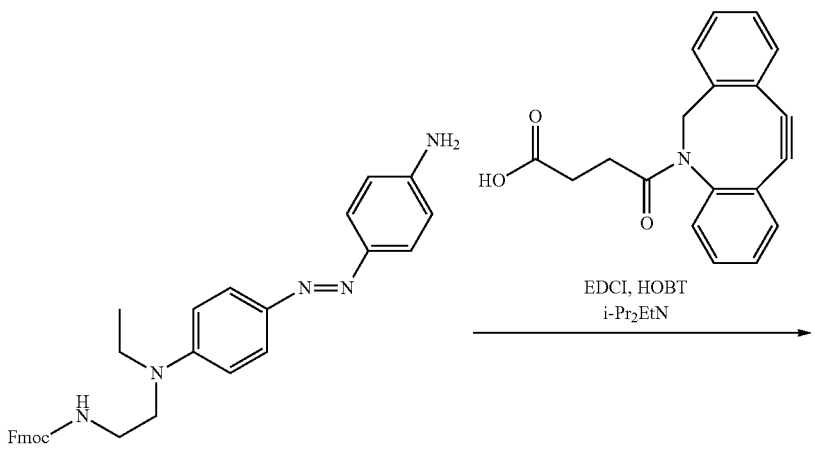

-continued

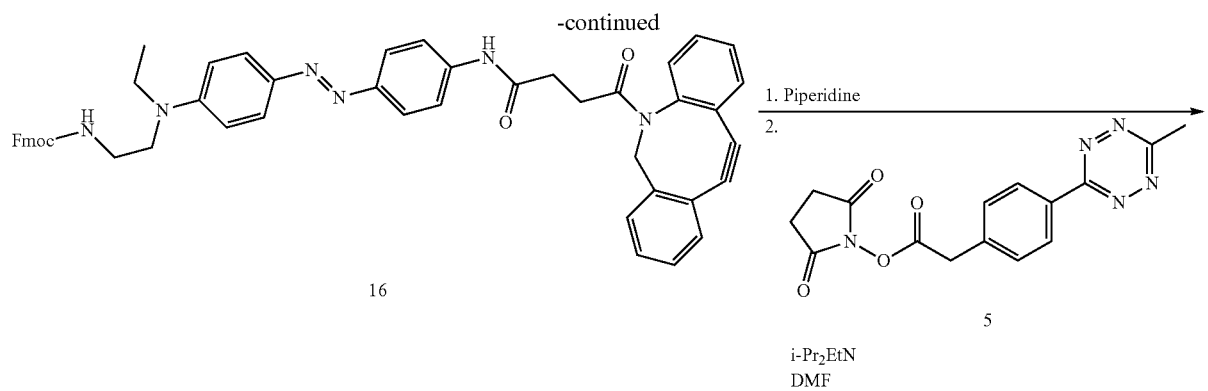

16

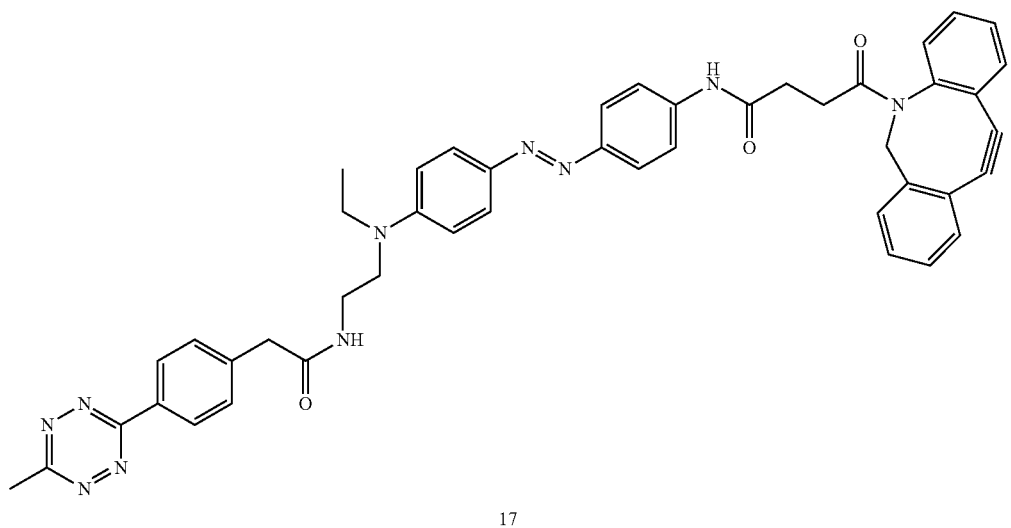

17

Scheme 6 shows an alternative push-pull azobenzene core 15 described in Kienzler, M. A.; Reiner, A.; Trautman, E.; Yoo, S.; Trauner, D.; isacoff, E. Y. *J. Am. Chem. Soc.* 2013, 135, 17683. The azobenzene can be elaborated with click moieties by carbodiimide mediated coupling with an acid, for example, the succinylated dibenzylcyclooctyne shown in Scheme 6, to afford compound 16. Treatment of 16 with piperidine to remove the Fmoc protecting group followed by reaction of the resulting amine with an N-hydroxysuccinimidyl ester tethered to an orthogonal click group (in this case, a tetrazine) would afford a bifunctional push-pull azobenzene 17.

Azobenzene Molecules

The compounds and/or intermediates were characterized by nuclear magnetic resonance spectroscopy (NMR) on a Bruker Avance III 400 MHz NMR Spectrometer. Chemical shifts (δ) are reported in ppm using the following convention: chemical shift, multiplicity (s=singlet, d=doublet, t=triplet, q=quartet, m=multiplet, br=broad), coupling constants, and integration. Spectra are referenced to residual chloroform (7.27 ppm) or residual dimethylsulfoxide (2.50 ppm). Mass spectrometric analysis was performed on an Agilent 1260 Infinity instrument with an Agilent 6120 Quadropole MS. Separations were performed using an Agilent Eclipse XDB-C18 column (5 μm, 4.6×250 mm) using a gradient (10-95% methanol in water with 0.1% formic acid added at a flow rate of 0.7 mL/min. Compounds were detected by UV absorption at 210 nm or 254 nm; Molecular weight range 400-2000; capillary voltage 3750 (pos) and 3500 (neg). Analytical thin-layer chromatography (TLC) was performed on pre-coated silica gel 60 F-254 plates (particle size 0.040-0.050 mm, 230-400 mesh) and visualization was accomplished with UV, visual inspection, or potassium permanganate solutions.

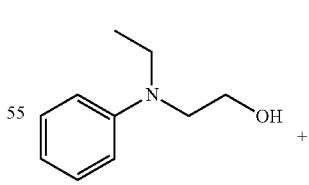

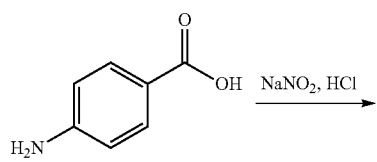

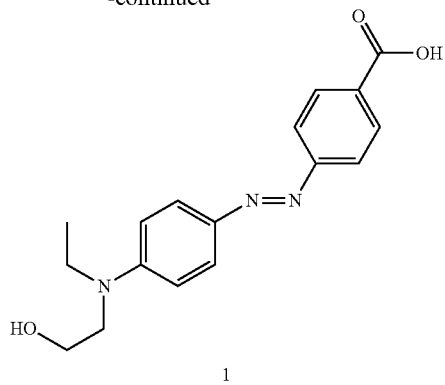

1

Protocol for Preparation of (E)-4-((4-(ethyl(2-hydroxyethyl)amino)phenyl)diazenyl)benzoic acid (1). The core structure of the diazobenzene photoswitch 1 was synthesized according to the protocol reported in Tuuttila, T.; Lipsonen, J.; Huuskonen, J.; Rissanen, K. Dyes and Pigments, 2009, 80, 34. The synthesis is accomplished by diazetization of 4-aminobenzoic acid using hydrochloric acid and sodium nitrite; the resulting solution is then added to a solution of N-ethyl-N-(2-hydroxy)aniline. The resulting azobenzene 1 is isolated as a red solid after neutralization and filtration: $^1$H NMR DMSO-d$_6$, 400 MHz) δ 12.86 (br s, 1H), 8.06 (d, J=8.8 Hz, 2H), 7.82 (d, J=8.5 Hz, 2H), 7.80 (d, J=9.1 Hz, 2H), 6.85 (d, J=9.3 Hz, 2H), 4.83 (br s, 1H), 3.60 (t, J=6.3 Hz, 2H), 3.55-3.47 (m, 4H), 1.15 (t, J=7.0 Hz, 3H); MS (ESI) m/z calc for C17H20N3O3 [M+H]$^+$ 314.15 found 314.2, In pH 7.9 Tris-acetate buffer, λmax=464 nm, ε=33,500 M$^{-1}$cm$^{-1}$ Protocol for preparation of (E)-N-(2-(2-(2-(2-azidoethoxy)ethoxy)ethoxy)ethyl)-4-((4-(ethyl(2-hydroxyethyl)amino)phenyl)diazenyl)benzamide (2): A solution of 1 (200 mg, 0.638 mmol) and azide-PEG3-amine 3 (278 mg, 1.28 mmol) in anhydrous N,N-dimethylformamide (DMF) (3.0 mL) was treated with 4-dimethylaminopyridine (DMAP) (171 mg, 1.40 mmol) and EDCI-HCl (245 mg, 1.28 mmol) and stirred at room temperature for 16-24 hours. The reaction mixture was diluted with CH$_2$Cl$_2$ and washed with 0.1 M citric acid (aq), 0.1 M NaHCO$_3$ (aq), water, and brine, dried (MgSO$_4$), filtered, and concentrated in vacuo to afford crude 2 (216 mg, 66%; yield based on crude mass and $^1$H NMR ratios with remaining DMF).

$^1$H NMR (400 MHz, DMSO-d6) δ 8.61 (t, J=5.6 Hz, 1H), 7.99 (d, J=8.6 Hz, 2H), 7.81 (d, J=8.6 Hz, 2H), 7.80 (d, J=9.1 Hz, 2H), 6.85 (d, J=9.3 Hz, 2H), 4.83 (t, J=5.1 Hz, 1H), 3.64-3.49 (m, 16H), 3.49-3.34 (m, 6H), 1.16 (t, J=1.16 Hz, 3H) MS (ESI) m/z calc for C25H36N7O5 [M+H]$^+$ 514.28 found 514.2.

In pH 7.9 Tris-acetate buffer, λmax=472 nm, ε=32,260 M$^{-1}$cm$^{-1}$

Protocol for preparation of (E)-2-((4-((4-((2-(2-(2-(2-azidoethoxy)ethoxy)ethoxy)ethyl)carbamoyl)phenyl)diazenyl)phenyl)(ethyl)amino)ethyl 4-methylbenzenesulfonate (3): Crude 2 (0.638 mmol assuming complete conversion) was dried via coevaporation with toluene and then taken up in CH$_2$Cl$_2$ (4 mL) and treated with Et$_3$N (350 μL, 2.51 mmol) under N$_2$ atmosphere. The solution was cooled to 0° C. in an ice-water bath and maintained for 15 min. A solution of p-toluenesulfonyl chloride (TsCl) in CH$_2$Cl$_2$ (0.8 mL) was added dropwise. The reaction mixture was stirred overnight (15 hours), gradually warming to room temperature. The mixture was diluted with CH$_2$Cl$_2$, washed with water (3×), dried (MgSO$_4$), filtered, and concentrated in vacuo. Purifi-

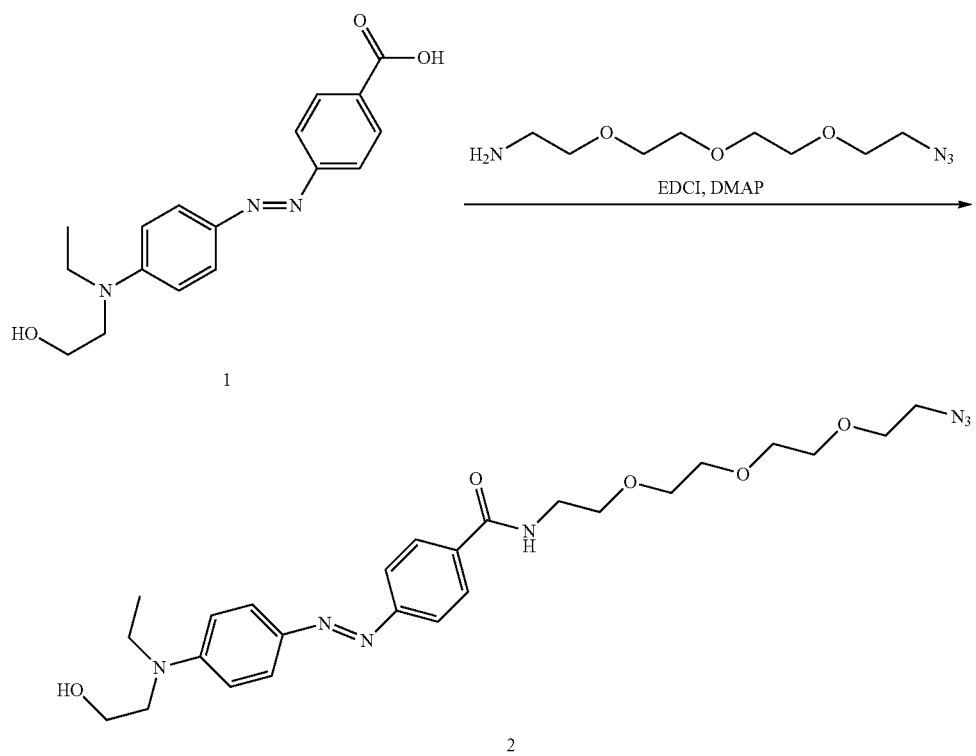

cation by chromatography on SiO$_2$ (500% ethyl acetate/hexanes to 70% ethyl acetate/hexanes to 90% ethyl acetate/hexanes) afforded 3 as a red oil that solidified upon drying by coevaporation with toluene, 180 mg, 42% yield over two steps: $^1$H NMR (400 MHz, DMSO-d6) δ 8.62 (t, J=5.6 Hz, 1H), 8.01 (d, J=8.5 Hz, 2H), 7.83 (d, J=8.4 Hz, 2H), 7.74 (d, J=9.0 Hz, 2H), 7.70 (d, J=8.1 Hz, 2H), 7.37 (d, J=7.9 Hz, 2H), 6.73 (d, J=9.0 Hz, 2H), 4.20 (t, J=5.3 Hz, 2H), 3.71 (t, J=5.4 Hz, 2H), 3.59 (t, J=5.0 Hz, 2H), 3.58-3.53 (m, 10H), 3.51-3.42 (m, 2H), 3.40-3.37 (m, 4H), 2.34 (s, 3H), 1.08 (t, J=7.0 Hz, 3H); MS (ESI) m/z calc for C32H41N7NaO7S [M+Na]$^+$ 690.27, found 690.2.

DMF (1.6 mL) was treated with 1-Boc-piperazine (89 mg, 0.48 mmol), KI (5.3 mg, 0.032 mmol), and K$_2$CO$_3$ (66 mg, 0.48 mmol). The solution was sparged with N$_2$, sealed, and heated at 60° C. for 4 h. Upon cooling, the mixture was partitioned between CH$_2$Cl$_2$ and water, and the aqueous layer was extracted with CH$_2$Cl$_2$. The combined organic layers were washed with water and brine, dried (MgSO$_4$), filtered, and concentrated in vacuo. Purification on SiO$_2$ (100% CH$_2$Cl$_2$, then CH$_2$Cl$_2$:MeOH:Et$_3$N, 95:4:1) afforded a mixture of the product 4: MS m/z (ESI) calc for C34H52N9O6 [M+H]$^+$ 682.40, found 682.4 along with a

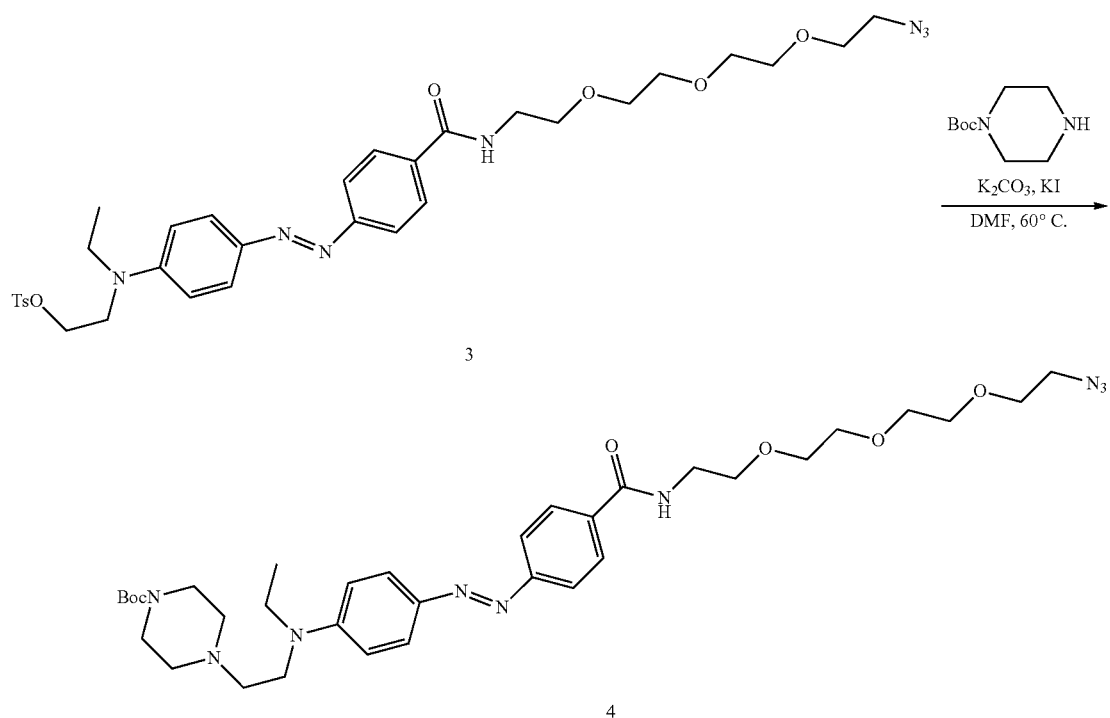

Protocol for preparation of tert-butyl (E)-4-(2-((4-((4-((2-(2-(2-(2-azidoethoxy)ethoxy)ethoxy)ethyl)carbamoyl)phenyl)diazenyl)phenyl)(ethyl)amino)ethyl)piperazine-1-carboxylate (4): A solution of 3 (0.160 mmol) in anhydrous byproduct with m/z 726.4 and 748.3, presumably [M+H]$^+$ and [M+Na]$^+$, respectively. Follow-on experiments using acetonitrile as a solvent seemed to suppress byproduct formation. Note: This protocol is unoptimized.

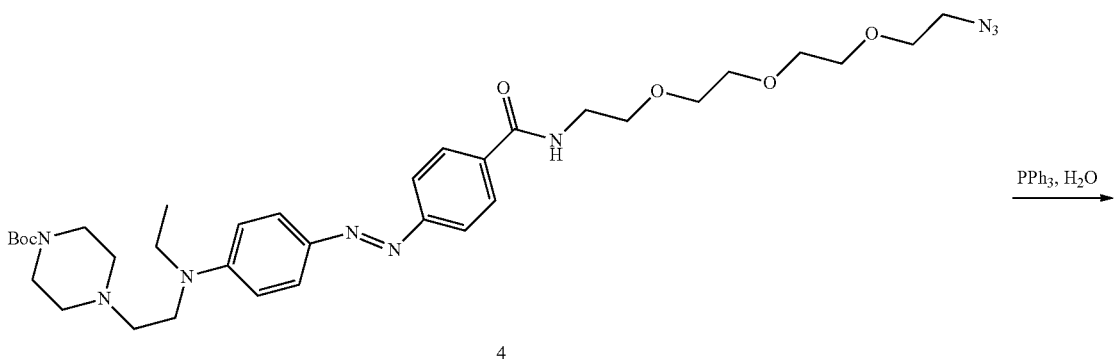

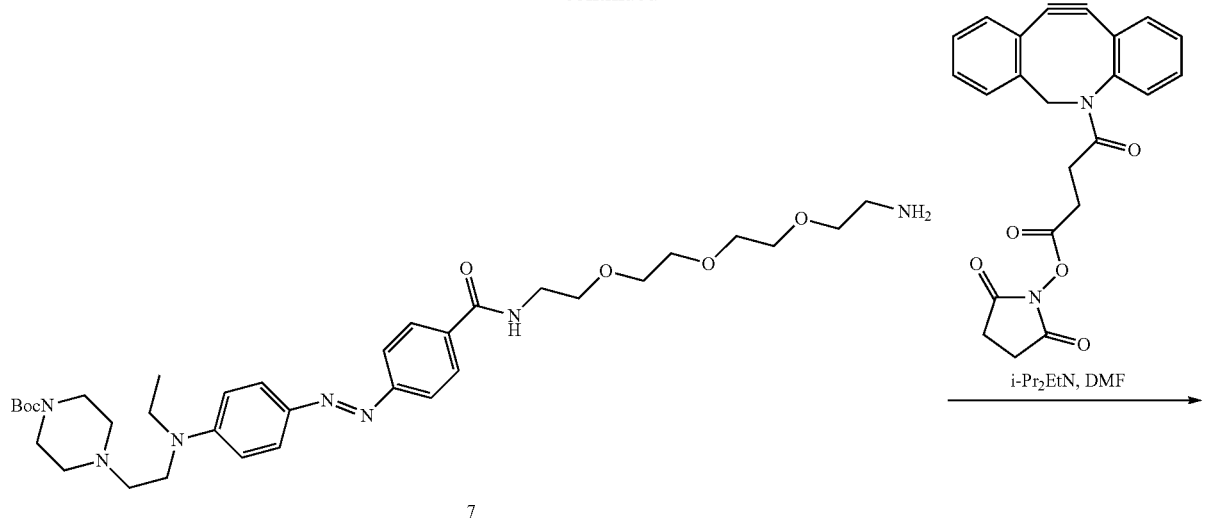

7

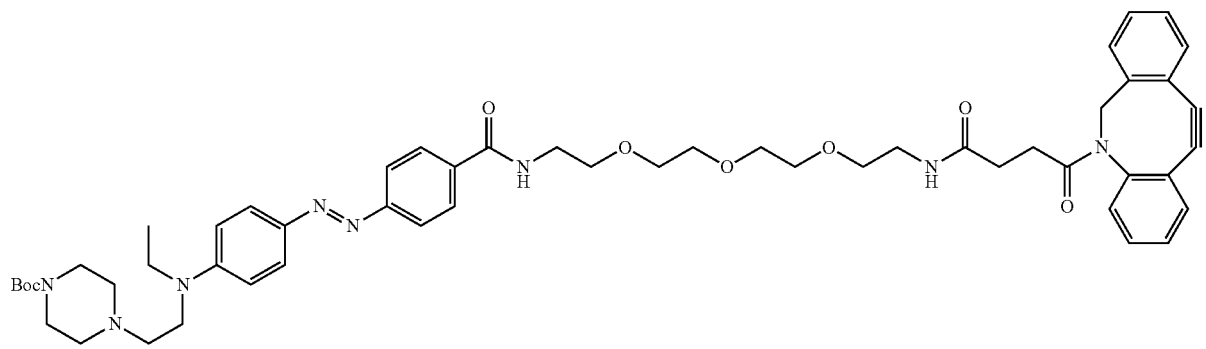

9

Protocol for preparation of compound 9. The mixed fractions obtained from preparation of compound 4 were taken up in tetrahydrofuran (THF) (1 mL) and treated with PPh$_3$ (50 mg, 0.19 mmol) and stirred overnight at room temperature. Water (50 μL) was added, and the mixture was incubated for an additional 6 h, after which the mixture was diluted with ethyl acetate. MgSO$_4$ was added, and the mixture was filtered and concentrated in vacuo to afford 71 mg crude material (~0.1 mmol). The crude mixture was coevaporated with toluene and then taken up in anhydrous DMF (1.0 mL) and treated with DBCO-NHS (42 mg, 0.10 mmol) and N,N-diisopropylethylamine (35 μL, 0.20 mmol) and stirred at room temperature overnight (16 h). The solvent was removed in vacuo and the crude residue was purified by chromatography on SiO$_2$ (100% CH$_2$Cl$_2$ to 5% MeOH/CH$_2$Cl$_2$) with 1% Et$_3$N added to 10% MeOH/CH$_2$Cl$_2$ with 1% Et$_3$N added) to afford 5 as an orange solid (14 mg, 0.015 mmol based on having 0.1 mmol starting material, ~15% overall yield). 1H NMR (400 MHz, Chloroform-d) δ 7.93-7.84 (m 6H), 7.59-7.44 (m, 1H), 7.55-7.51 (m, 1H), 748-7.21 (m, 6H), 7.15 (d, J=4.8 Hz, 1H), 6.79 (d J=8.9 Hz, 2H), 6.26 (s, 1H), 5.14 (d, J=13.9 Hz, 1H), 3.77-3.53 (m, 17H), 3.50-3.42 (m, 6H), 2.86 (m, 1H), 2.63 (t, J=7.5 Hz, 1H), 2.54-2.36 (m, 8H), 2.24-1.90 (m, 1H), 1.98-1.91 (m, 1H), 1.48 (s, 9H), 1.31-1.22 (m, 3H) MS (ESI) m/z calc for C53H67N8O8 [M+H]$^+$ 943.51, found 943.4.

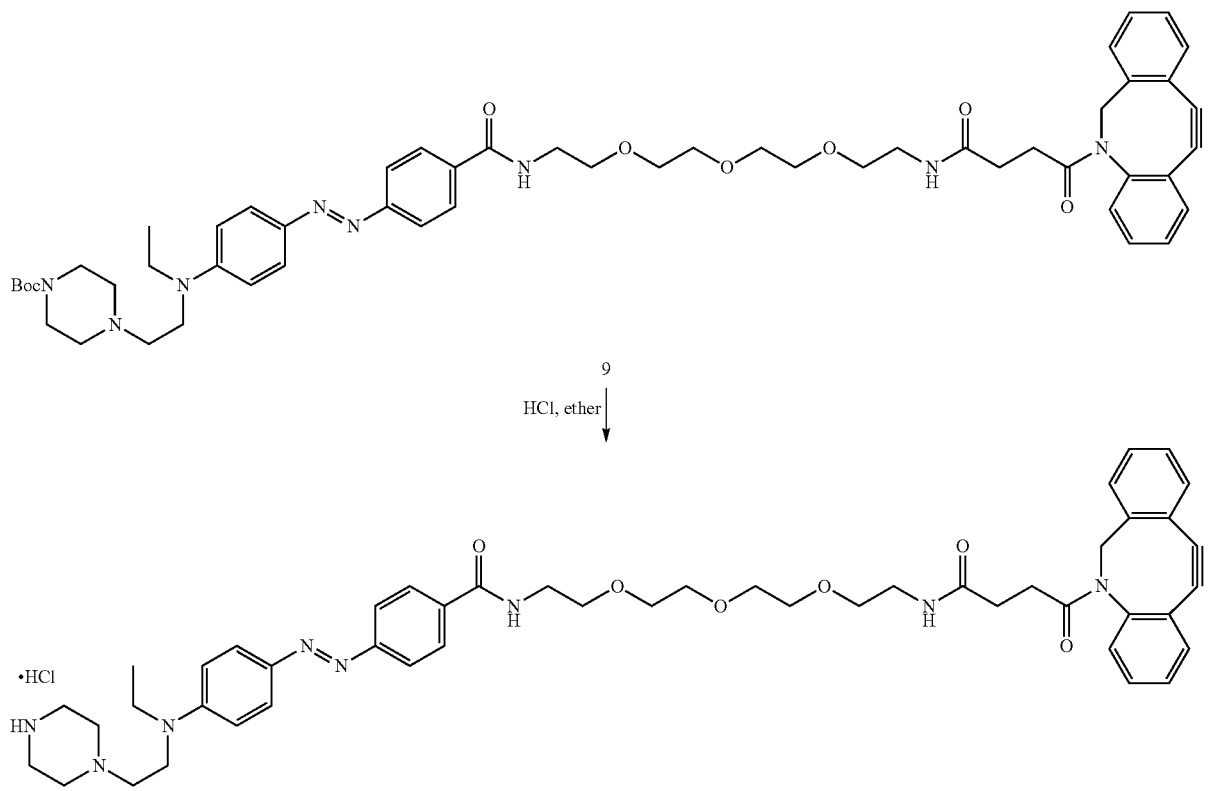

9 | HCl, ether

Procedure for Removing Boc Protecting Group: To remove the Boc protecting group from compound 5; Compound 5 (5.3 mg) was treated with 2 M HCl in diethyl ether. The compound immediately turned purple, but solubility was poor. Ethyl acetate was added, but still solubility was not sufficient for complete conversion. Partial conversion of the Boc-protected piperazine to the N—H product was observed by mass spectrometry analysis MS (ESI) m/z calc for $C_{48}H_{59}N_8O_6$ $[M+H]^+$ 843.46, found 843.63.

Alternatively, a functional group tether can be attached to the push-pull diazobenzene via forming a carbamate linkage.

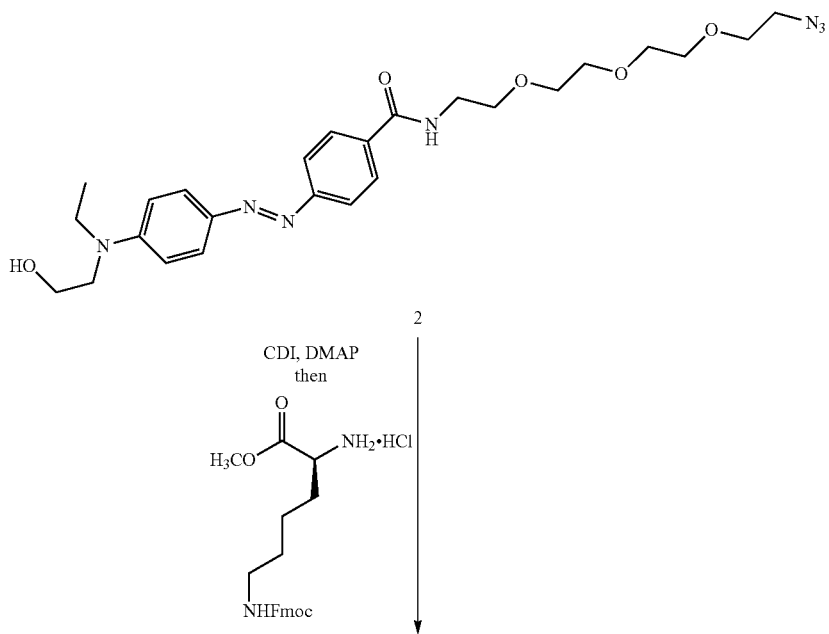

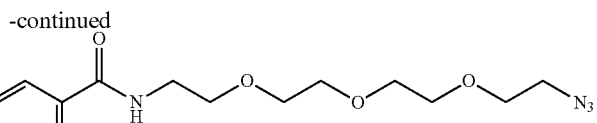
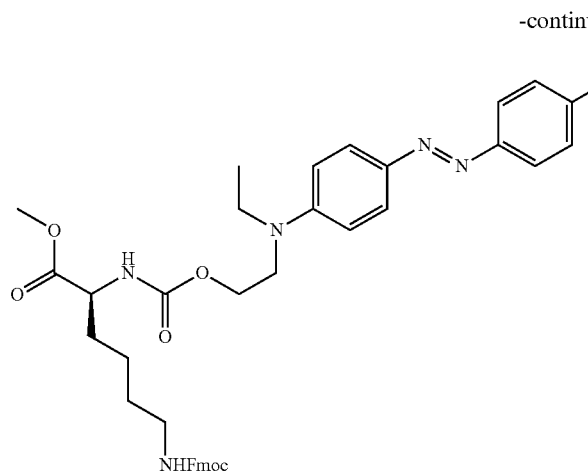

14

Procedure for carbamate formation using 2 as a substrate: An oven-dried flask equipped with stir bar under Ar atmosphere was charged with a solution of 2 (208 mg, ~80% purity, ~0.32 mmol) in anhydrous THF (3.5 mL) followed by carbonyldiimidazole (CDI) (98 mg, 0.60 mmol) and DMAP 4.0 mg, 0.032 mmol). The solution was stirred at room temperature for 2 h, then L-lysine-N$^\varepsilon$-Fmoc-methyl ester hydrochloride (252 mg, 0.604 mmol) was added, and the mixture was stirred overnight. The reaction mixture was diluted with water, then extracted with methyl tert-butyl ether (MBTE), then extracted with ethyl acetate. The combined organic layers were dried with MgSO$_4$, filtered, and concentrated in vacuo. Purification by chromatography on SiO$_2$ (2% MeOH/EtOAc to 2% MeOH/EtOAc with 1% triethylamine added) afforded 7. A fraction was taken for characterization: R$_f$ (2% Methanol/Ethyl Acetate) 0.57; 1H NMR (400 MHz, DMSO-d6) δ 8.62 (t, J=5.7 Hz, 1H), 7.99 (d, J=8.3 Hz, 2H), 7.89 (d. J=7.5 Hz, 2H), 7.84-7.77 (m, 4H), 7.68 (d, J=7.6 Hz, 2H), 7.41 (t, J=7.5 Hz, 2H), 7.33 (t, J=7.4 Hz, 2H), 7.25 (br s, 1H), 6.88 (d, J=8.9 Hz, 2H), 4.30 (m, 2H), 4.25-4.14 (m, 2H), 4.03 (p, J=7.1 Hz, 2H), 3.65-3.48 (m, 16H), 3.48-3.34 (m, 4H), 3.37 (t, J=4.9 Hz, 2H), 2.97-2.94 (m, 2H), 1.67-1.55 (m, 2H), 1.37-1.24 (m, 2H), 1.20-1.14 (m, 5H); MS (ESI) m/z calc for C48H60N9O10 [M+H]$^+$ 921.44, Example 13: Bifunctional Photoswitches Some embodiments utilize a multifunctional, e.g., bifunctional, photoswitch. Its structure is designed to have orthogonal clickable moieties at each end, each reacting with the complementary click moiety introduced, for instance, as an artificial amino acid. Click chemistries such as described above can be independently selected to link the end moieties within a larger structure, TdT, for example. Thus, in various implementations, the clickable moieties at the two ends of a bifunctional photoswitch are the same or different from one another. The complementary reactive group can be selected independently as well. In many cases, tetrazine moieties at both ends of a bifunctional photoswitch can be linked to the same counterpart moiety (trans-cyclooctene, for example). If desired, synthesis schemes can be developed for having one tetrazine end moiety react with trans-cyclooctene and the other with norbornene.

The multi-functional photoswitch can comprise, e.g., a reactive moiety on each side (e.g., methanesulfonylthioates, disulfides, or maleimides that react with selenocysteine or cysteine residues that are appropriately positioned in the enzyme).

Combinations of reactive moieties and clickable moieties in the same multifunctional photoswitch also can be utilized. Alternatively, a multi-functional photoswitch could have two orthogonal reactive groups Click Reactive Group A and Click Reactive Group B, which will react separately with a Click Reactive Group A' on a peptide and a Click Reactive Group B' on an enzyme. (see FIG. 28). The peptide can function as a structural element to block nucleotide entry through steric or other conformational changes. The peptide can also function as a tag for affinity purification of the peptide-diazobenzene-protein structure. Example affinity tag peptides include HIS-6, Glutathione, FLAG, c-Myc, HA, V5, Xpress, Biotin acceptor domain (BAD), VSVG, protein c, or S-tag. Resins for column-based affinity purification of these affinity tags are commercially available from vendors such as Thermo Fisher or Sigma Aldrich and affinity purification is carried out according to vendor instructions. Any peptide sequence has the potential to be used as an affinity tag for purification by identifying an antibody that is specific to that peptide. This can enable the use of any peptide sequence that is identified to improve the photocontrol of the enzyme for affinity purification.

Figure 28:
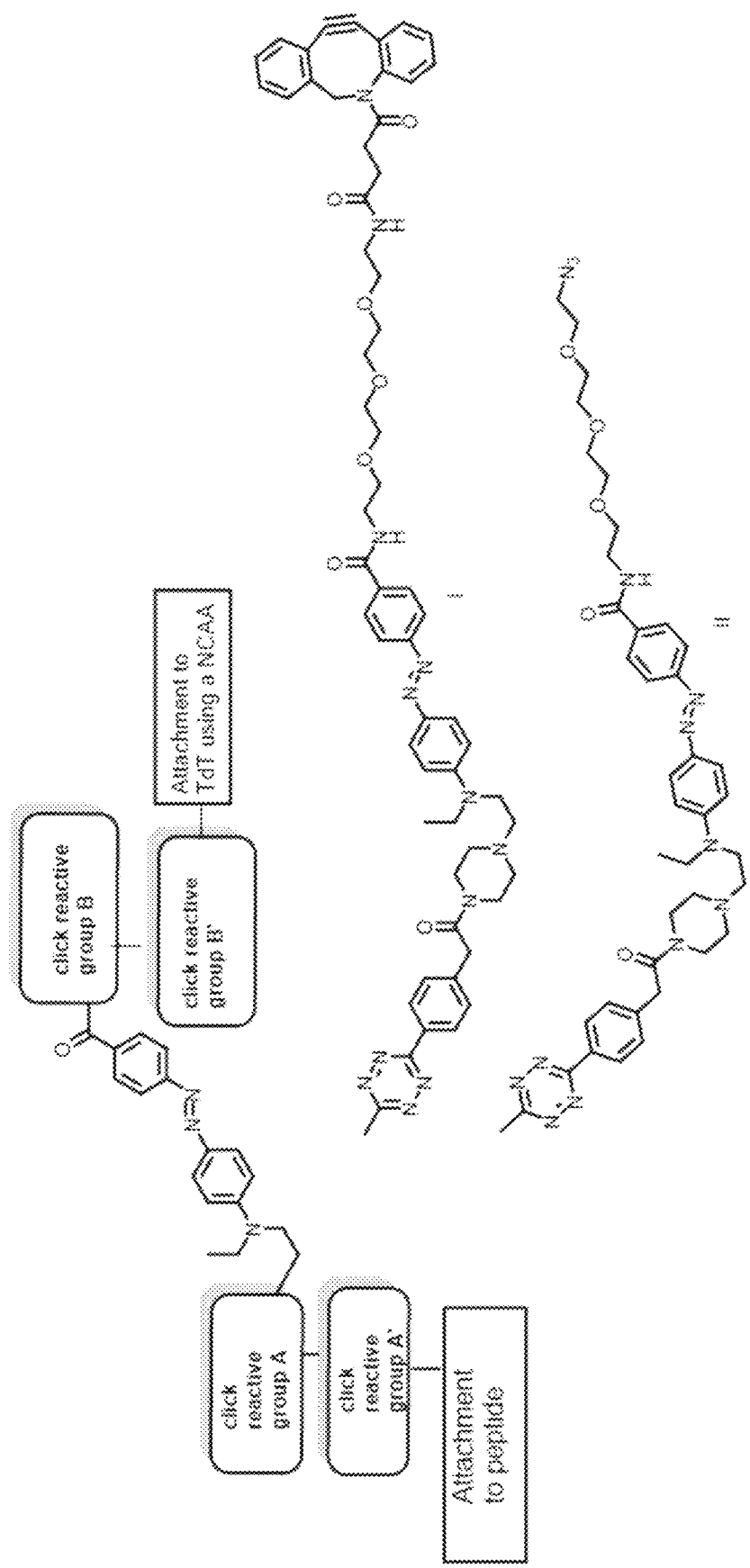
FIG. 28 depicts a multifunctional photoswitch.

Click Reactive Group A and Click Reactive Group A' refer to complementary click chemistries that will react to form new bonds while being orthogonal in reactivity to Click Reactive Group B and Click Reactive Group B', which also represent complementary click chemistries that will react to rom new bonds with each other while being orthogonal to Click reactive group A and click reactive group A.' Examples of orthogonal reactive groups are given in Table 1. Structures I and II of FIG. 28 are example diazobenzene molecules that contain a Click Reactive Group A and a Click Reactive Group B; I contains a methyl tetrazine and a DBCO (dibenzylcyclooctyne, which will react with a trans-cyclooctene and an azide, respectively. II contains a methyl tetrazine and an azide, which will react with an alkyne and a trans-cyclooctene, respectively. The orthogonality of the azide/DBCO and tetrazine/TCO click chemistries is described in Karver, M. R.; Weissleder, R.; Hilderbrand, S. A. Angewandte Chemie Int. Ed. 2012, 51, 920. Table 1 lists examples of click chemistries, but other click chemistries or bioconjugation chemistries can be used. Suitable click chemistries or bioconjugation chemistries are described in Patterson, D. M.; Nazarova, L. A.; Prescher, J. A. *ACS Chemical Biology* 2014, 9, 592.

Conjugation of small molecules to peptides can be accomplished via standard amidation chemistry wherein an amine moiety on the small molecule reacts with an in-situ carboxylic acid group on the peptide. A stable, activated carboxylic acid group on the peptide can be generated by first converting the carboxylic acid to a stable, activated ester, for example an N-hydroxysuccinimidyl ester, a pentafluorophenol ester, or a p-nitrobenzyl carbonate. Alternatively, the small molecule can contain a carboxylic acid which can react with an amine on a peptide via the chemistry described for the converse case. The small molecule can also contain a maleimide moiety which can react with a free thiol group on a peptide, for example, to a cysteine residue. Typical protocols for amidation reactions and the thiol-maleimide conjugation are known to those skilled in the art and are detailed in *Bioconjugate Techniques* $3^{rd}$ ed. (Academic Press 2013). Small molecules can also be conjugated to peptides using click chemistry, either through an azide on a small molecule reacting with an alkyne on the peptide through copper mediated click chemistry or through copper-free click chemistry or through an alkyne on the small molecule reacting with an azide on a peptide. The small molecule can also be conjugated to the peptide via reaction of a tetrazine on the small molecule with a trans-cyclooctene (TCO) on the peptide or via reaction of a trans-cyclooctene on the small molecule with a tetrazine on the peptide. Use of azide/alkyne click chemistry for small molecule conjugation to peptides is in Clardy, S. M.; Keliher, E. J.; Mohan, J. F.; Sebas, M.; Benoist, C.; Mathis, D.; Weissleder R. *Bioconjugate Chemistry* 2014, 25, 171 and/or Loh, Y.; Shi, H.; Hu, M.; Yao, S.-Q. Chemical Communications 2010, 46, 8407 and use of tetrazine/trans-cyclooctene click chemistry is in Zeglis, B. M.; Emmetiere, F.; Pillarsetty, N.; Weissleder, R.; Lewis, J. S.; Reiner, T. *ChemistryOpen* 2014, 3, 48.

The peptide-diazobenzene conjugate can be reacted with a protein via click chemistry with a non-canonical amino acid that is incorporated into the protein. The non-canonical amino acid (NCAA) can contain a click moiety that contains a complementary click moiety. For example, the protein can contain a trans-cyclooctene, which will react with a tetrazine on the small molecule-peptide conjugate. Click chemistry conjugation of small molecules or peptide-small molecule conjugates are described in Pickens, C. J.; Johnson, S. N.; Pressnall, M. M.; Leon, M. A.; Berkland, C. J. *Bioconjugate Chemistry* 2018, 29, 686 and references therein and/or Rashidian, M.; Keliher, E.; Dougan, M.; Juras, P. K.; Cavallari, M.; Wojtkiewicz, G. R.; Jacobsen, J.; Edens, J. G.; Tas, J. M.; Victora, G.; Weissleder, R.; Ploegh, H. *ACS Central Science* 2015, 1, 142.

Figure 16:
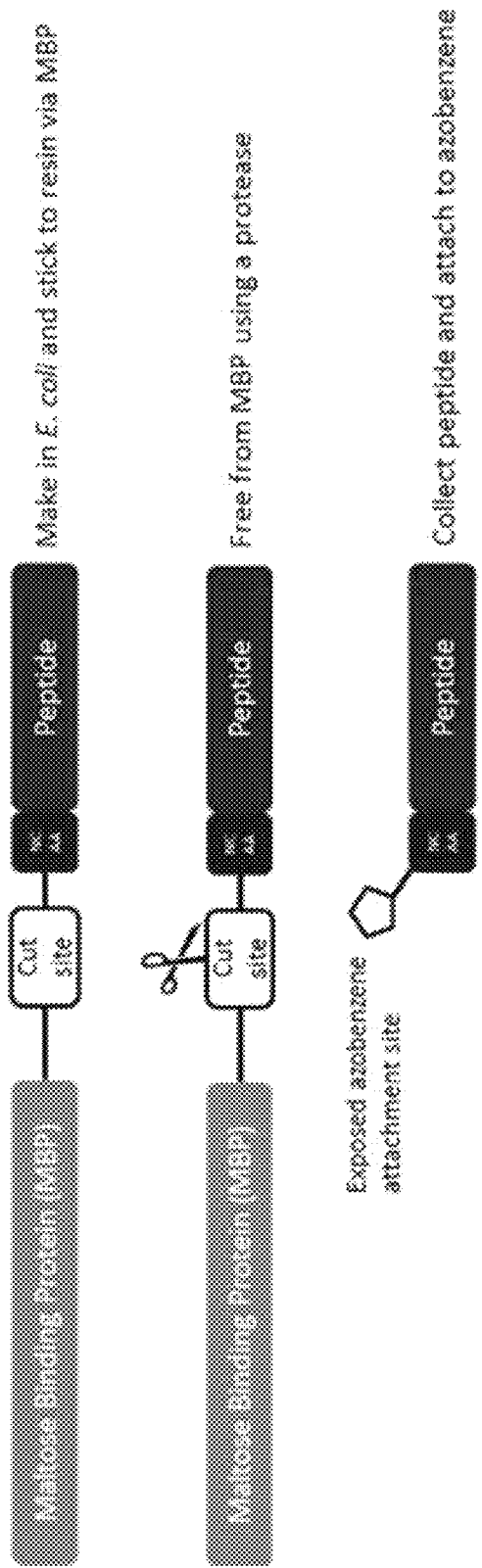
FIG. 16 is a schematic showing a method for producing and purifying NCAA-containing peptides that can be chemically coupled to azobenzene molecules. The peptide is synthesized as a fusion to maltose binding protein to improve solubility and enable facile purification.
Figures 17A, 17B:
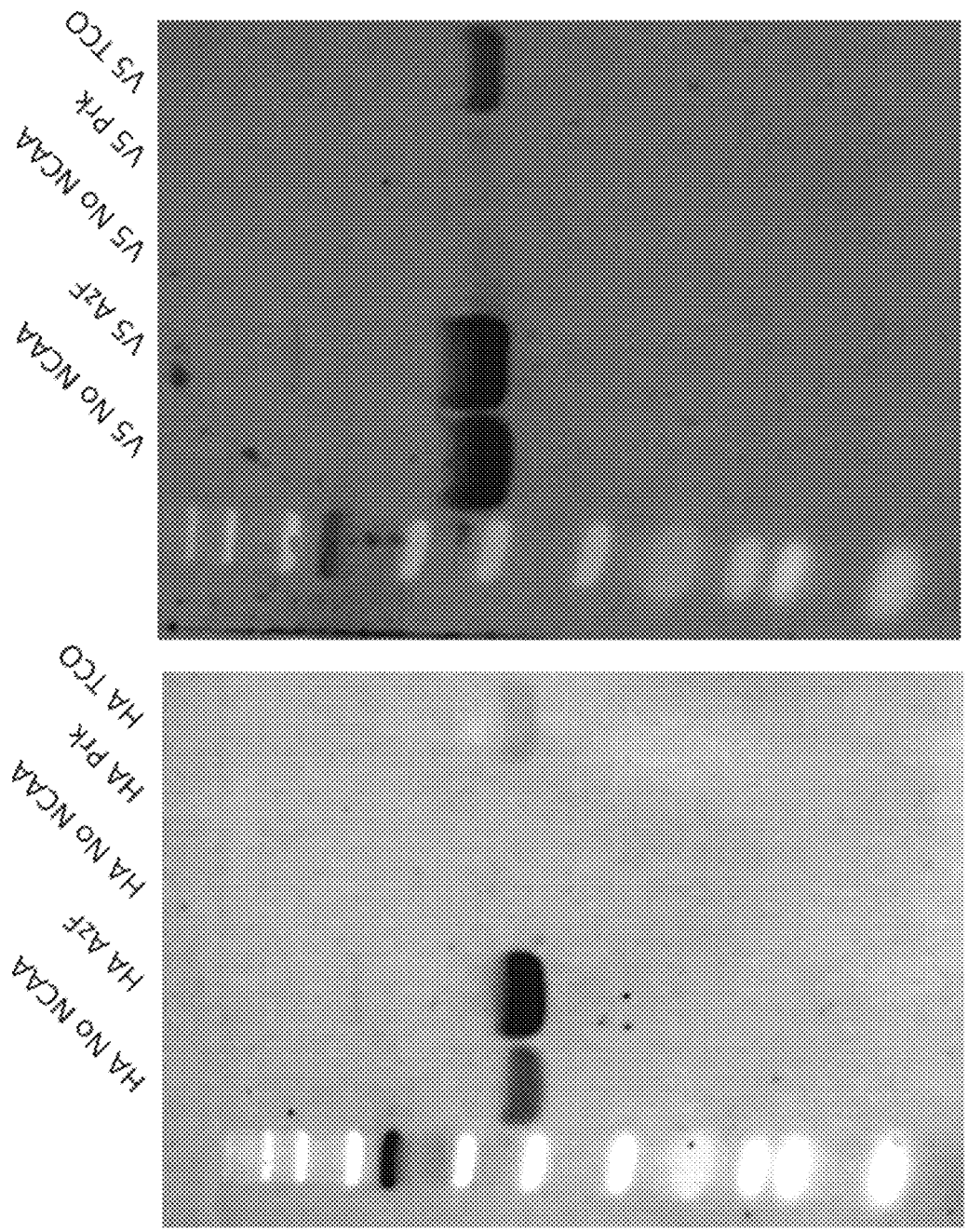
FIG. 17A-B depict western blots showing production of affinity-tag-peptide-MBP fusions containing NCAAs. The HA affinity tag blot (A) is visualized using a fluorescently conjugated anti-HA antibody and the V5 affinity tag blot (B) is visualized using a fluorescently conjugated anti-V5 antibody. While there is significant read through present as indicated by the presence of the tag in the no NCAA control, the data indicates successful production of HA-Azf, HA-TCO, and V5-TCO peptides.

A diazobenzene with orthogonal click chemistry modifications can act as a peptide-protein crosslinking moiety. For example, a diazobenzene with a tetrazine at one end and a DBCO (dibenzylcyclooctyne) on the other end could be used in a one-pot protocol wherein the DBCO reacts with an azide-modified peptide and the tetrazine reacts with a TCO-modified protein. Table 1 lists the combinations possible for either one-pot or sequential syntheses of peptide-diazobenzene-protein conjugates via use of a bifunctional diazobenzene structure. To develop a means of purifying engineered enzymes after photoswitch attachment, as well as to introduce a variety of different peptide groups to potentially impact the function of the enzyme upon photoswitching, an orthogonal click chemistry photoswitch will be utilized. The photoswitch will be synthesized with two reactive click chemistry groups; one for attachment to the enzyme and one for attachment to a short peptide that can be used as a target for affinity purification. A library of peptides will be created using the in vivo NCAA expression system previously described. Peptides containing an amber stop codon will be expressed using an expression system such as pET28 in a strain also containing the pEvol or another aaRS/tRNA system. The short peptide of interest can be expressed downstream of a second affinity tag, such as maltose binding protein with a protease cleavage site, FIG. 16. Western blots indication successful production of NCAA-containing peptide-MBP fusion are shown in FIG. 17. After affinity purification using the secondary affinity tag, the peptide can be removed by cleaving it at the protease cleavage site, resulting in a final peptide of interest containing an NCAA. The NCAA can then be used to attach the peptide to the photoswitch.

A representative protocol for example, reacting a tetrazine-diazobenzene-DBCO conjugate with an azide modified peptide and a TCO-modified protein would involve dissolving the tetrazine-diazobenzene-DBCO conjugate in a suitable buffer or water miscible organic solvent and then adding to an azide-modified peptide in reaction buffer so that the tetrazine-diazobenzene-DBCO conjugate is in 2-10 fold excess. The mixture can be incubated at room temperature for 1-4 hours of incubated at 4° C. for 2-12 hours. The peptide-diazobenzene-tetrazine conjugate formed in-situ would then be added to a solution of TCO-modified protein at 1.1-5 fold molar excess of the peptide-diazobenzene-tetrazine conjugate to TCO-modified protein. The mixture can be incubated for at least 30 min, and the resulting peptide-diazobenzene-protein conjugate can be purified by sequential size exclusion chromatography and affinity column chromatography. The conjugation reaction can also take place stepwise, whereby the tetrazine-diazobenzene-DBCO conjugate is reacted with the peptide, and the conjugate is purified by high performance liquid chromatography. The purified peptide-diazobenzene-tetrazine conjugate would be reacted with the TCO-modified protein as described. The orthogonality of the azide/DBCO and tetrazine/TCO click chemistries is described in Karver, M. R.; Weissleder, R.; Hilderbrand, S. A. *Angewandte Chemie Int. Ed.* 2012, 51, 920.

TABLE 1

Noncanonical amino acids that can be incorporated into TdT

| NCAA | Reactive group | Amino acid | Partner chemistry | Orthogonal chemistries |
| --- | --- | --- | --- | --- |
| 4-Azido-L-phenyl-alanine (AzF) | Azide | phenyl-alanine | alkyne (cyclooctyne or propargyl) | TCO/tetrazine |
| N-Propargyl-Lysine (PrK) | Propargyl (alkyne) | lysine | Azide | TCO/tetrazine |
| trans-Cyclooctene - L - Lysine (TCO*A) | TCO (trans-cyclooctene) | lysine | tetrazine | cyclooctyne or alkynel/azide |
| SCO-Lysine | Cyclooctyne | Lysine | Azide or H-tetrazine | TCO/Me-tetrazine |

The above-referenced amino acids can be incorporated into the TdT of the present invention using existing aaRS/tRNA systems. The click reactive group contained on the amino acid, as well as the partner chemistry required on the azobenzene are indicated. Orthogonal chemistries that can be used to attach other peptides to the azobenzene molecule are listed.

Example 14: Enzyme Synthesis

The mutated enzyme open reading frames were cloned into an expression vector that specifies an N-terminal 6×His tag followed by a thrombin cleavage site which is positioned immediately upstream of the enzyme coding region. Cloning techniques such as used herein are standard procedures and known to those of skill in the art.

Protein expression is controlled by an IPTG-inducible promoter. The protein expression plasmids were introduced into E. coli BL21 DE3 along with the plasmids containing tRNA synthetase/tRNA pairs allowing for the in vivo incorporation of NCAAs into proteins in E. coli in response to the amber codon, TAG. Examples of such plasmids include pEvol-pAzFRS.1.t1, for the incorporation of p-azido-1-phenylalanine (AzF) [6] and pEVOL-PylRS-AF for the incorporation of N-Propargyl-Lysine (PRK), trans-Cyclooctene-L-Lysine (TCO-K), or Cyclooctyne-Lysine (SCO-K) [7]. tRNA expression was induced by supplementing the growth medium with 2% arabinose. Protein expression is induced using 1 mM IPTG. The relevant NCAAs (AzF, PRK, TCO-K, SCO-K, SiChem) were supplemented into the growth medium at a final concentration of 2 mM. Growth and protein induction was carried out as described previously [8].

Cells were pelleted by centrifugation, resuspended in buffer A [8] and lysed using a Microfluidizer LMIO. Lysates were cleared by centrifugation, and the supernatants loaded on a purification column with an Ni-NTA agarose resin (Qiagen). Columns were washed and eluted as described previously [8].

Figure 18:
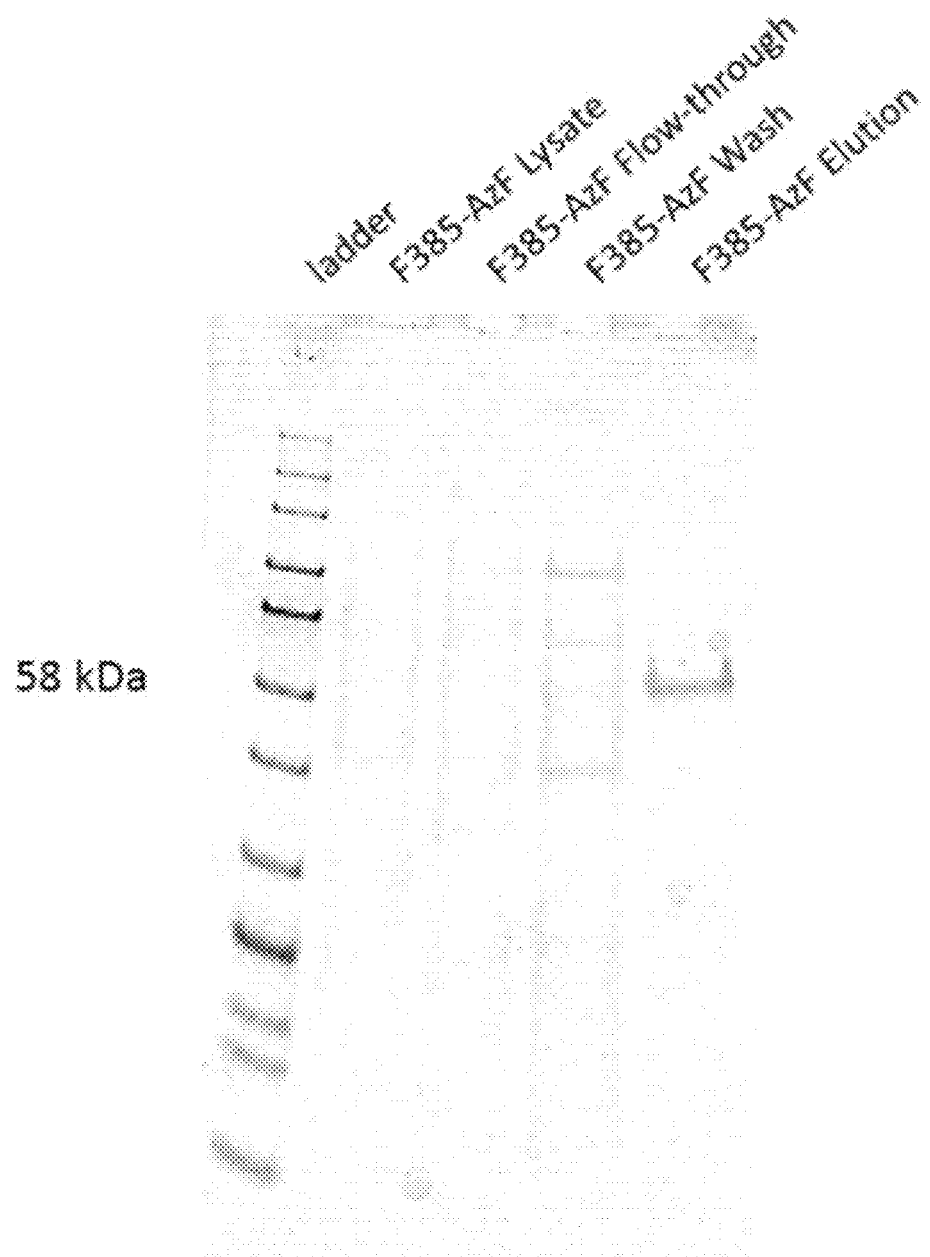
FIG. 18 depicts a protein gel showing the steps in the purification process, starting with the crude cell lysate which is loaded on to a Ni-NTA agarose column for affinity purification. The HIS-6 affinity tag on the enzyme causes it to be immobilized on the resin. There is no visible enzyme band in the flow-through or wash, but a band just above the 58 kDa marker on the ladder is present when the enzyme is eluted off the column with 1M imidazole, indicating successful expression and purification of the F385-AzF variant.
Figure 19:
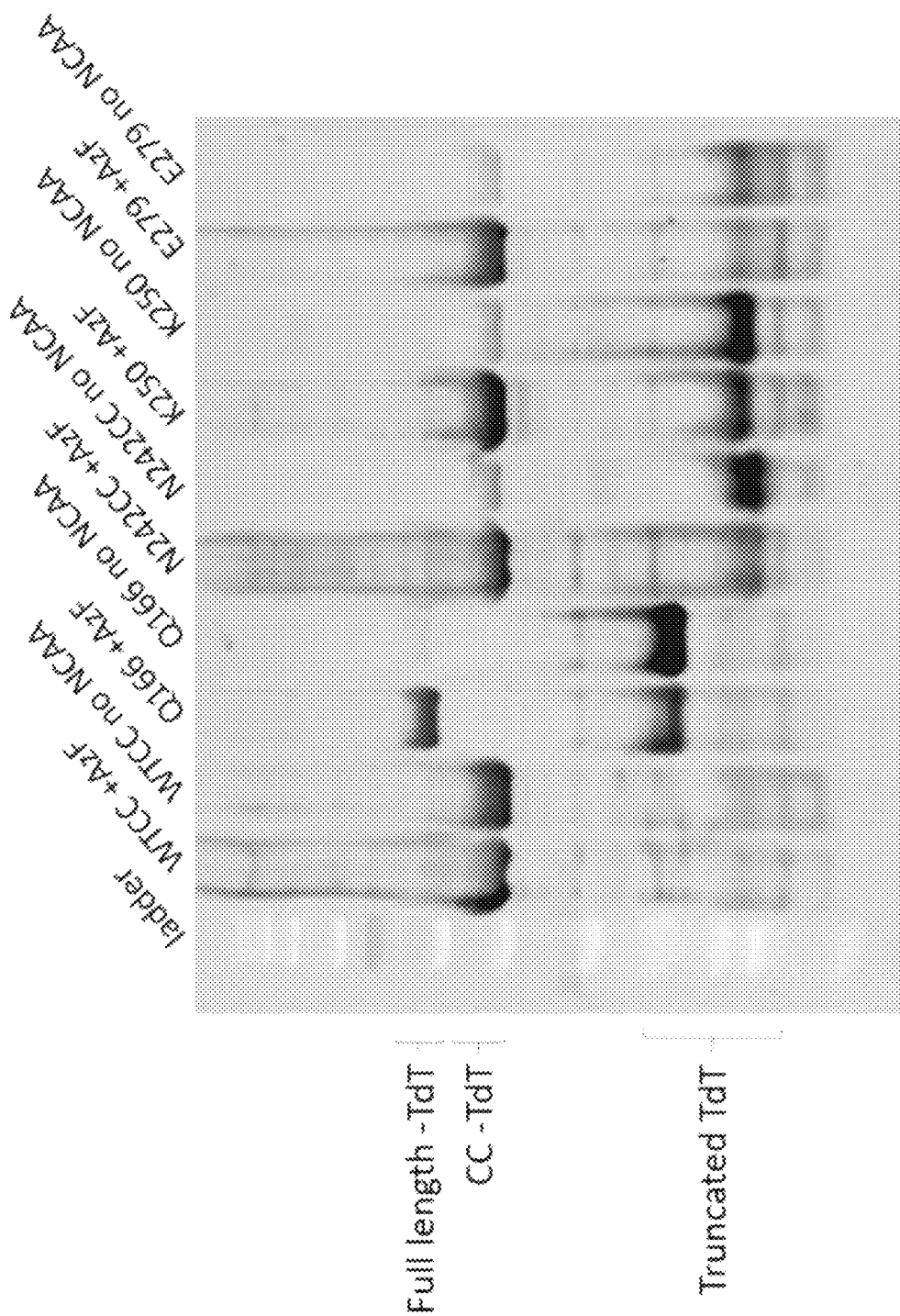
FIG. 19 depicts a western blot showing protein expression for enzymes containing amber codons at different locations and synthesized with and without the AzF NCAA. The blot was visualized using an fluorescently conjugated anti-HIS antibody. In the no NCAA control sample a truncated protein is observed. The shift in size of the truncate is a result of the varied position of the amber codon.
Figure 20:
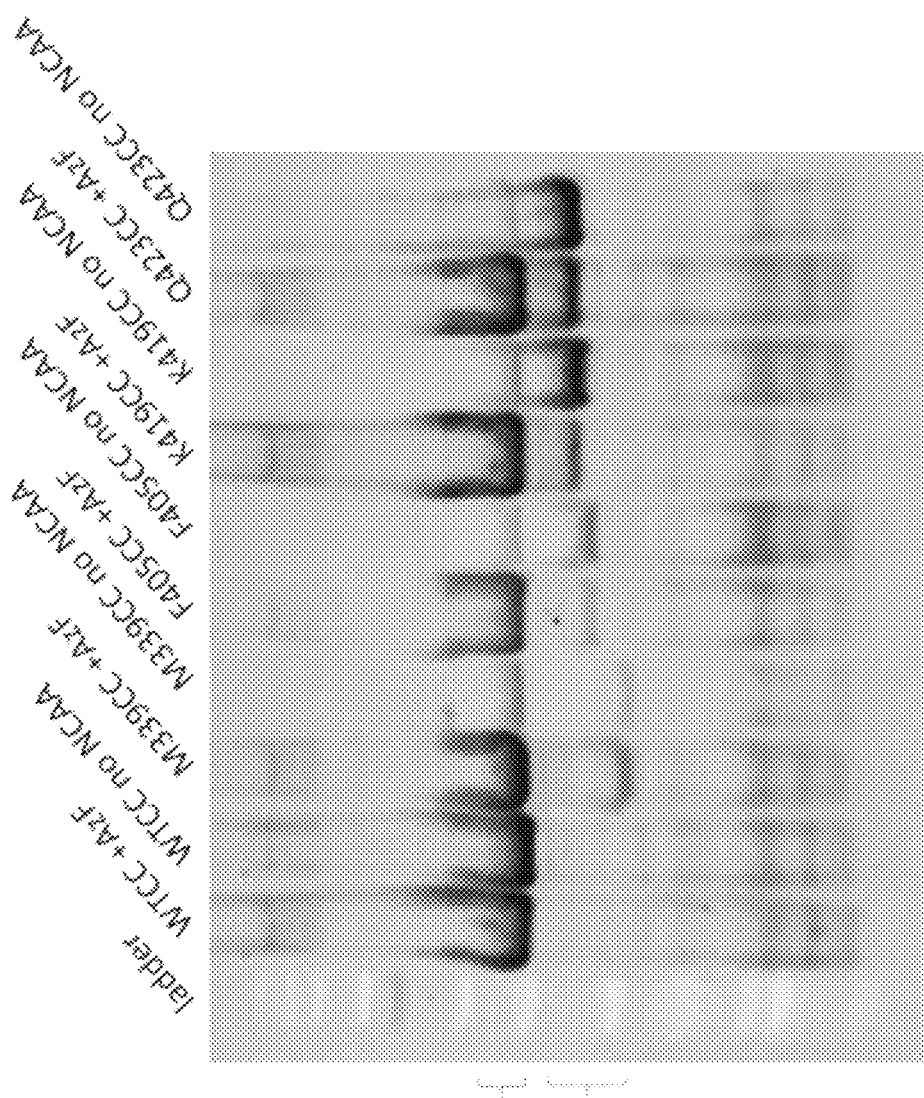
FIG. 20 depicts a western blot showing protein expression for enzymes containing amber codons at different locations and synthesized with and without the AzF NCAA. The blot was visualized using an fluorescently conjugated anti-HIS antibody. In the no NCAA control samples a truncated protein is observed. The shift in size of the truncate is a result of the varied position of the amber codon.
Figure 21:
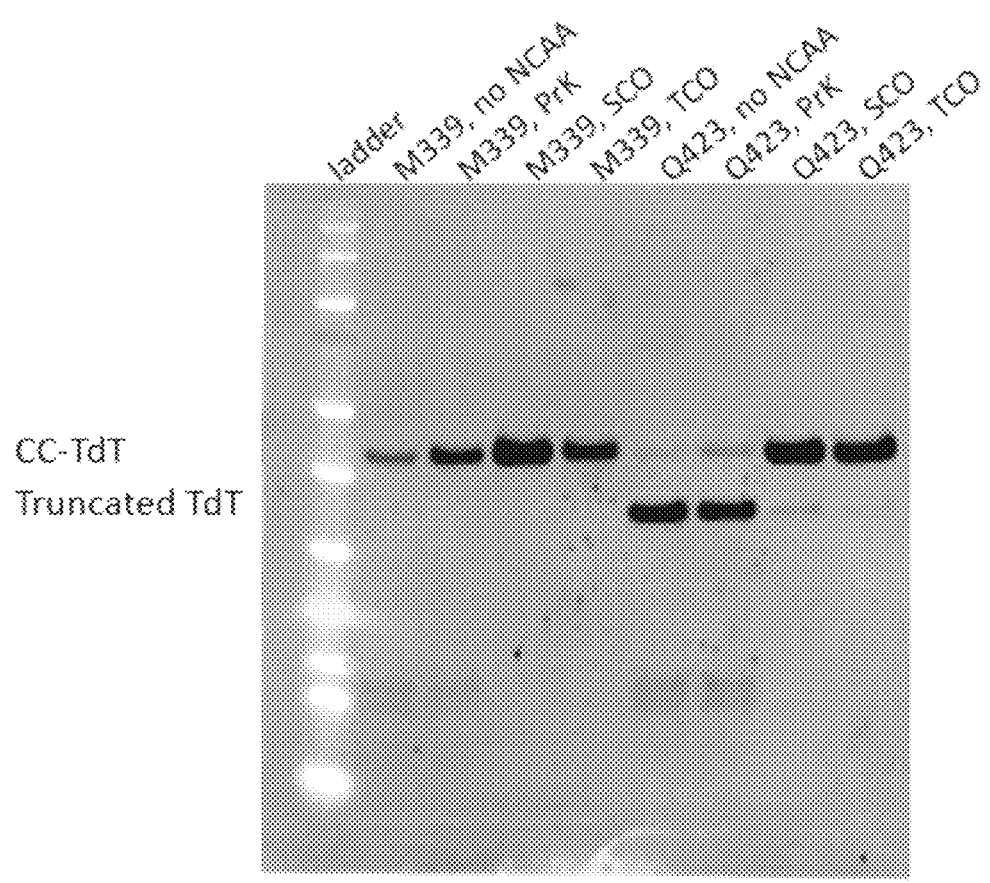
FIG. 21 depicts a western blot showing protein expression for enzymes containing amber codons at different locations and synthesized with PRK, SCO-K, TCO-K or without an NCAA. The blot was visualized using an fluorescently conjugated anti-HIS antibody. In the no NCAA control sample a truncated protein is observed. The shift in size of the truncate is a result of the varied position of the amber codon.

Eluted proteins were assessed for purity and NCAA incorporation by SDS-PAGE analysis and Western blot with an anti-his antibody, and assessed for function by carrying out a DNA synthesis reaction and characterizing the extension product on a TBE-Urea or pol-Urea gel. or one of the assays detailed below. SDS-PAGE analysis showing the affinity purification steps for an example enzyme, F385-AzF is shown in FIG. 18. Western blots, FIG. 19, 20, 21, show the successful expression of 13 different NCAA enzyme variants, Q166-AzF, N242CC-AzF, K250CC-AzF, E279CC-Azf, M339CC-AzF, F405CC-AzF, K419CC-AzF, Q423CC-AzF, M339-PRK, M339-SCO, M339-TCO, Q423-SCO, Q423-TCO. For many of the no NCAA control samples the truncated protein is observed. The shift in size of the truncate is a result of the varied position of the amber codon.

Figure 22:
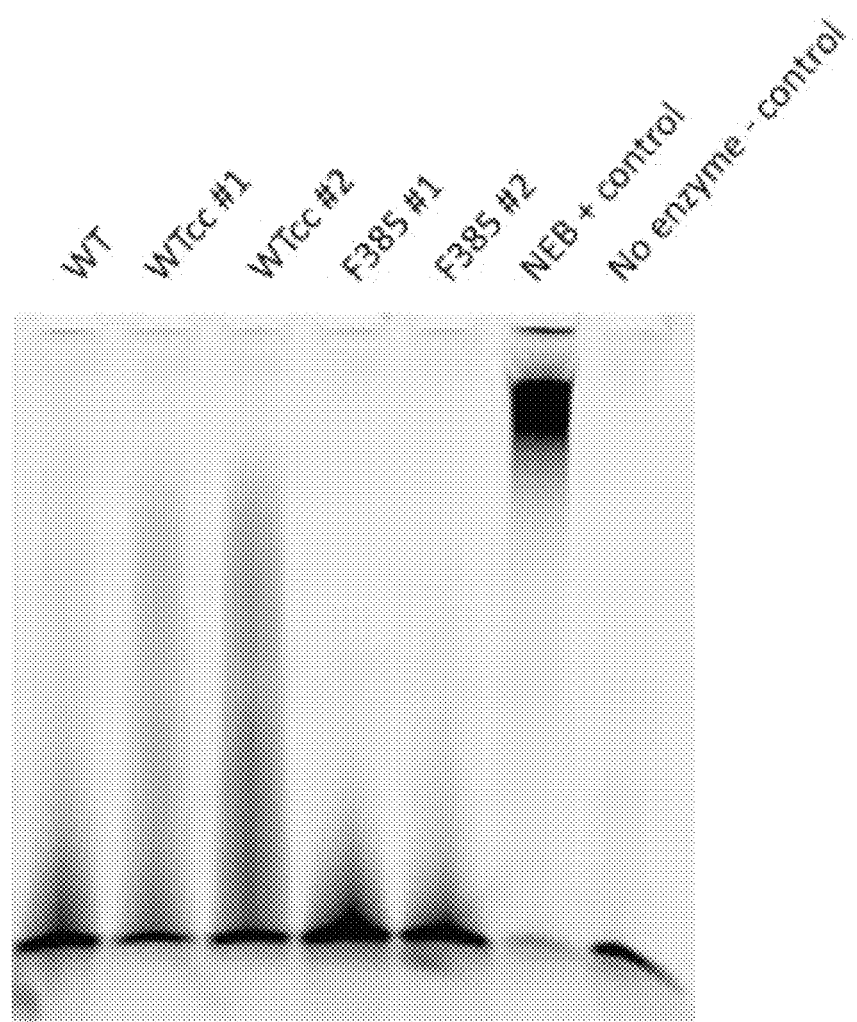
FIG. 22 depicts a TBE-Urea gel showing DNA extension of a fluorescent oligo with different enzymes. The no enzyme control on the right shows the unextended seed oligo. The activity of the F385-AzF enzyme is similar to that of the full length WT enzyme.
Figure 23:
FIG. 23 depicts a polyacrylamide-urea gel showing the product of 15 min DNA extension reaction using a fluorescent oligo with different enzymes and buffers with different metal ions. The first lane for each enzyme is Mg and Zn in a cacodylate buffer, the second lane is the standard Mg and Co in acetate buffer, the third lane is Mg and Co in cacodylate buffer, and the fourth lane is Mg and Mn in a cacodylate buffer.

Extension reactions, 1 hr, were carried out with WT, WTCC and F385-AzF enzymes and the products run on a 6% TBE-Urea gel, FIG. 22. The seed oligo is extended by all three enzymes, indicating each is active. A 15 min extension reaction was carried out with 4 different reaction buffers, each with different metal ions using WT, Q166CC-AzF and E279-CC-AzF, FIG. 23. The wild type enzyme exhibited activity in all the buffers, though activity was best in the R.

Figure 24:
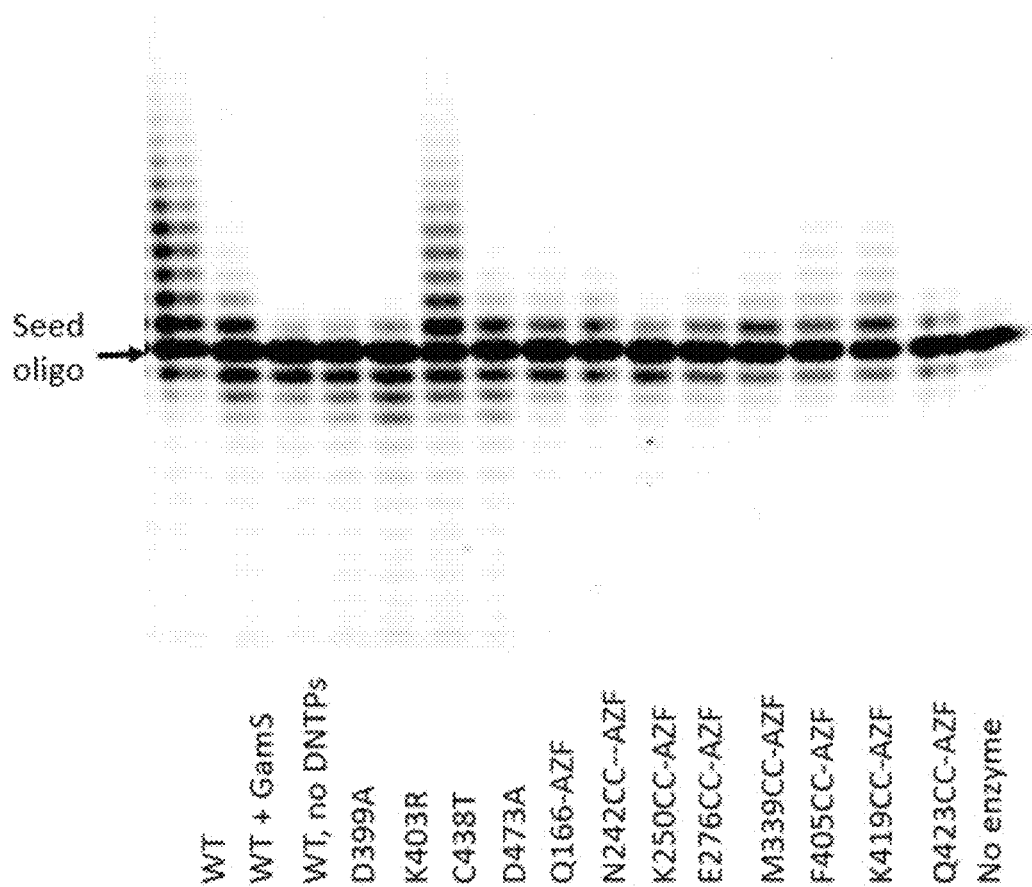
FIG. 24 depicts a polyacrylamide-urea gel showing the product of 30 s DNA extension reaction using a fluorescent oligo direct from cell lysate. These results demonstrate this assay provides a rapid means to assess enzyme function and kinetics without the need for individual affinity purification of each enzyme.

High Throughput Screening to Identify Functional Enzymes Direct from Cell Lysate To rapidly screen many engineered enzymes variants for polymerase function it is advantageous to be able to characterize DNA extension directly from a lysate of the cells used to synthesize the enzyme. After 16 hours of protein expression at 15° C., between 20-150 µL of each culture is transferred in to a 96 well plate. The plates are centrifuged at 2500 RCF for 15 minutes to pellet the cells. The pellets are washed twice with NEB TdT reaction buffer (50 mM potassium acetate. 20 mM Tris-acetate, 10 mM magnesium acetate, pH 7.9 @ 25° C.) and then the cells lysed at room temperature using ReadyLyse (Epicentre) lysozyme in NEB TdT reaction buffer. RNASE A is added to digest RNA that could interfere with the extension assay. Reagents for a TdT extension reaction are added to each well in the plate. An example of final reaction concentrations is 125 µM DNTP mix, 25 nM fluorescent oligo, and 0.25 mM $CoCl_2$. The reaction is carried out at 37° C. for the desired amount of time, typically between 30 s and 1 hour. A solution of 95% formamide and loading dye is added to the reaction and it is heated at 90° C. to kill the polymerase and denature the DNA to run on a gel. The product is run on a PAGE-Urea gel in an OWL S3S or S4S aluminum backed sequencer gel electrophoresis system to characterize the length of the extension products. The gel is fluorescently imaged on a Typhoon scanner. FIG. 24 shows DNA extension results from this assay for TdT variants with amino acids substitutions designed to alter the enzyme kinetics as well as a number of NCAA-containing TdT variants. These results demonstrate this assay provides a rapid means to assess enzyme function and kinetics without the need for individual affinity purification of each enzyme.

High Throughput Testing of Photocontrolled Enzymes

Figure 25:
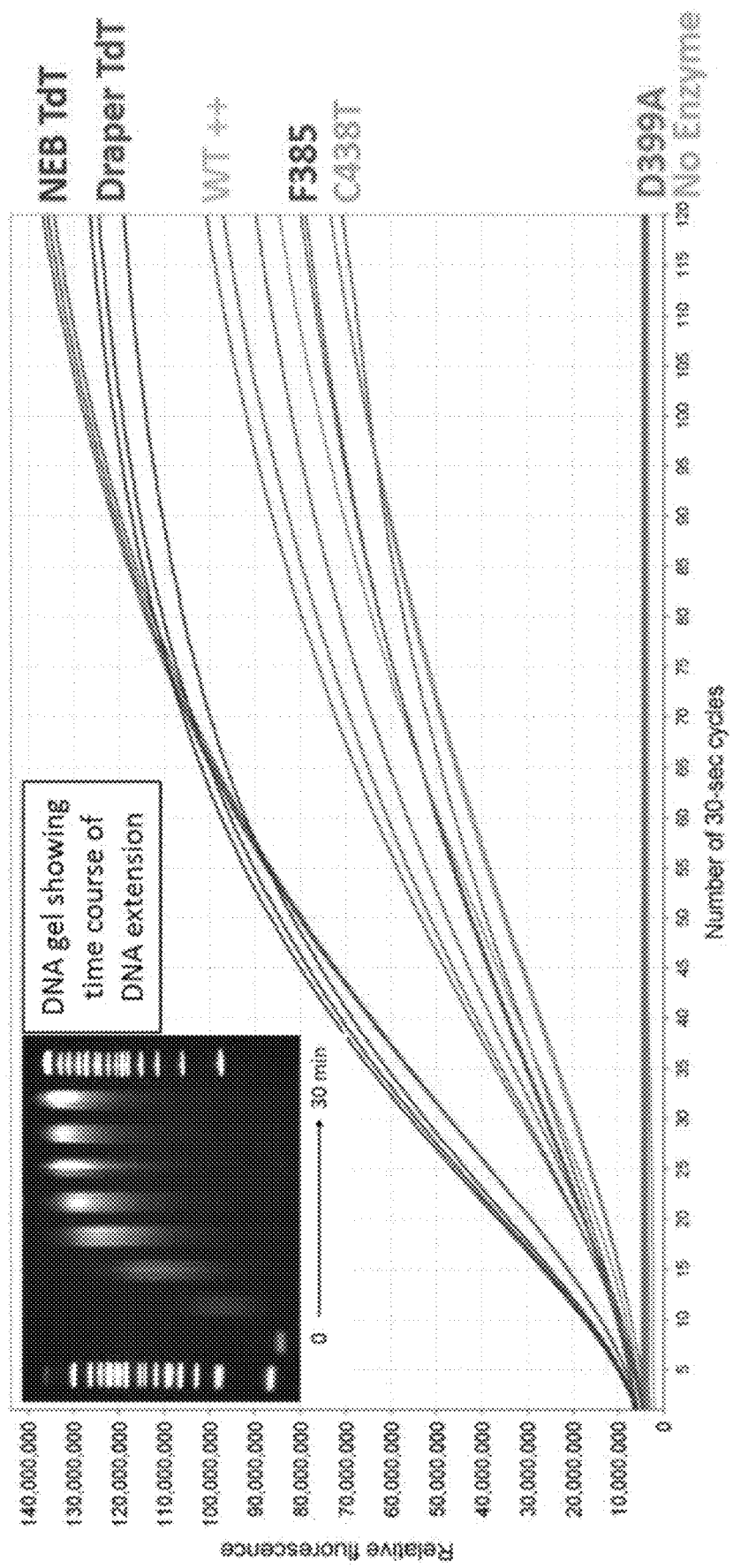
FIG. 25 depicts the results of a fluorescence-based assay for characterizing relative enzyme kinetics. The inset shows a time course of enzymatic DNA extension from gel electrophoresis for comparison.

A fluorescence-based assay enables the identification of enzyme variant-photoswitch-peptide combinations that exhibit photoregulation of DNA synthesis. The quantum yield of certain fluorescent molecules such as BOBO-3 (Invitrogen) increases when they bind to single-stranded DNA. Consequently, during a synthesis reaction, as DNA is extended by TdT, the fluorescence signal increases, as shown in FIG. 25. Functional, photocontrolled enzymes can be identified in a high throughput format in a 96-well plate by optically gating the photoswitch molecule while monitoring the fluorescence response for correlations. Dye molecules with absorbance and emission in the red is advantageous for this assay to prevent the excitation of fluorescence from influencing the photoswitch.

REFERENCES

The references described herein are incorporated by reference in their entirety.

1. Gouge, J., Rosario, S., Romain, F., Beguin, P., & Delarue, M. (2013). Structures of Intermediates along the Catalytic Cycle of Terminal Deoxynucleotidyl-transferase: Dynamical Aspects of the Two-Metal Ion Mechanism. Journal Of Molecular Biology, 425(22), 4334-4352. doi:10.1016/j.jmb.2013.07.009 PDB: 4I2J. 4I2I, 4I2H, 4I2G, 4I2F, 4I2E, 4I2D, 4I2C, 4I2B, 4I2A, 4I29, 4I28

2. Delarue, M., Boulé, J., Lescar, J., Expert-Bezançon, N., Jourdan, N., & Sukumar, N. et al. (2002). Crystal structures of a template-independent DNA polymerase: murine terminal deoxynucleotidyltransferase. The EMBO Journal, 21(3), 427-439. doi:10.1093/emboj/21.3.427

PBD: 1JMS, 1KDH, 1KEJ

3. Moon, A., Garcia-Diaz, M., Bebenek, K., Davis, B., Zhong, X., & Ramsden, D. et al. (2006). Structural insight into the substrate specificity of DNA Polymerase µ. Nature Structural & Molecular Biology, 14(1), 45-53. doi: 10.1038/nsmb1180

PDB: 2IHM, 4M04, 4LZG, 4LZD

4. Juárez, R., Ruiz, J., McElhinny, S., Ramsden, D., & Blanco, L. (2006). A specific loop in human DNA polymerase mu allows switching between creative and DNA-instructed synthesis. Nucleic Acids Research, 34(16), 4572-4582. doi: 10.1093/nar/gkl457

5. Costi, R., Cuzzucoli Crucitti, G., Pescatori, L., Messore, A., Scipione, L., & Tortorella, S. et al. (2013). New Nucleotide-Competitive Non-Nucleoside Inhibitors of Terminal Deoxynucleotidyl Transferase: Discovery, Characterization, and Crystal Structure in Complex with the Target. Journal Of Medicinal Chemistry, 56(18), 7431-7441. doi:10.1021/jm4010187 PDB: 4IQT, 4IQU, 4IQV, 4IQW 6. Amiram et al (2015) *Evolution of translation machinery in recoded bacteria enables multi-site incorporation of nonstandard amino acids. Nat Biotechnol.* 33(12):1272-1279. doi: 10.1038/nbt.3372

7. Plass, T., Milles, S., Koehler, C., Schultz, C., and Lemke, E. (2011). Genetically Encoded Copper-Free Click Chemistry Angew Chem Int Ed Engl, 50(17), 3878-3881. doi: 10.1002/anie.201008178

8. Boule et al., (1998). High-Level Expression of Murine Terminal Deoxynucleotidyl Transferase in *Escherichia coli* Grown at Low Temperature and Overexpressing argU tRNA Molecular Biotechnology 10, 199

While this invention has been particularly shown and described with references to preferred embodiments thereof, it will be understood by those skilled in the art that various changes in form and details may be made therein without departing from the scope of the invention encompassed by the following claims.

What is claimed is:

1. A genetically-engineered terminal deoxynucleotidyl transferase (TdT), wherein a wild-type TdT has been mutated at a single amino acid residue site to incorporate an azide or cyclooctene non-naturally occurring amino acid selected from the group consisting of: 4-Azido-L-phenylalanine (AzF), N-Propargyl-Lysine (PrK), Cyclooctene-L-Lysine (TCO-K) or Cyclooctyne-Lysine (SCO-K), wherein the non-naturally occurring amino acid is modified with a bifunctional azobenzene derivative comprising two orthogonal functional domains, wherein the first functional domain comprises a click reactive group for attachment to an affinity tag peptide for purification, and the second functional domain comprises a click reactive group whereby the bifunctional azobenzene derivative is attached to the non-naturally occurring amino acid, resulting in a TdT modified with the bifunctional azobenzene derivative capable of a reversible conformational change for controlled addition of a mononucleotide to the 3' end of a single-stranded polynucleotide.

2. The genetically-engineered TdT of claim 1, wherein the wild-type TdT comprises the amino acid sequence SEQ ID NO: 1, SEQ ID NO:5, or a homologous TdT comprising at least about 95% sequence identity with SEQ ID NO: 1 or SEQ ID NO:5.

3. The genetically-engineered TdT of claim 1, wherein the genetically-engineered TdT is photoisomerizable.

4. The genetically-engineered TdT of claim 1 wherein the bifunctional azobenzene derivative is a photoswitchable moiety.

5. The genetically-engineered TdT of claim 1, wherein the bifunctional azobenzene derivative regulates entry or binding of a mononucleotide to the active site of TdT.

6. The genetically-engineered TdT of claim 1, wherein the single amino acid residue site is exposed on the surface of the TdT protein.

7. The genetically-engineered TdT of claim 6, wherein the single amino acid residue site in the wild-type TdT is occupied by a lysine.

8. The genetically-engineered TdT of claim 7, wherein the lysine is selected from a position corresponding to position 199, 238, 247, 250, 276, 338 or 419 of the amino acid sequence SEQ ID NO: 1, or a position corresponding to a position 199, 238, 247, 250, 276, 338 or 419 in an amino acid sequence with at least 95% sequence identity to SEQ ID NO: 1.

9. The genetically-engineered TdT of claim 1, wherein the bifunctional azobenzene derivative regulates the translocation, or ratcheting, of the TdT along the single-stranded polynucleotide thereby inhibiting the addition of a mononucleotide to the polynucleotide.

10. The genetically-engineered TdT of claim 1, wherein the non-naturally occurring amino acid residue is incorporated into a site located in the loop of the TdT protein associated with DNA ratcheting function.

11. The genetically-engineered TdT of claim 1, wherein the non-naturally occurring amino acid residue is incorporated into a site located at a position corresponding to a position selected from the group consisting of: Q166, N242, K250, E279, F385, M339, F405, K419 or Q423 of SEQ ID NO:1, and a position corresponding to position Q166, N242, K250, E279, F385, M339, F405, K419 or Q423 of an amino acid sequence with at least 95% identity to SEQ ID NO: 1.

12. The genetically-engineered TdT of claim 1, wherein the click reactive group of the first functional domain and/or the click reactive group of the second functional domain of the bifunctional azobenzene derivative attaches to an attachment site that comprises an amine or alcohol.

13. The genetically-engineered TdT of claim 12, wherein the attachment site for the click reactive group of the first functional domain and/or the click reactive group of the second functional domain is an alcohol, and the alcohol is converted to be a ketone, aldehyde, or carboxylic acid.

14. The genetically-engineered TdT of claim 12, wherein (i) the click reactive group of the first functional domain and its attachment site on the affinity tag peptide are selected from a pair of clickable orthogonal groups, the pair comprising:

an azide-alkyne groups; tetrazine-norbornene groups; or tetrazine-trans-cyclooctene groups, and/or (ii) the click reactive group of the second functional domain and its attachment site on the non-naturally occurring amino acid are selected from a pair of clickable orthogonal groups, the pair comprising: an azide-alkyne groups; tetrazine-norbornene groups; or tetrazine-trans-cyclooctene groups.

15. The genetically-engineered TdT of claim 1, wherein, the bifunctional azobenzene derivative comprises the structure of:

a)

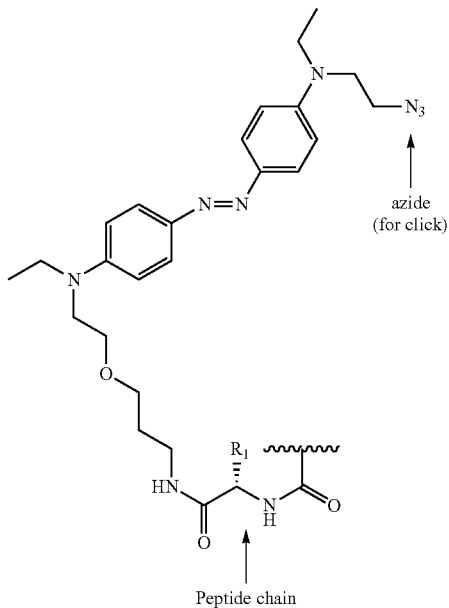

wherein, $R^1$ is selected from the group consisting of alkyl, substituted alkyl, acyl, cycloalkyl, substituted cycloalkyl, aryl, substituted aryl, heterocyclyl, substituted heterocyclyl, heteroaryl, and substituted heteroaryl; and optionally $R^1$ contains a bioconjugation moiety.

16. The genetically-engineered TdT of claim 1, wherein the bifunctional azobenzene derivative comprises the structure of:

b)

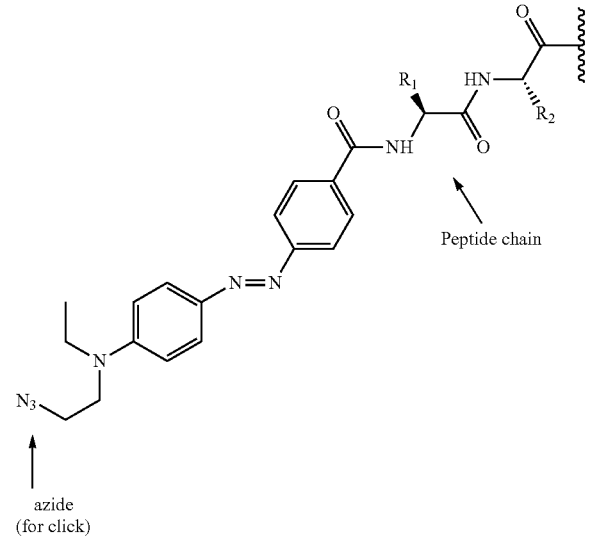

wherein, $R^1$ and $R^2$ are independently selected from the group consisting of alkyl, substituted alkyl, acyl, cycloalkyl, substituted cycloalkyl, aryl, substituted aryl, heterocyclyl, substituted heterocyclyl, heteroaryl, and substituted heteroaryl; and optionally $R^1$ and $R^2$ contain bioconjugation moieties.

17. The genetically-engineered TdT of claim 1, wherein the bifunctional azobenzene derivative comprises the structure of:

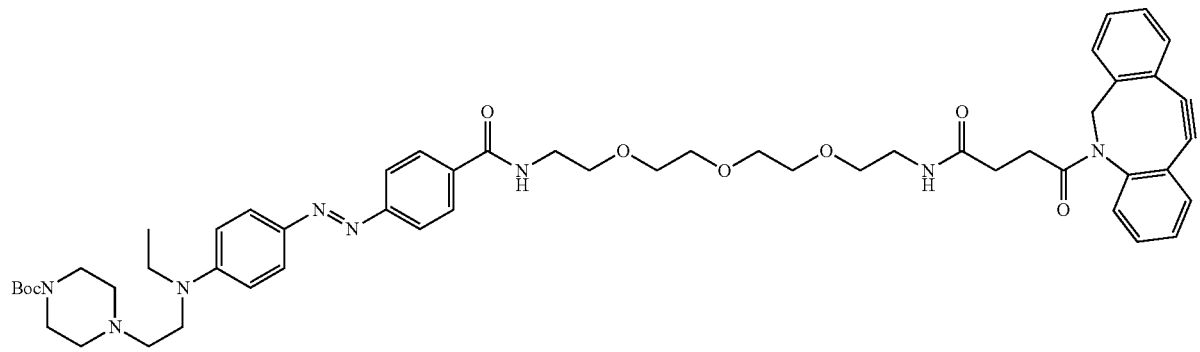 [SMILES: CCN(CCN1CCN(C(=O)OC(C)(C)C)CC1)c1ccc(/N=N/c2ccc(C(=O)NCCOCCOCCOCCNC(=O)CCC(=O)N3Cc4ccccc4C#Cc4ccccc43)cc2)cc1]

18. The genetically engineered TdT of claim 1, wherein the affinity tag peptide is selected from the group consisting of: HIS-6, Glutathione, c-Myc, HA, V5, Xpress, Biotin acceptor domain (BAD), VSVG, protein c, S-tag and FLAG.

19. The genetically engineered TdT of claim 1, wherein the click reactive group of the second functional domain of the bifunctional azobenzene derivative comprises a tetrazine.

20. The genetically-engineered TdT of claim 18, wherein the affinity tag peptide is FLAG.

21. A method of template-independent polynucleotide synthesis comprising the steps of contacting mononucleotide with the genetically-engineered TdT of claim 1, wherein the genetically-engineered TdT is immobilized on a solid support and is capable of attaching the mononucleotide to the 3' end of a single-stranded polynucleotide under conditions suitable for the incorporation of a mononucleotide to the 3' end of the single-stranded polynucleotide.

22. The method of claim 21, wherein the genetically-engineered TdT is photoisomerizable.

23. The method of claim 22, wherein the bifunctional azobenzene derivative of the genetically-engineered TdT is a photoswitchable moiety.

24. The method of claim 23, wherein the bifunctional azobenzene derivative regulates entry or binding of a mononucleotide to the active site of TdT.

25. The method of claim 21, wherein the mononucleotide contains a cleavable fluorescent label.

26. The method of claim 25, wherein the mononucleotide contains a phosphate coupled fluorophore that is cleaved upon attachment to the 3' end of the single-stranded polynucleotide.

27. A kit comprising reagents for template-independent polynucleotide synthesis and the genetically-engineered TdT of claim 1, wherein the genetically-engineered TdT is capable of attaching a mononucleotide to the 3' end of a single-stranded polynucleotide under conditions suitable for the incorporation of a mononucleotide to the 3' end of the single-stranded polynucleotide.

28. The kit of claim 27, wherein the bifunctional azobenzene derivative of the genetically-engineered TdT is a photoswitchable moiety.

29. The kit of claim 27, wherein the reagents include deoxynucleotide triphosphates (dNTPs), or analogs thereof.

30. The kit of claim 29, wherein the dNTPs contain a fluorescent label.

31. The kit of claim 30, wherein the fluorescent label is a cleavable fluorescent label.

* * * * *

SEQUENCE LISTING

```
<160> NUMBER OF SEQ ID NOS: 5

<210> SEQ ID NO 1
<211> LENGTH: 510
<212> TYPE: PRT
<213> ORGANISM: Murine

<400> SEQUENCE: 1

Met Asp Pro Leu Gln Ala Val His Leu Gly Pro Arg Lys Lys Arg Pro
1               5                   10                  15

Arg Gln Leu Gly Thr Pro Val Ala Ser Met Pro Tyr Asp Ile Arg Phe
                20                  25                  30

Arg Asp Leu Val Leu Phe Ile Leu Glu Lys Lys Met Gly Thr Thr Arg
            35                  40                  45

Arg Ala Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Phe Glu Leu Leu Asp Ile Ser Trp Leu Ile Glu Cys Met Gly
                100                 105                 110

Ala Gly Lys Pro Val Glu Met Met Gly Arg His Gln Leu Val Val Asn
            115                 120                 125

Arg Asn Ser Ser Pro Ser Pro Val Pro Gly Ser Gln Asn Val Pro Ala
        130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255
```

Gly Val Gly Leu Lys Thr Ala Glu Lys Trp Phe Arg Met Gly Phe Arg
                260                 265                 270

Thr Leu Ser Lys Ile Gln Ser Asp Lys Ser Leu Arg Phe Thr Gln Met
            275                 280                 285

Gln Lys Ala Gly Phe Leu Tyr Tyr Glu Asp Leu Val Ser Cys Val Asn
        290                 295                 300

Arg Pro Glu Ala Glu Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
                340                 345                 350

Ala Thr Glu Asp Glu Glu Gln Gln Leu Leu His Lys Val Thr Asp Phe
            355                 360                 365

Trp Lys Gln Gln Gly Leu Leu Leu Tyr Cys Asp Ile Leu Glu Ser Thr
        370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
                420                 425                 430

Val Asp Leu Val Met Cys Pro Tyr Asp Arg Arg Ala Phe Ala Leu Leu
            435                 440                 445

Gly Trp Thr Gly Ser Arg Gln Phe Glu Arg Asp Leu Arg Arg Tyr Ala
        450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Ile Phe Ala
                485                 490                 495

His Leu Gly Leu Asp Tyr Ile Glu Pro Trp Glu Arg Asn Ala
                500                 505                 510

<210> SEQ ID NO 2
<211> LENGTH: 509
<212> TYPE: PRT
<213> ORGANISM: Bovine

<400> SEQUENCE: 2

Met Asp Pro Leu Cys Thr Ala Ser Ser Gly Pro Arg Lys Lys Arg Pro
1               5                   10                  15

Arg Gln Val Gly Ala Ser Met Ala Ser Pro Pro His Asp Ile Lys Phe
            20                  25                  30

Gln Asn Leu Val Leu Phe Ile Leu Glu Lys Lys Met Gly Thr Thr Arg
        35                  40                  45

Arg Asn Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Glu Val Leu Glu Trp Leu Gln Val Gln Asn Ile Arg Ala Ser
                85                  90                  95

Ser Gln Leu Glu Leu Leu Asp Val Ser Trp Leu Ile Glu Ser Met Gly
            100                 105                 110

Ala Gly Lys Pro Val Glu Ile Thr Gly Lys His Gln Leu Val Val Arg
        115                 120                 125

Thr Asp Tyr Ser Ala Thr Pro Asn Pro Gly Phe Gln Lys Thr Pro Pro
            130                 135                 140

Leu Ala Val Lys Lys Ile Ser Gln Tyr Ala Cys Gln Arg Lys Thr Thr
145                 150                 155                 160

Leu Asn Asn Tyr Asn His Ile Phe Thr Asp Ala Phe Glu Ile Leu Ala
                165                 170                 175

Glu Asn Ser Glu Phe Lys Glu Asn Glu Val Ser Tyr Val Thr Phe Met
                180                 185                 190

Arg Ala Ala Ser Val Leu Lys Ser Leu Pro Phe Thr Ile Ile Ser Met
            195                 200                 205

Lys Asp Thr Glu Gly Ile Pro Cys Leu Gly Asp Lys Val Lys Cys Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Ser Leu Ser Lys Ile Met Ser Asp Lys Thr Leu Lys Phe Thr Lys Met
        275                 280                 285

Gln Lys Ala Gly Phe Leu Tyr Tyr Glu Asp Leu Val Ser Cys Val Thr
290                 295                 300

Arg Ala Glu Ala Glu Ala Val Gly Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Ile Gly His Asp Val Asp Phe Leu Ile Thr Ser Pro Gly
            340                 345                 350

Ser Ala Glu Asp Glu Glu Gln Leu Leu Pro Lys Val Ile Asn Leu Trp
        355                 360                 365

Glu Lys Lys Gly Leu Leu Leu Tyr Tyr Asp Leu Val Glu Ser Thr Phe
370                 375                 380

Glu Lys Phe Lys Leu Pro Ser Arg Gln Val Asp Thr Leu Asp His Phe
385                 390                 395                 400

Gln Lys Cys Phe Leu Ile Leu Lys Leu His His Gln Arg Val Asp Ser
                405                 410                 415

Ser Lys Ser Asn Gln Gln Glu Gly Lys Thr Trp Lys Ala Ile Arg Val
            420                 425                 430

Asp Leu Val Met Cys Pro Tyr Glu Asn Arg Ala Phe Ala Leu Leu Gly
        435                 440                 445

Trp Thr Gly Ser Arg Gln Phe Glu Arg Asp Ile Arg Arg Tyr Ala Thr
450                 455                 460

His Glu Arg Lys Met Met Leu Asp Asn His Ala Leu Tyr Asp Lys Thr
465                 470                 475                 480

Lys Arg Val Phe Leu Lys Ala Glu Ser Glu Glu Ile Phe Ala His
                485                 490                 495

Leu Gly Leu Asp Tyr Ile Glu Pro Trp Glu Arg Asn Ala
            500                 505

<210> SEQ ID NO 3
<211> LENGTH: 509
<212> TYPE: PRT
<213> ORGANISM: Human

```
<400> SEQUENCE: 3

Met Asp Pro Pro Arg Ala Ser His Leu Ser Pro Arg Lys Lys Arg Pro
1               5                   10                  15

Arg Gln Thr Gly Ala Leu Met Ala Ser Ser Pro Gln Asp Ile Lys Phe
            20                  25                  30

Gln Asp Leu Val Val Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Ala Gln Lys Val Gln Val Ser
                85                  90                  95

Ser Gln Pro Glu Leu Leu Asp Val Ser Trp Leu Ile Glu Cys Ile Arg
            100                 105                 110

Ala Gly Lys Pro Val Glu Met Thr Gly Lys His Gln Leu Val Val Arg
        115                 120                 125

Arg Asp Tyr Ser Asp Ser Thr Asn Pro Gly Pro Lys Thr Pro Pro
    130                 135                 140

Ile Ala Val Gln Lys Ile Ser Gln Tyr Ala Cys Gln Arg Arg Thr Thr
145                 150                 155                 160

Leu Asn Asn Cys Asn Gln Ile Phe Thr Asp Ala Phe Asp Ile Leu Ala
                165                 170                 175

Glu Asn Cys Glu Phe Arg Glu Asn Glu Asp Ser Cys Val Thr Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Ser Lys Val Lys Gly Ile
210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Thr Leu Ser Lys Val Arg Ser Asp Lys Ser Leu Lys Phe Thr Arg Met
        275                 280                 285

Gln Lys Ala Gly Phe Leu Tyr Tyr Glu Asp Leu Val Ser Cys Val Thr
    290                 295                 300

Arg Ala Glu Ala Glu Ala Val Ser Val Leu Val Lys Glu Ala Val Trp
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Glu Asp Glu Glu Gln Leu Leu Gln Lys Val Met Asn Leu Trp
        355                 360                 365

Glu Lys Lys Gly Leu Leu Leu Tyr Tyr Asp Leu Val Glu Ser Thr Phe
    370                 375                 380

Glu Lys Leu Arg Leu Pro Ser Arg Lys Val Asp Ala Leu Asp His Phe
385                 390                 395                 400

Gln Lys Cys Phe Leu Ile Phe Lys Leu Pro Arg Gln Arg Val Asp Ser
                405                 410                 415
```

```
Asp Gln Ser Ser Trp Gln Glu Gly Lys Thr Trp Lys Ala Ile Arg Val
            420                 425                 430

Asp Leu Val Leu Cys Pro Tyr Glu Arg Arg Ala Phe Ala Leu Leu Gly
            435                 440                 445

Trp Thr Gly Ser Arg Gln Phe Glu Arg Asp Leu Arg Arg Tyr Ala Thr
    450                 455                 460

His Glu Arg Lys Met Ile Leu Asp Asn His Ala Leu Tyr Asp Lys Thr
465                 470                 475                 480

Lys Arg Ile Phe Leu Lys Ala Glu Ser Glu Glu Ile Phe Ala His
                485                 490                 495

Leu Gly Leu Asp Tyr Ile Glu Pro Trp Glu Arg Asn Ala
            500                 505

<210> SEQ ID NO 4
<211> LENGTH: 522
<212> TYPE: PRT
<213> ORGANISM: Shark

<400> SEQUENCE: 4

Met Ser Leu Ala Gly Ser Leu Gly Gly Met Gly Ile Ile Pro Lys Arg
1               5                   10                  15

Lys Arg Gln Lys Val Thr Glu Val Cys Ser Ser Gln Ser Lys His Gln
                20                  25                  30

Val Arg Phe Gln Asp Leu Thr Ile Phe Ile Val Glu Arg Lys Met Gly
            35                  40                  45

Ser Ser Arg Arg Ser Phe Leu Met Asp Leu Ala Arg Lys Lys Gly Phe
    50                  55                  60

Arg Val Glu Asp Val Met Ser Asp Ser Val Thr His Ile Val Thr Glu
65                  70                  75                  80

Asn Asn Ser Trp Asp Glu Ile Trp Asp Trp Ile Gln Asn Leu Lys Leu
                85                  90                  95

Leu Asn Ala Asp Lys Leu Lys Met Leu Asn Ile Ser Trp Phe Thr Asp
                100                 105                 110

Ser Met Ala Ala Gly Lys Pro Val Glu Ile Glu Glu Arg His Lys Leu
            115                 120                 125

Gln Val Gln Lys Met Leu Gln Ser Asn Ser Pro Leu Pro Pro Pro Val
    130                 135                 140

Val Thr Ile Ser Gln Tyr Ala Cys Gln Arg Arg Ser Thr Leu Asn Asn
145                 150                 155                 160

Arg Asn Lys Ile Phe Thr Asp Ala Leu Glu Ile Leu Ala Glu Asn Phe
                165                 170                 175

Glu Phe Asn Glu Asn Glu Ser Ala Tyr Val Ala Phe Ala Arg Ala Thr
            180                 185                 190

Ser Leu Leu Lys Ser Leu Pro Tyr Thr Ile Ser Lys Met Ala Ala Leu
    195                 200                 205

Asp Gly Leu Pro Cys Phe Gly Asp Gln Thr Arg Ala Ile Ile Glu Glu
210                 215                 220

Ile Leu Glu Asp Gly Val Ser Ser Lys Val Asp Leu Leu Cys Asp
225                 230                 235                 240

Glu Lys Tyr Lys Ala Arg Lys Leu Phe Thr Ser Val Phe Gly Val Gly
                245                 250                 255

Leu Lys Thr Ala Asp Lys Trp Tyr Gly Gln Gly Phe Arg Thr Leu Glu
            260                 265                 270

Ala Val Lys Ala Ser Lys Asp Leu Lys Phe Thr Lys Met Gln Lys Ala
```

```
            275                 280                 285
Gly Phe Leu Tyr Tyr Glu Asp Ile Asn Asn Ala Val Thr Arg Pro Glu
    290                 295                 300

Ala Glu Ala Val Ala Gln Ile Ile Glu Thr Ile Val His Asn Tyr Ala
305                 310                 315                 320

Pro Asp Ala Ile Val Thr Leu Thr Gly Gly Phe Arg Arg Gly Lys Glu
                325                 330                 335

Thr Gly His Asp Val Asp Phe Leu Ile Ser Cys Pro Glu Thr Met Asp
            340                 345                 350

Glu Asn Phe Leu Arg Lys Ile Val Asn Lys Leu Asp Phe Arg Gly Leu
        355                 360                 365

Leu Leu Tyr Tyr Asp Met Val Glu Ala Thr Phe Glu Lys Arg Lys Leu
    370                 375                 380

Ser Ser Gln Lys Tyr Asp Ala Met Asp His Phe Gln Lys Cys Phe Leu
385                 390                 395                 400

Ile Leu Lys Leu Asn Lys Ala Leu Val Lys Asn Arg Val Leu Ser Met
                405                 410                 415

Ser Ser Val Ser Ala Ala Arg Pro Thr Asp Glu Gly Ala Glu Pro Glu
            420                 425                 430

Val Lys Thr Gln Ile Lys Asp Trp Lys Ala Ile Arg Val Asp Leu Val
        435                 440                 445

Ile Val Pro Thr Gln Gln Phe Ala Tyr Ala Leu Leu Gly Trp Thr Gly
    450                 455                 460

Ser Arg Gln Phe Glu Arg Asp Leu Arg Arg Tyr Thr Asn His Glu Lys
465                 470                 475                 480

Ser Met Ile Leu Asp Asn His Gly Leu Tyr Asp Arg Lys Lys Lys Ile
                485                 490                 495

Phe Leu Asn Ala Lys Thr Glu Glu Glu Ile Phe Ala His Leu Asp Leu
            500                 505                 510

Glu Tyr Ile Glu Pro Trp Glu Arg Asn Ala
        515                 520

<210> SEQ ID NO 5
<211> LENGTH: 381
<212> TYPE: PRT
<213> ORGANISM: Murine Catalytic Core Added (APM)

<400> SEQUENCE: 5

Asn Ser Ser Pro Ser Pro Val Pro Gly Ser Gln Asn Val Pro Ala Pro
1               5                   10                  15

Ala Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Leu Arg Glu Asn Glu Gly Ser Cys Leu Ala Phe Met Arg
    50                  55                  60
```

```
Ala Ser Ser Val Leu Lys Ser Leu Pro Phe Pro Ile Thr Ser Met Lys
 65                  70                  75                  80

Asp Thr Glu Gly Ile Pro Cys Leu Gly Asp Lys Val Lys Ser Ile Ile
                 85                  90                  95

Glu Gly Ile Ile Glu Asp Gly Glu Ser Ser Glu Ala Lys Ala Val Leu
            100                 105                 110

Asn Asp Glu Arg Tyr Lys Ser Phe Lys Leu Phe Thr Ser Val Phe Gly
            115                 120                 125

Val Gly Leu Lys Thr Ala Glu Lys Trp Phe Arg Met Gly Phe Arg Thr
130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
            195                 200                 205

Lys Met Thr Gly His Asp Val Asp Phe Leu Ile Thr Ser Pro Glu Ala
210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
            260                 265                 270

Gln Lys Cys Phe Leu Ile Leu Lys Leu Asp His Gly Arg Val His Ser
            275                 280                 285

Glu Lys Ser Gly Gln Gln Glu Gly Lys Gly Trp Lys Ala Ile Arg Val
            290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Arg Thr
            340                 345                 350

Lys Arg Val Phe Leu Glu Ala Glu Ser Glu Glu Ile Phe Ala His
            355                 360                 365

Leu Gly Leu Asp Tyr Ile Glu Pro Trp Glu Arg Asn Ala
370                 375                 380
```